US009386942B2

(12) United States Patent
Chi Sing et al.

(10) Patent No.: US 9,386,942 B2
(45) Date of Patent: *Jul. 12, 2016

(54) APPARATUS, SYSTEMS, AND METHODS FOR LOCALIZING MARKERS OR TISSUE STRUCTURES WITHIN A BODY

(75) Inventors: Eduardo Chi Sing, Dana Point, CA (US); Tommy G. Nguyen, Irvine, CA (US); Luis Urquidi, Oceanside, CA (US)

(73) Assignee: CIANNA MEDICAL, INC., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/053,197

(22) Filed: Mar. 21, 2011

(65) Prior Publication Data

US 2011/0313288 A1    Dec. 22, 2011

Related U.S. Application Data

(63) Continuation-in-part of application No. 12/824,139, filed on Jun. 25, 2010.

(60) Provisional application No. 61/220,900, filed on Jun. 26, 2009, provisional application No. 61/255,469, filed on Oct. 27, 2009, provisional application No. 61/297,694, filed on Jan. 22, 2010.

(51) Int. Cl.
*A61B 6/12* (2006.01)
*A61B 5/06* (2006.01)
(Continued)

(52) U.S. Cl.
CPC ............... *A61B 5/06* (2013.01); *A61B 5/0507* (2013.01); *A61B 5/064* (2013.01); *A61B 5/4312* (2013.01);
(Continued)

(58) Field of Classification Search
CPC combination set(s) only.
See application file for complete search history.

(56) References Cited

U.S. PATENT DOCUMENTS

| 5,361,070 A | 11/1994 | McEwan |
| 5,573,012 A | 11/1996 | McEwan |

(Continued)

FOREIGN PATENT DOCUMENTS

| EP | 1374793 A1 | 2/2004 |
| WO | 0239918 A1 | 5/2002 |

(Continued)

OTHER PUBLICATIONS

Hughes, Jenevieve H. et al., A Multi-site Vlidation Trial of Radioactive Seed Localization as an Alternative to Wire Localization, The Breast Journal, vol. 14 No. 2, 2008 Blackwell Publishing, Inc., 5 pages.

(Continued)

*Primary Examiner* — Katherine Fernandez
*Assistant Examiner* — Farshad Negarestan
(74) *Attorney, Agent, or Firm* — William A. English; Vista IP Law Group LLP

(57) ABSTRACT

Apparatus, systems, and methods are provided for localizing lesions within a patient's body, e.g., within a breast. The system may include one or more markers implantable within or around the target tissue region, and a probe for transmitting and receiving electromagnetic signals to detect the one or more markers. During use, the marker(s) are into a target tissue region, and the probe is placed against the patient's skin to detect and localize the marker(s). A tissue specimen, including the lesion and the marker(s), is then removed from the target tissue region based at least in part on the localization information from the probe.

28 Claims, 50 Drawing Sheets

(51) Int. Cl.
  *A61B 5/05* (2006.01)
  *A61B 5/00* (2006.01)
  *A61B 8/08* (2006.01)
  *A61B 19/00* (2006.01)
  *A61B 17/00* (2006.01)

(52) U.S. Cl.
  CPC ............. *A61B 8/0825* (2013.01); *A61B 8/0841* (2013.01); *A61B 19/54* (2013.01); *A61B 19/5225* (2013.01); *A61B 2017/00438* (2013.01); *A61B 2017/00442* (2013.01); *A61B 2019/5251* (2013.01); *A61B 2019/5272* (2013.01); *A61B 2019/547* (2013.01); *A61B 2019/5408* (2013.01); *A61B 2019/5475* (2013.01); *A61B 2019/5487* (2013.01); *A61B 2034/2072* (2016.02); *A61B 2090/3975* (2016.02)

(56) References Cited

U.S. PATENT DOCUMENTS

| | | | |
|---|---|---|---|
| 5,764,162 | A | 6/1998 | Ehrlich |
| 5,766,208 | A | 6/1998 | McEwan |
| 5,853,366 | A | 12/1998 | Dowlatshahi |
| 5,879,357 | A | 3/1999 | Heaton et al. |
| 6,363,940 | B1 | 4/2002 | Krag |
| 6,496,717 | B2 | 12/2002 | Cox et al. |
| 6,575,991 | B1 | 6/2003 | Chesbrough et al. |
| 6,725,083 | B1 * | 4/2004 | Burbank et al. ............. 600/431 |
| 6,914,552 | B1 | 7/2005 | McEwan |
| 7,044,957 | B2 * | 5/2006 | Foerster et al. ............. 606/185 |
| 7,166,120 | B2 * | 1/2007 | Kusleika ..................... 606/191 |
| 7,174,201 | B2 | 2/2007 | Govari et al. |
| 7,535,363 | B2 * | 5/2009 | Gisselberg et al. ........ 340/572.5 |
| 7,569,065 | B2 | 8/2009 | Chesbrough et al. |
| 8,052,708 | B2 | 11/2011 | Chesbrough et al. |
| 2003/0018246 | A1 | 1/2003 | Govari et al. |
| 2003/0192557 | A1 | 10/2003 | Krag et al. |
| 2005/0059884 | A1 | 3/2005 | Krag |
| 2006/0025795 | A1 | 2/2006 | Chesbrough et al. |
| 2006/0258933 | A1 * | 11/2006 | Ellis et al. ..................... 600/407 |
| 2007/0038014 | A1 | 2/2007 | Cox et al. |
| 2007/0093726 | A1 * | 4/2007 | Leopold et al. ............... 600/562 |
| 2008/0027313 | A1 * | 1/2008 | Shachar ........................ 600/424 |
| 2008/0071169 | A1 | 3/2008 | Craddock et al. |
| 2008/0086046 | A1 | 4/2008 | Petcavich et al. |
| 2008/0200802 | A1 * | 8/2008 | Bhavaraju et al. ........... 600/426 |
| 2008/0281190 | A1 | 11/2008 | Petcavich et al. |
| 2009/0281422 | A1 * | 11/2009 | Salama et al. ................ 600/430 |
| 2009/0299174 | A1 * | 12/2009 | Wright et al. ................. 600/424 |

FOREIGN PATENT DOCUMENTS

| | | |
|---|---|---|
| WO | 2007087447 A2 | 8/2007 |
| WO | 2007117478 A2 | 10/2007 |

OTHER PUBLICATIONS

Nilavalan, R. et al., Wideband Microstrip Patch Antenna Desiign for Breast Cancer Tumour Detection, IEEE Xplore/IEEE.org, Apr. 30, 2007, Institution of Engineering and Technology, 1 page.

Stephan, Pam, Wire Localization Procedure—Breast Biopsy or Lumpectomy, About.com/Breast Cancer, Sep. 8, 2008, American Cancer Society/Ohio State Medical Center, 2 pages.

Azevedo, Stephen & Thomas E. McEwan, Micropower Impulse Radar, Science & Technology Review, Jan./Feb. 1996, 7 pages.

* cited by examiner

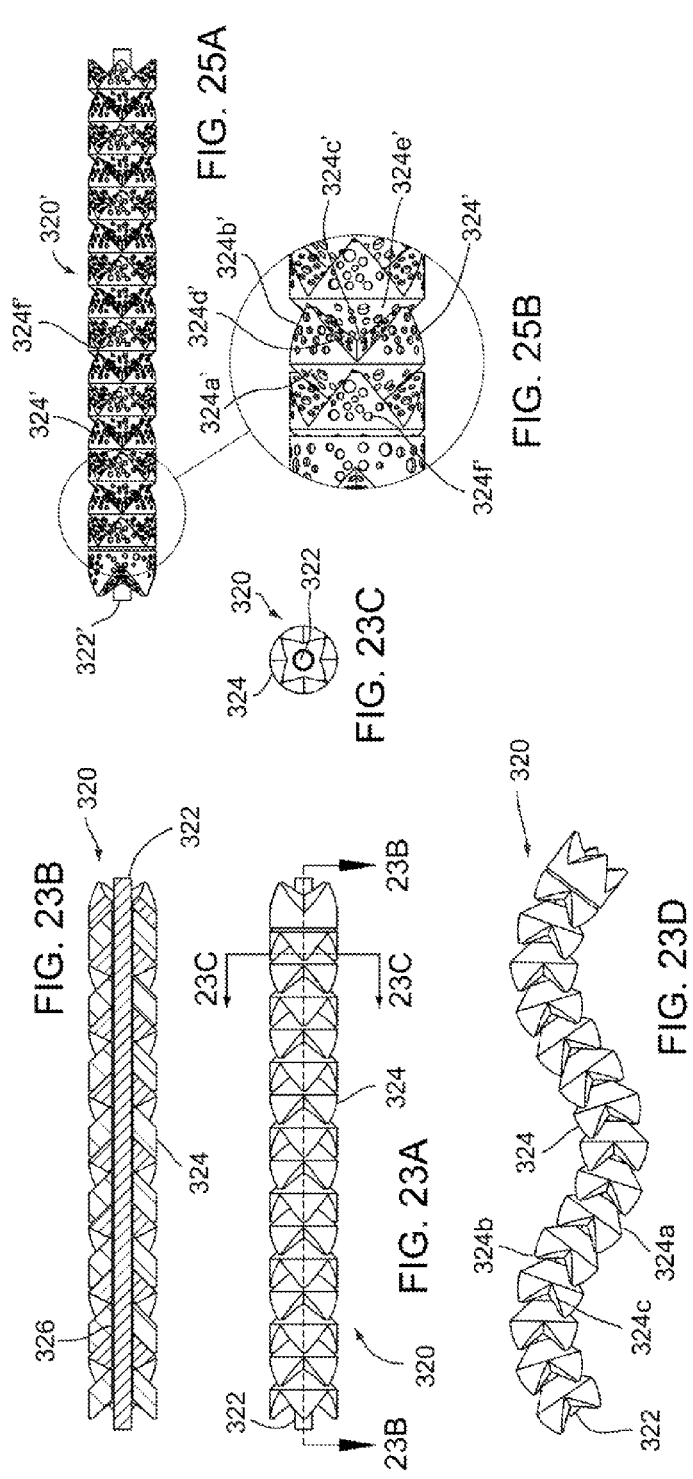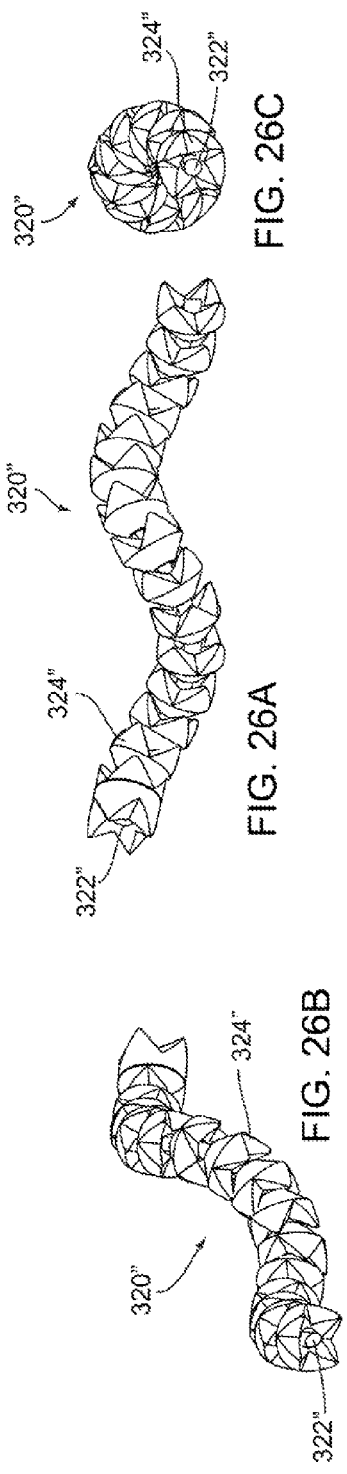

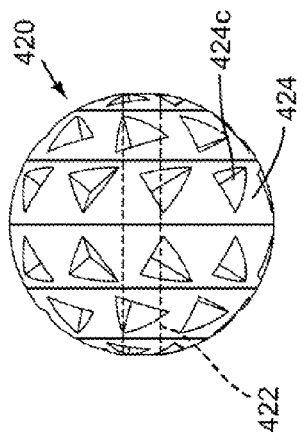
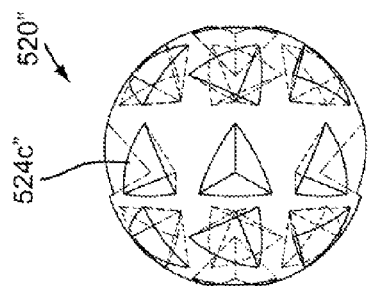
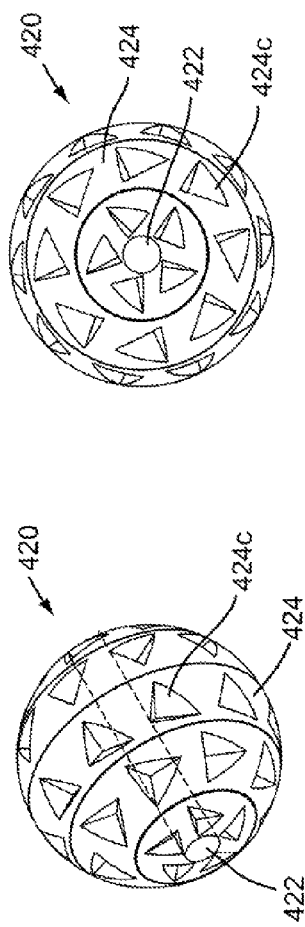
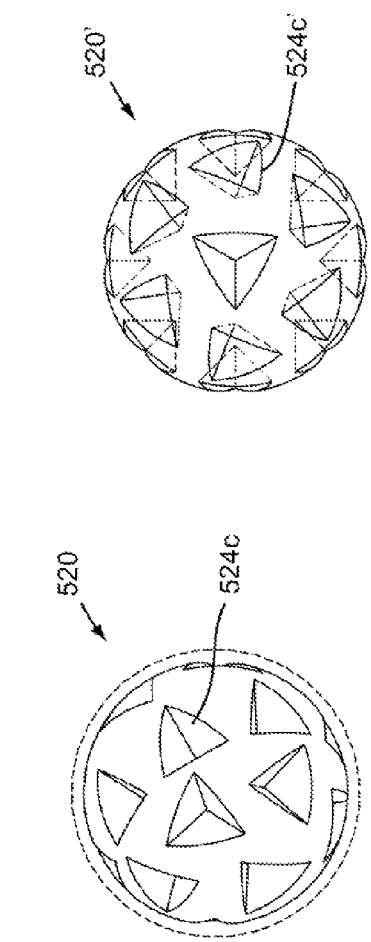

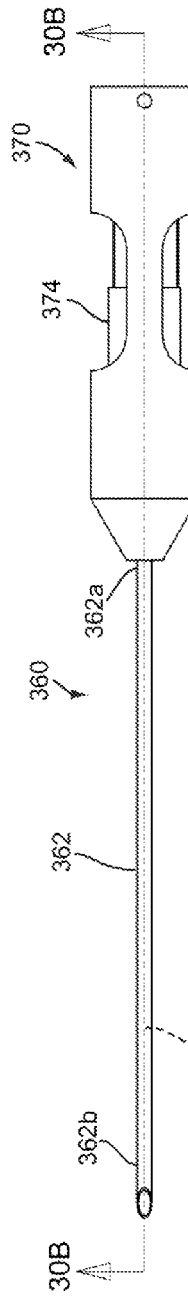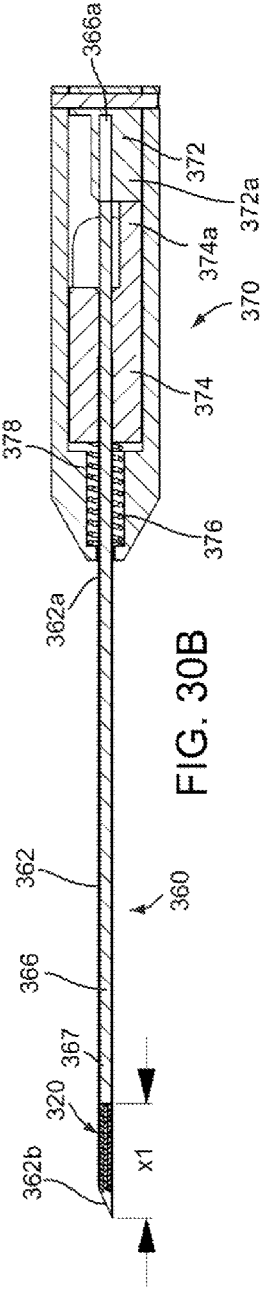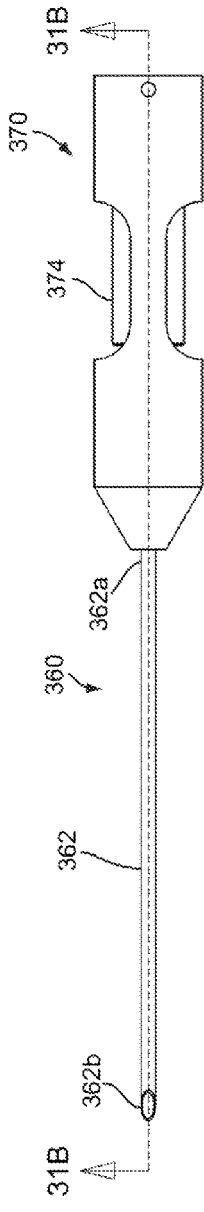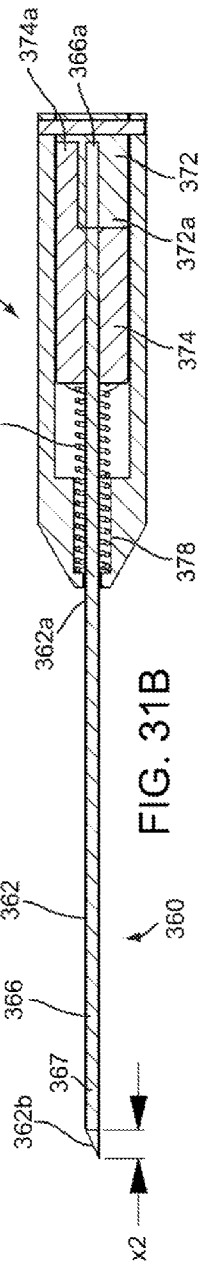
FIG. 30A
FIG. 30B
FIG. 31A
FIG. 31B

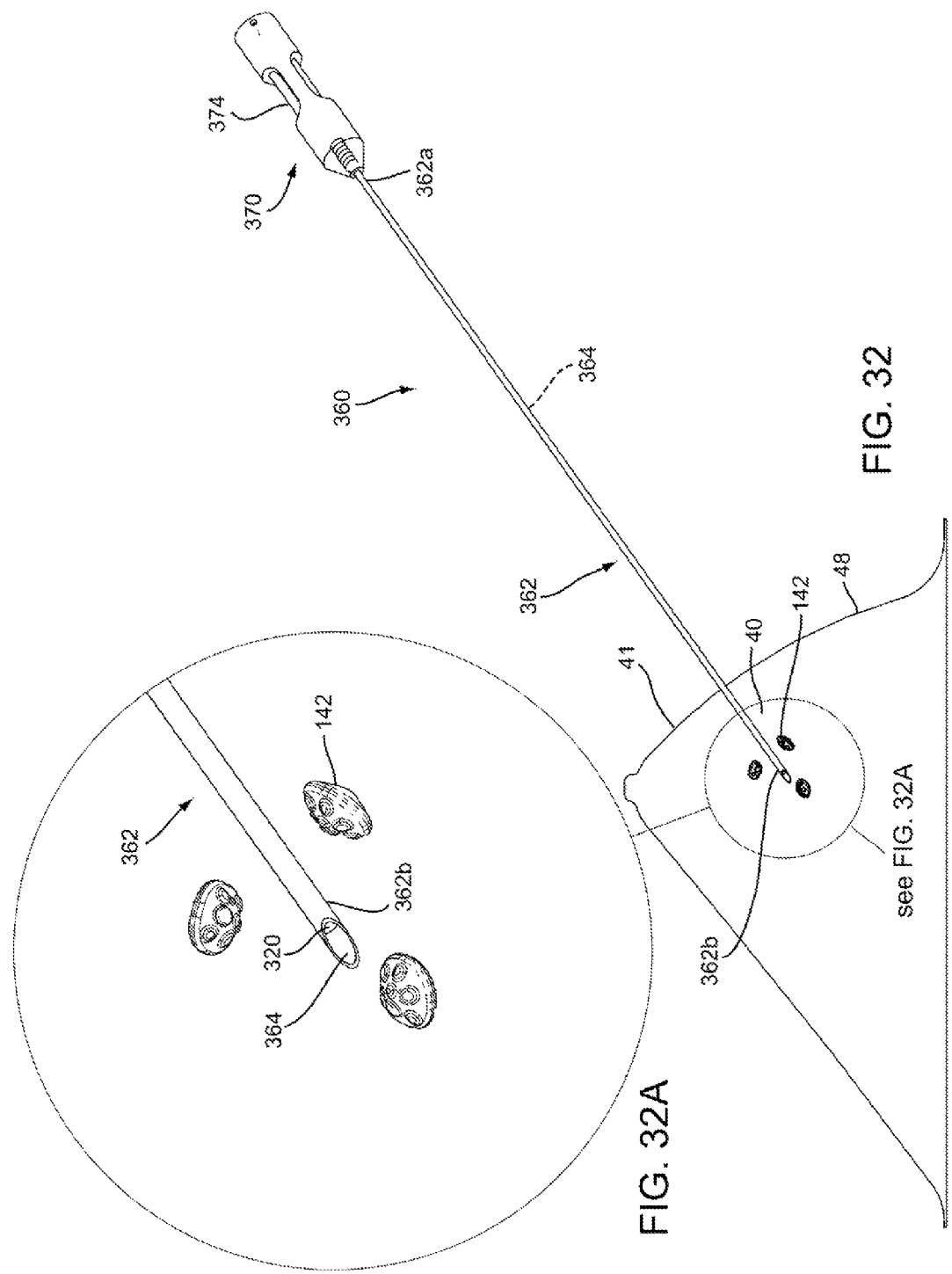

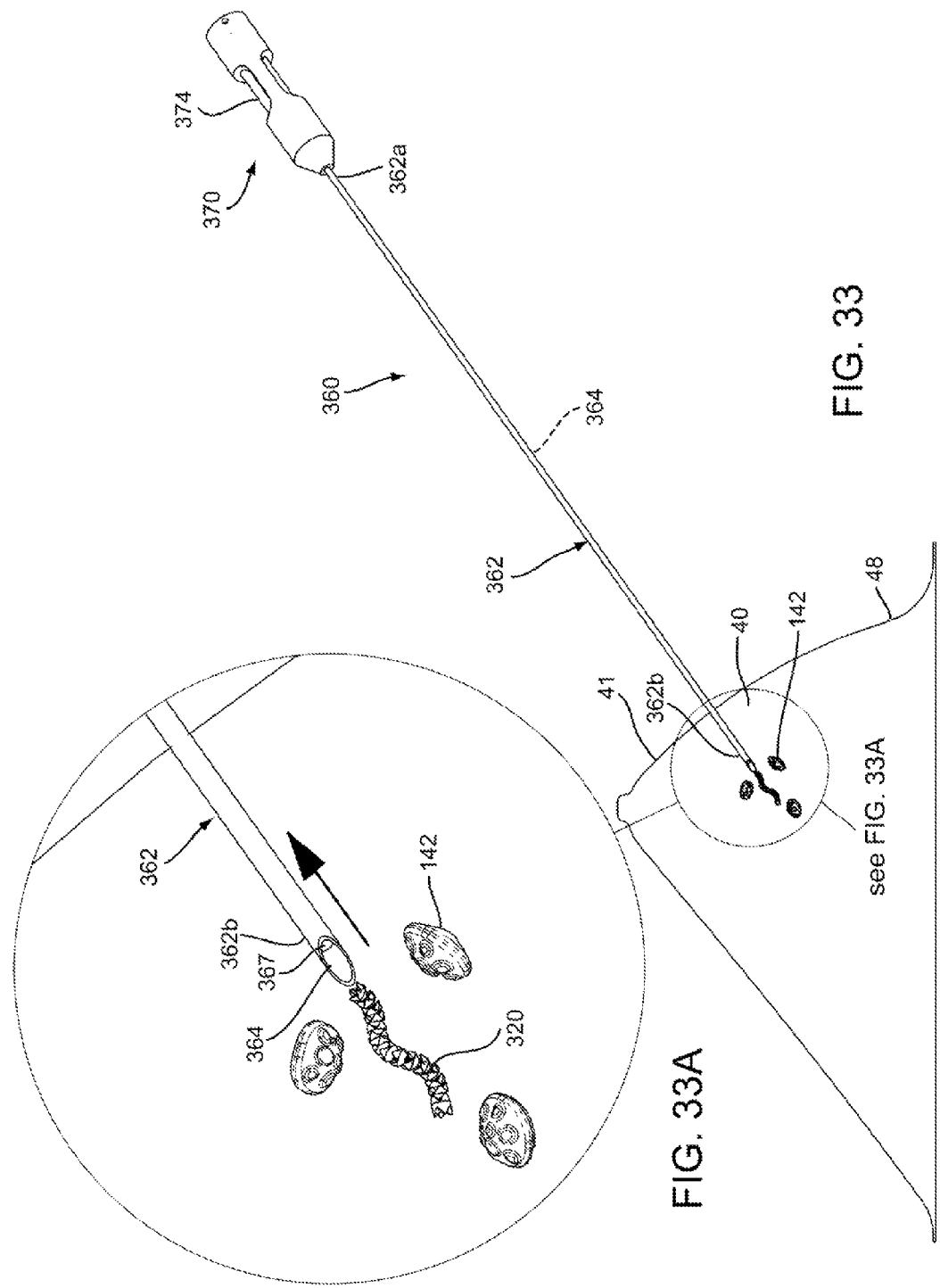

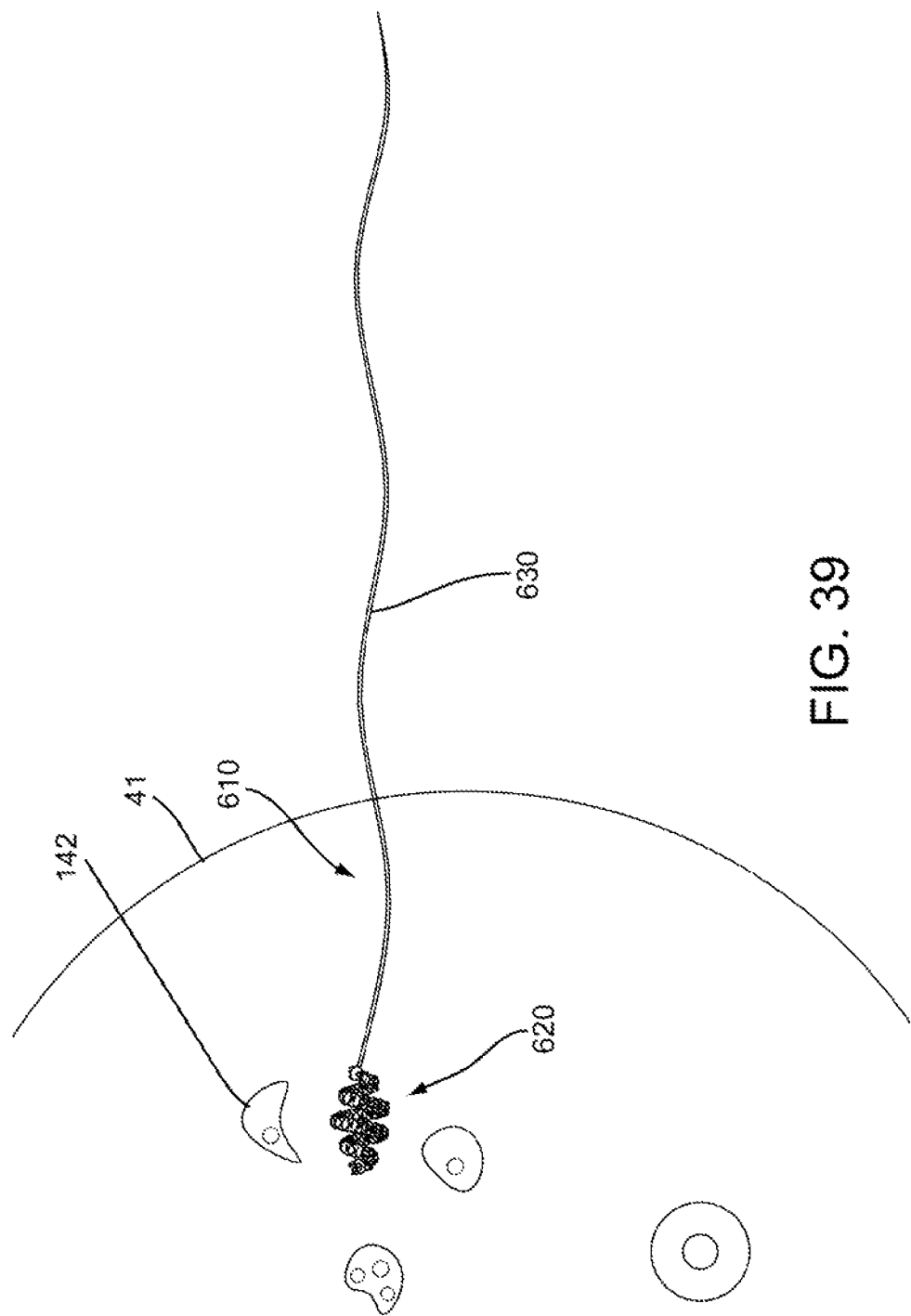

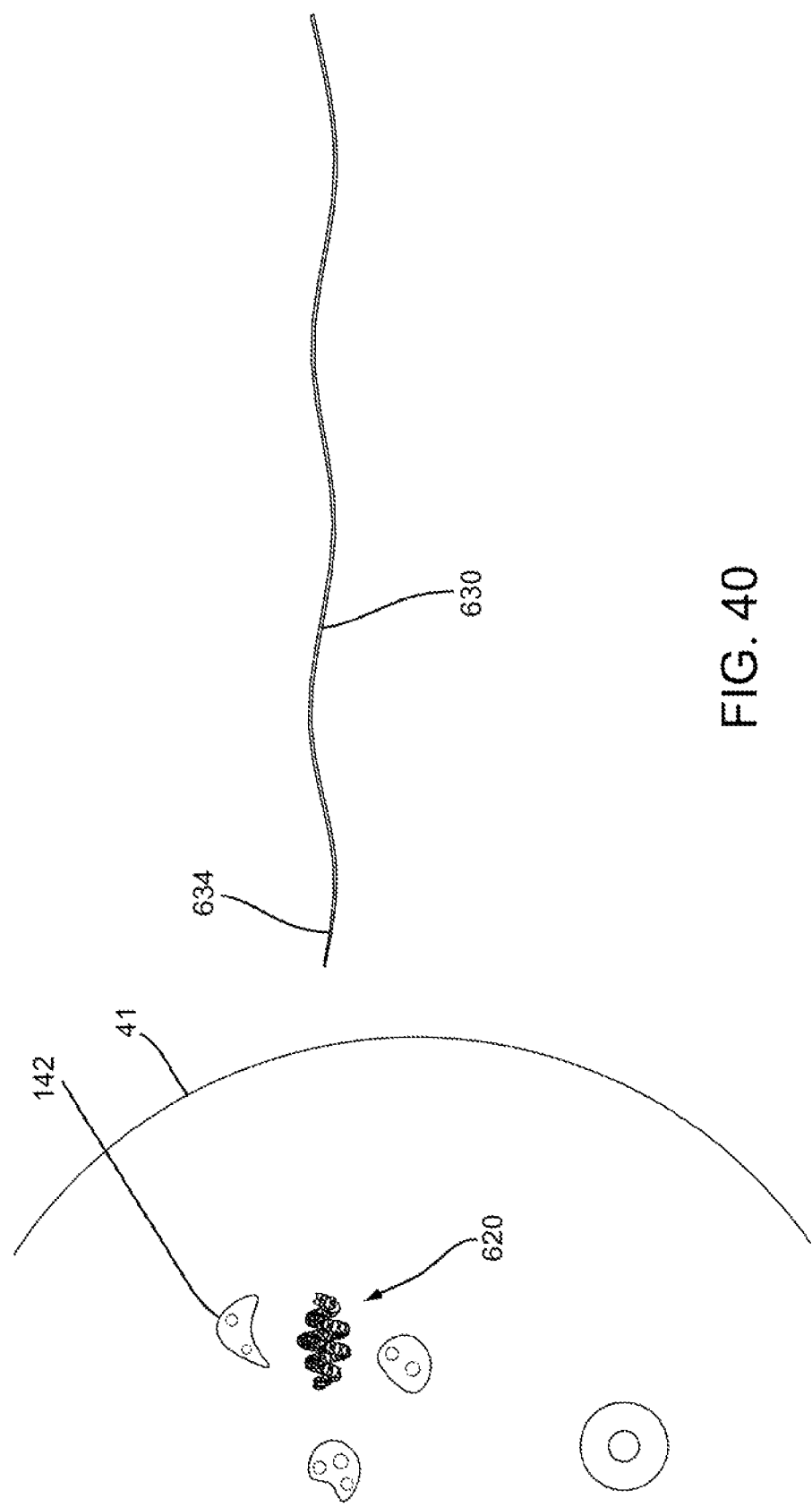

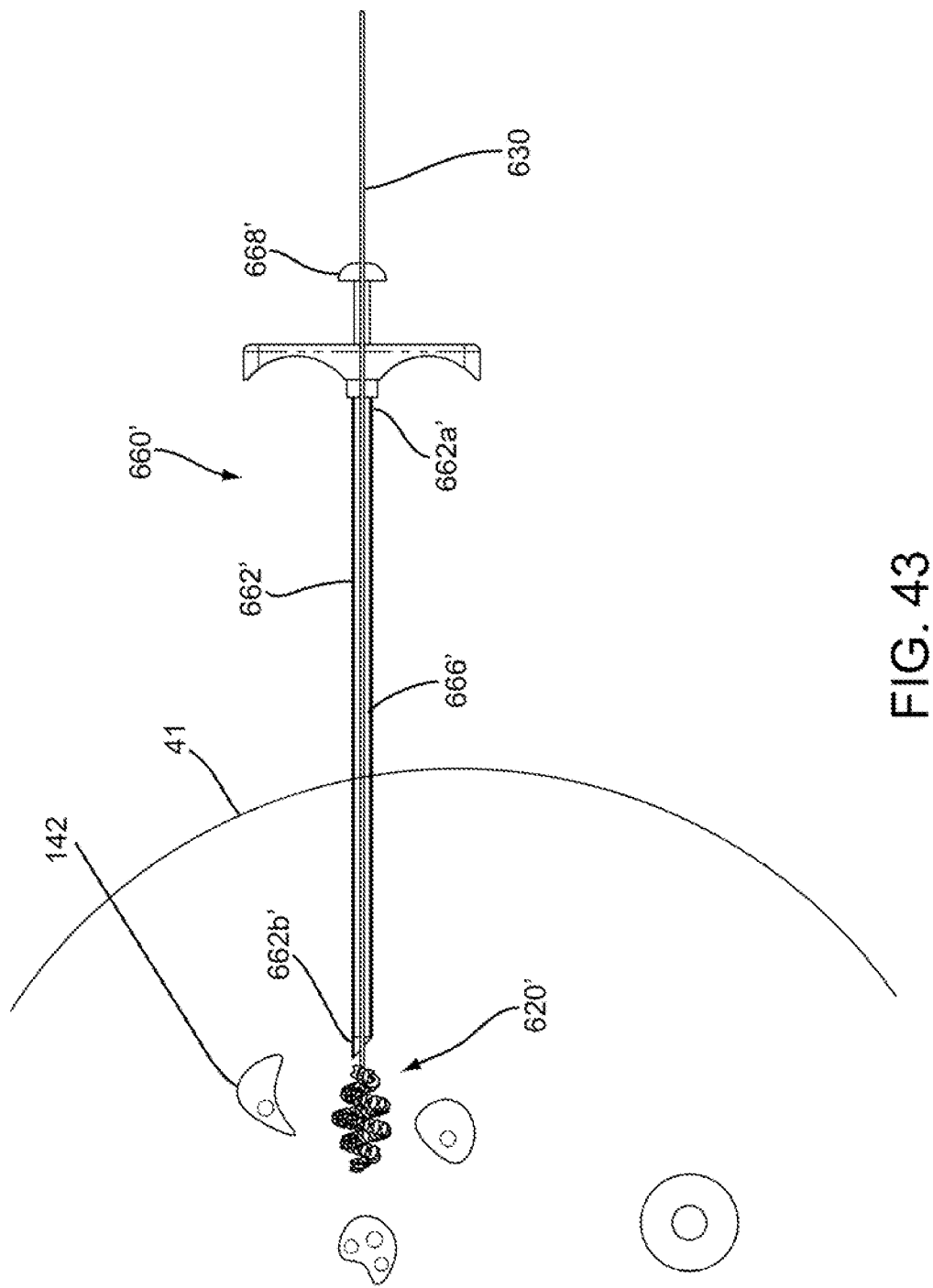

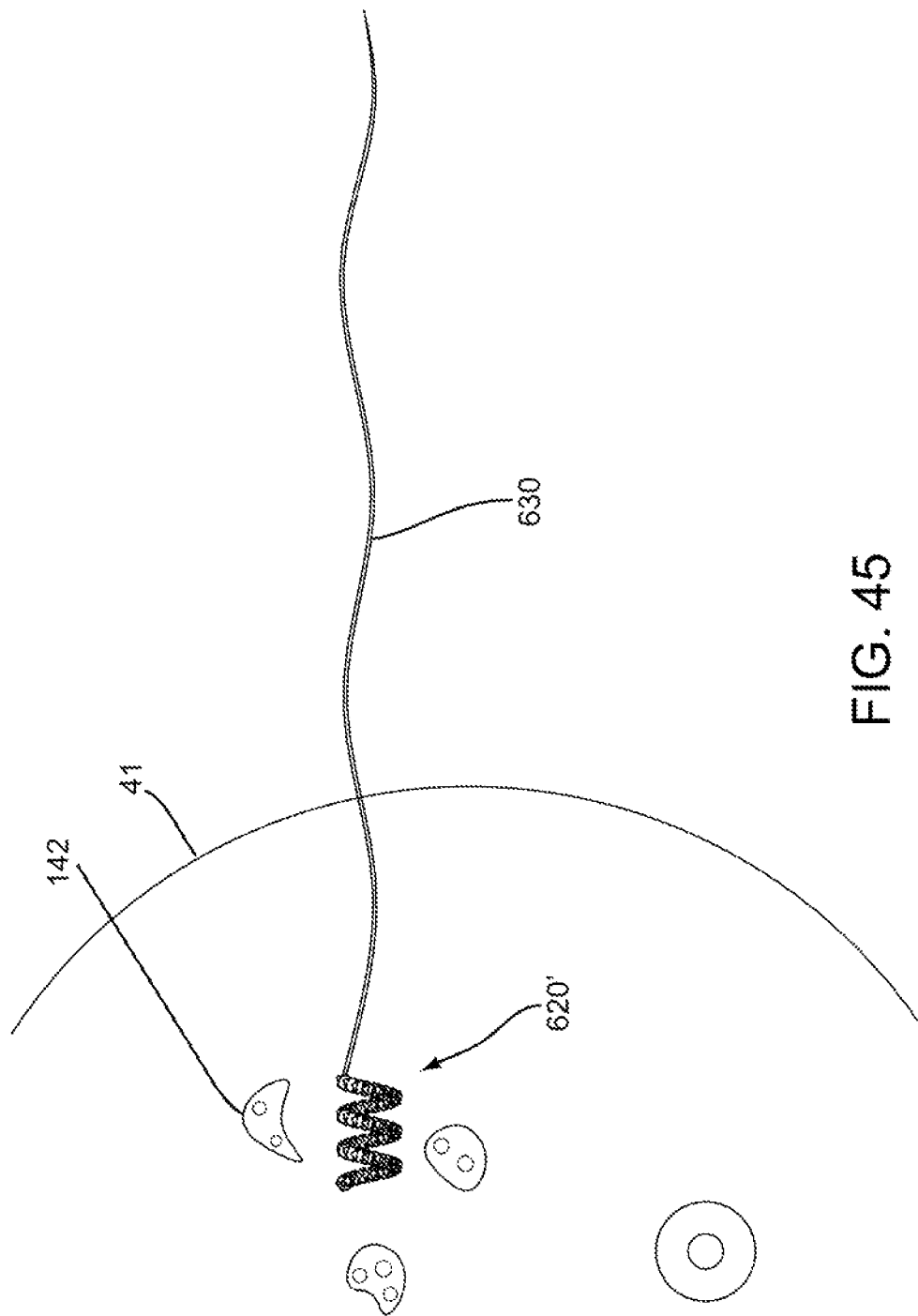

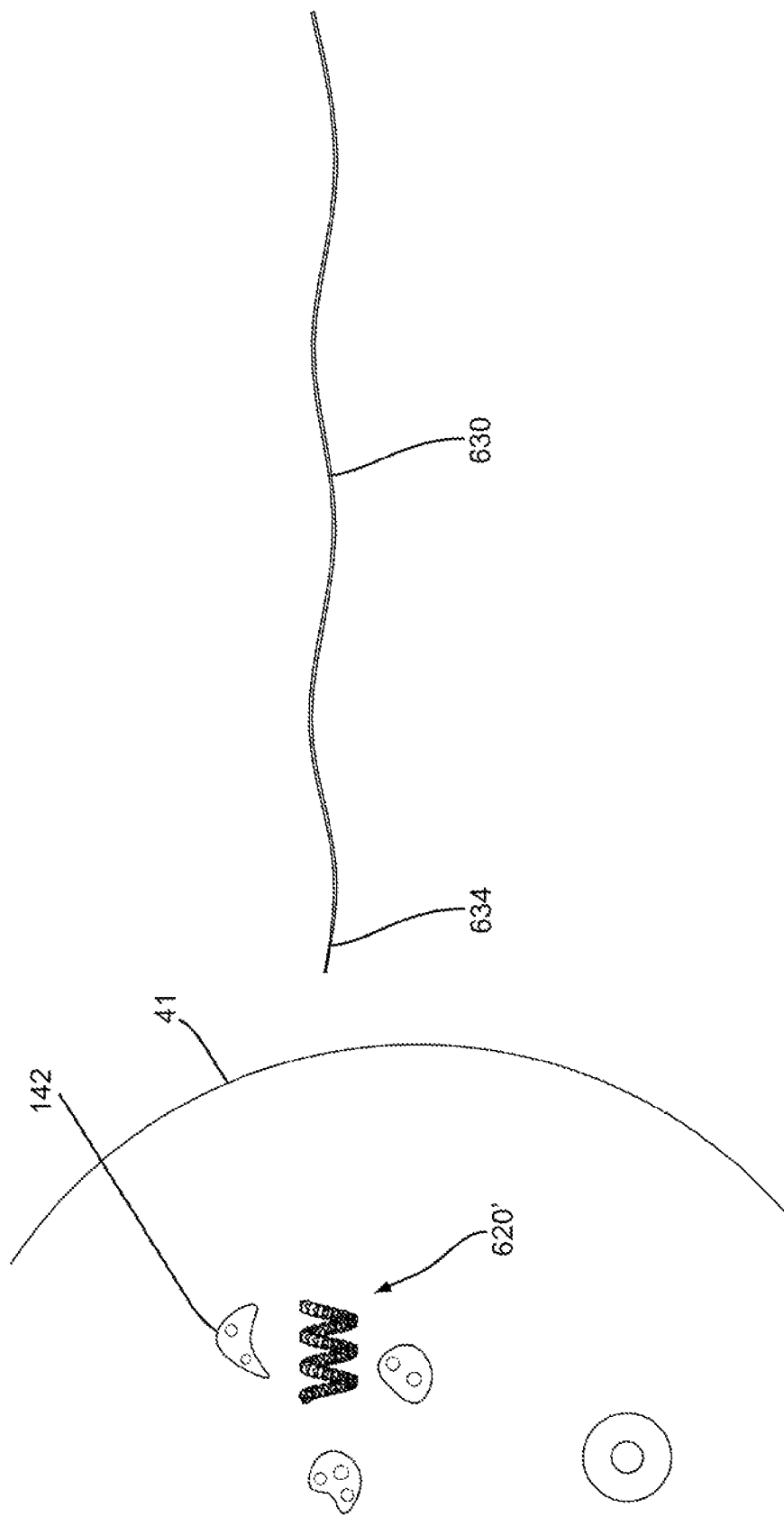

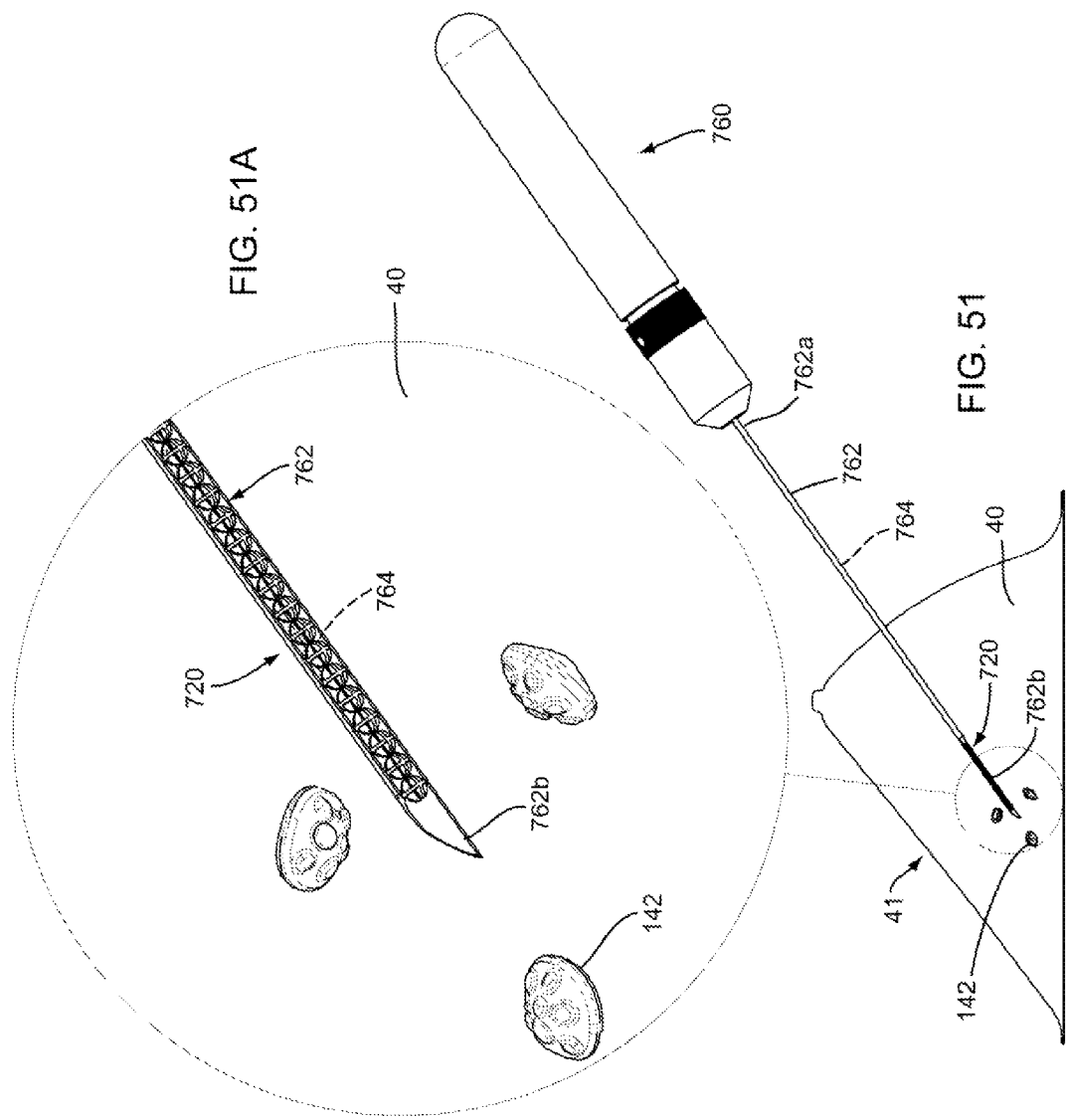

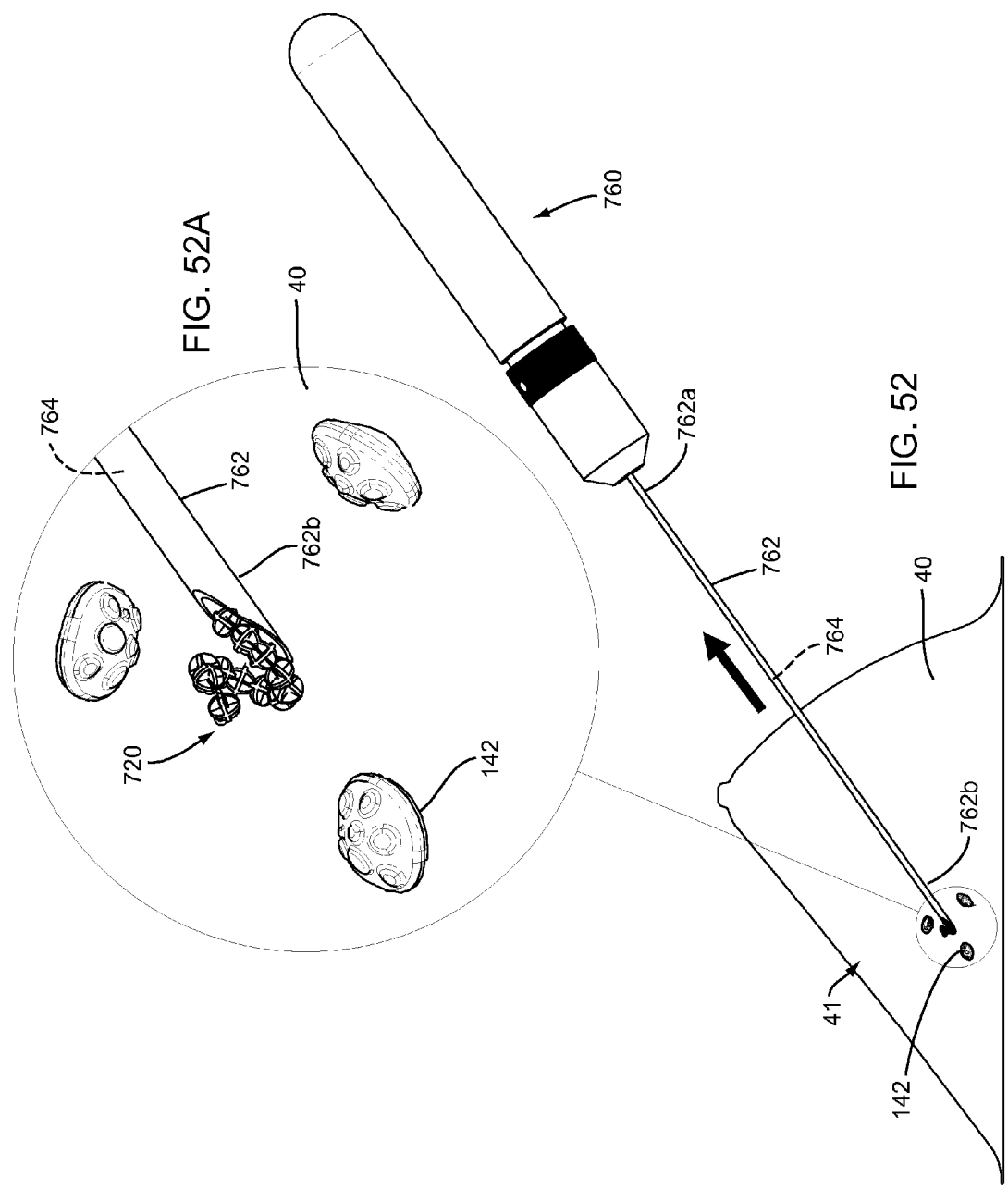

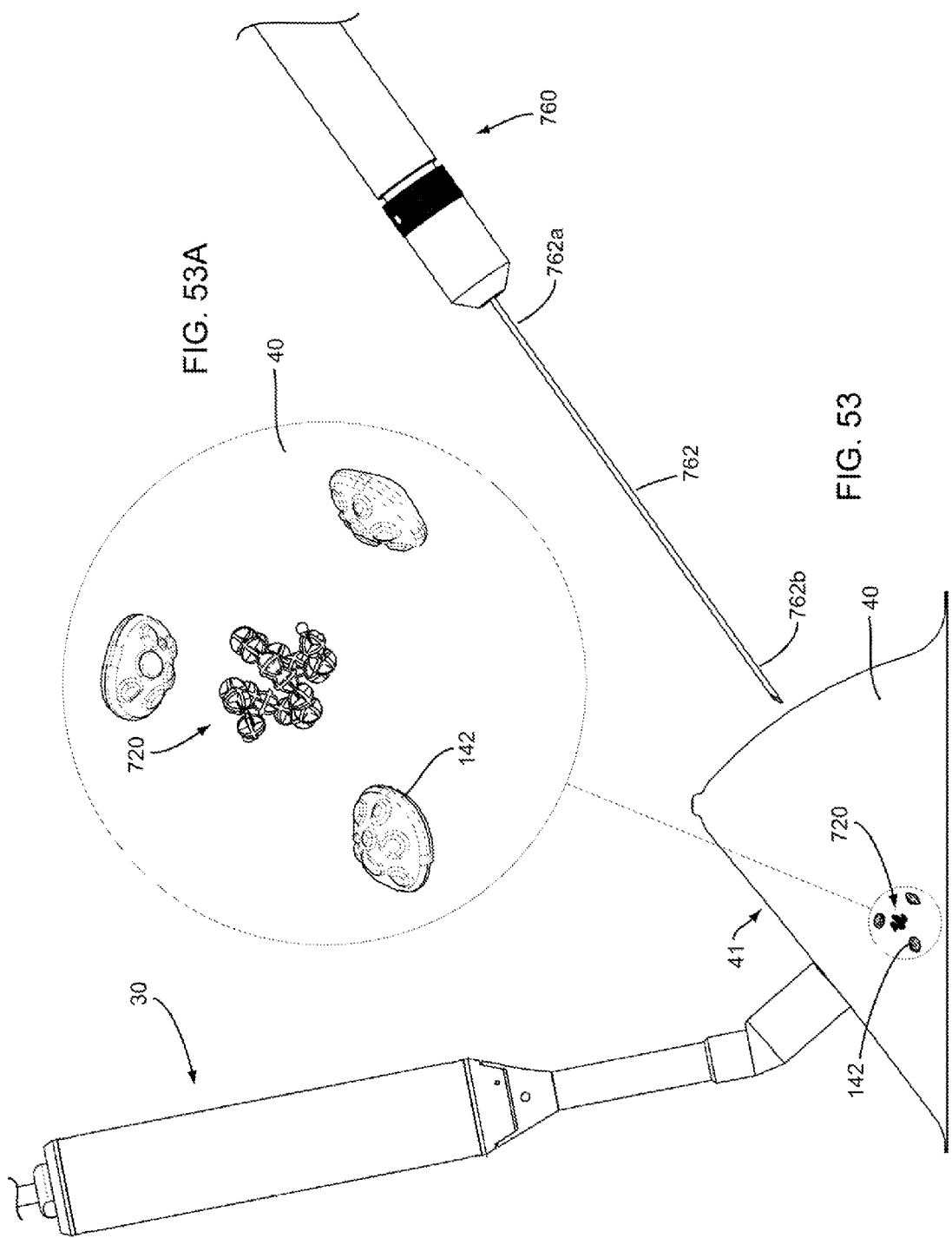

APPARATUS, SYSTEMS, AND METHODS FOR LOCALIZING MARKERS OR TISSUE STRUCTURES WITHIN A BODY

RELATED APPLICATION DATA

This application is a continuation-in-part of co-pending application Ser. No. 12/824,139, filed Jun. 25, 2010, which claims benefit of provisional application Ser. Nos. 61/220,900, filed Jun. 26, 2009, 61/255,469, filed Oct. 27, 2009, and 61/297,694, filed Jan. 22, 2010, the entire disclosures of which are expressly incorporated by reference herein.

FIELD OF THE INVENTION

The present invention relates generally to apparatus and methods for performing surgical procedures, and more particularly to apparatus and methods for localizing targets, markers, lesions, and/or other body structures within a patient's body, e.g., during surgical or other procedures, such as during lumpectomy procedures.

BACKGROUND

Before a biopsy or surgical procedure to remove a lesion within a breast, such as a lumpectomy procedure, the location of the lesion must be identified. For example, mammography or ultrasound imaging may be used to identify and/or confirm the location of the lesion before a procedure. The resulting images may be used by a surgeon during a procedure to identify the location of the lesion and guide the surgeon, e.g., during dissection to access and/or remove the lesion. However, such images are generally two dimensional and therefore provide only limited guidance for localization of the lesion since the breast and any lesion to be removed are three-dimensional structures. Further, such images may provide only limited guidance in determining a proper margin around the lesion, i.e., defining a desired specimen volume to be removed.

To facilitate localization, immediately before a procedure, a wire may be inserted into the breast, e.g., via a needle, such that a tip of the wire is positioned at the location of the lesion. Once the wire is positioned, it may be secured in place, e.g., using a bandage or tape applied to the patient's skin where the wire emerges from the breast. With the wire placed and secured in position, the patient may proceed to surgery, e.g., to have a biopsy or lumpectomy performed.

One problem with using a wire for localization is that the wire may move between the time of placement and the surgical procedure. For example, if the wire is not secured sufficiently, the wire may move relative to the tract used to access the lesion and consequently the tip may misrepresent the location of the lesion. If this occurs, when the location is accessed and tissue removed, the lesion may not be fully removed and/or healthy tissue may be unnecessarily removed. In addition, during the procedure, a surgeon merely estimates the location of the wire tip and lesion, e.g., based on mammograms or other images obtained during wire placement, and may proceed with dissection without any further guidance. Again, since such images are two dimensional, they may provide limited guidance to localize the lesion being treated or removed.

Alternatively, it has been suggested to place a radioactive seed to provide localization during a procedure. For example, a needle may be introduced through a breast into a lesion, and then a seed may be deployed from the needle. The needle may be withdrawn, and the position of the seed may be confirmed using mammography. During a subsequent surgical procedure, a hand-held gamma probe may be placed over the breast to identify a location overlying the seed. An incision may be made and the probe may be used to guide excision of the seed and lesion.

Because the seed is delivered through a needle that is immediately removed, there is risk that the seed may migrate within the patient's body between the time of placement and the surgical procedure. Thus, similar to using a localization wire, the seed may not accurately identify the location of the lesion, particularly, since there is no external way to stabilize the seed once placed. Further, such gamma probes may not provide desired precision in identifying the location of the seed, e.g., in three dimensions, and therefore may only provide limited guidance in localizing a lesion.

Accordingly, apparatus and methods for localization of lesions or other tissue structures in advance of and/or during surgical, diagnostic, or other medical procedures would be useful.

SUMMARY OF THE INVENTION

The present invention is directed to apparatus and methods for performing surgical or other medical procedures. More particularly, the present invention is directed to implantable markers and to apparatus and methods for localizing targets, markers, lesions, and/or other tissue structures within a patient's body during surgical or other medical procedures, e.g., for localizing breast lesions before or during lumpectomy procedures.

In accordance with one embodiment, a system is provided for localization of a target tissue region within a patient's body that includes one or more markers or targets; and a probe for transmitting and receiving electromagnetic signals to detect a target after the target is introduced into a target tissue region and the probe is placed adjacent and/or aimed towards the target tissue region. The probe may include one or more output devices, e.g., a display, speaker, and the like, that provide spatial information based on the spatial relationship of the target relative to the probe, e.g., a distance and/or angular orientation between the probe and the target. Optionally, the system may also include one or more delivery devices for introducing the target(s) into tissue or otherwise into a patient's body, e.g., including a needle, cannula, or other tubular member within which one or more targets may be loaded.

In an exemplary embodiment, the target may include a plurality of angled surfaces, e.g., defining a plurality of dihedral or trihedral corners, that may enhance reflection of the electromagnetic signals from the probe, e.g., such that the target provides a passive marker. For example, the target may be an elongate marker including a plurality of beads coupled to a core element, the beads including angled surfaces and/or edges to enhance detection by the probe. The core element may be biased to one or more predetermined shapes, e.g., a wave shape, a tapered helix, a cylindrical helix, and the like, yet may be sufficiently resilient to be straightened, e.g., to facilitate loading the marker into a delivery device. In another embodiment, the target may include a spherical, elliptical, discus, or other shape, e.g., including one or more surface features to enhance reflection of the electromagnetic signals. In addition, the target may include echogenic features and/or the plurality of angled surfaces on the target may enhance reflection of ultrasound waves, e.g., such that the target provides a passive marker that may be imaged and/or located using external ultrasound imaging and the like.

Optionally, the target may include one or more circuits, features, and the like that modulate an incident signal from the probe to facilitate identification of the target, e.g., such that the target provides an active reflector marker. For example, the target may impose a phase shift on signals from the probe that strike the target, e.g., to distinguish the target from other targets, tissue structures, and the like. In another option, the target may include a circuit and power source such that the target may generate predetermined signals in response to detecting a signal from the probe, e.g., to provide an active transponder marker.

Optionally, the target may include a marker releasably or substantially permanently coupled to an elongate flexible tether. Alternatively, the target may include a localization wire including a shaft and a marker on a distal end of the shaft.

In accordance with another embodiment, a system is provided for localization of a target tissue region within a patient's body that includes a delivery device carrying one or more markers or targets sized for implantation within or around the target tissue region; and a probe for transmitting and receiving electromagnetic signals to detect the one or more markers implanted within or around the target tissue region when the probe is placed adjacent the target tissue region and/or aimed at the target tissue region.

In an exemplary embodiment, the delivery device may include a shaft including a proximal end and a distal end sized for introduction through tissue within a patient's body into a target tissue region, and one or more markers deliverable from the distal end. For example, the shaft may include a lumen and a plurality of markers may be carried within the lumen such that the markers may be delivered sequentially from the shaft and implanted in locations within or around a lesion or other target tissue region. Exemplary markers that may be delivered with the delivery device may include a passive marker, an active reflector marker, and an active transponder marker.

In accordance with still another embodiment, a method is provided for localizing a target tissue region within a patient's body that includes introducing a marker or other target through tissue into the target tissue region; placing a probe against the patient's skin or otherwise adjacent the target tissue region and/or aimed towards the target tissue region; and activating the probe, whereupon the probe transmits electromagnetic signals towards the target tissue region, receives electromagnetic signals reflected from the target, and displays, emits, or otherwise provides spatial information to provide a spatial relationship between the target and the probe.

In one embodiment, the target may be a localization wire introduced through the tissue into the target tissue region, the localization wire carrying the target. In another embodiment, the target may be one or more markers implanted within the target tissue region. In yet another embodiment, the target may be a catheter or other device, e.g., that may be introduced into a target region and deployed to delineate a volume or region. The device may include special features that are configured for locating and/or defining the volume, e.g., using an electromagnetic wave probe. Optionally, the target may be placed before or during a diagnostic, therapeutic, and/or surgical procedure, e.g., using stereotactic, ultrasound, or electromagnetic wave based imaging.

In an exemplary embodiment, the target tissue region may include a region within a patient's breast having a lesion therein, and the target may be delivered into or around the lesion. Alternatively, the target tissue region may be located in other regions of the body, e.g., within or around the intestines, fallopian tubes, and the like. For example, the target may include a first marker that is introduced into the target tissue region spaced apart from a lesion to define a desired margin for removal of a specimen volume from the target tissue region. Optionally, a second marker and/or a plurality of additional markers may be introduced into the target tissue region spaced apart from the lesion and the first marker to further define the desired margin. Thus, if desired, a three dimensional array of markers may be placed within or around the target tissue region to facilitate localization thereof. A tissue specimen may then be removed from the target tissue region, the tissue specimen including the lesion and the target.

In accordance with yet another embodiment, a method is provided for removing a lesion within a target tissue region of a patient's breast that includes introducing a target through breast tissue into the target tissue region; placing a probe adjacent the patient's skin, e.g., oriented generally towards the target tissue region, the probe transmitting electromagnetic signals towards the target tissue region, receiving electromagnetic signals reflected from the target, and providing spatial information to provide a spatial relationship between the target and the probe; and removing a tissue specimen from the target tissue region, the tissue specimen including the lesion and the target.

In accordance with still another embodiment, a method is provided for removing a lesion within a target tissue region of a patient's breast that includes introducing a target through breast tissue into the target tissue region; placing a probe adjacent the patient's skin, e.g., oriented generally towards the target tissue region, the probe transmitting electromagnetic signals towards the target tissue region and receiving electromagnetic signals reflected from the target; using the probe to determine a desired margin within the target tissue region around the lesion; and removing a tissue specimen from the target tissue region, the tissue specimen defined by the desired margin and including the lesion and the target.

In accordance with yet another embodiment, an implantable marker is provided for localization of a target tissue region within a patient's body that includes an elongate core member, and a plurality of beads carried by the core member. Optionally, the beads may include a plurality of surfaces and/or edges, e.g., defining a plurality of dihedral or trihedral corners, to enhance reflection of electromagnetic signals to facilitate identification of the marker. In addition or alternatively, the marker may include an electronic circuit, e.g., embedded in or otherwise carried by one of the beads or the core member, that may provide one of an active reflector and an active transponder. In addition, the marker may include echogenic features and/or the plurality of surfaces and/or edges may enhance reflection of ultrasound waves, e.g., to enhance or otherwise facilitate imaging and/or locating the marker using external ultrasound imaging and the like.

In accordance with still another embodiment, a method is provided for identifying a lesion within a target tissue region of a patient's breast that includes introducing a marker through breast tissue into the target tissue region, and imaging the breast using ultrasound. The marker may include one or more beads and/or a plurality of surfaces and/or edges, e.g., defining dihedral or trihedral corners, that enhance identifying the marker in ultrasound images to facilitate identifying the lesion. In addition or alternatively, the marker may include echogenic materials and/or features for enhancing detection using ultrasound. For example, the target may be an elongate marker including a plurality of beads coupled to a core element, the beads including angled surfaces and/or edges to enhance detection using ultrasound imaging. The core element may be biased to one or more predetermined shapes, e.g., a wave shape, a tapered helix, a cylindrical helix, and the like, yet may be sufficiently resilient to be straightened, e.g., to facilitate loading the marker into a delivery device. In another embodiment, the target may include a spherical, elliptical, discus, or other shape, e.g., including one or more surface features to enhance reflection of ultrasound signals.

Optionally, the method may include removing a tissue specimen from the target tissue region, the tissue specimen including the lesion and the target. The target may enhance locating and/or identifying the lesion and/or desired specimen being removed, e.g., using ultrasound imaging.

Other aspects and features of the present invention will become apparent from consideration of the following description taken in conjunction with the accompanying drawings.

BRIEF DESCRIPTION OF THE DRAWINGS

FIG. 14A is a detail from FIG. 14, showing the probe being used to locate the marker and thereby identify a desired margin for the tissue specimen being removed the breast.

FIG. 15A is a detail from FIG. 15, showing the probe being used to locate the marker and thereby confirm that the desired margin for the removed tissue specimen has been achieved.

FIG. 19A is a detail of a sharpened distal tip of the cannula of FIG. 19 showing the probe therein.

FIG. 23A is a side view of a first exemplary embodiment of an elongate marker that may be implanted into tissue and located using a probe.

FIG. 23B is a cross-sectional view of the marker of FIG. 23A taken along line 23B-23B.

FIG. 23C is an end view of the marker of FIG. 23A.

FIG. 23D is a side view of the marker of FIGS. 23A-23C having a wave shape in its deployed configuration.

FIG. 25A is a side view of an alternative embodiment of an elongate marker that may be implanted into tissue and located using a probe.

FIG. 25B is a detail of the marker of FIG. 24A showing features incorporated into the surface finish of the marker.

FIGS. 26A-26C are side, perspective, and end views, respectively, of another alternative embodiment of an elongate marker having a helical configuration that may be implanted into tissue and located using a probe.

FIGS. 27A-27C are perspective, end, and side views, respectively, of an exemplary embodiment of a spherical marker that may be implanted into tissue and located using a probe.

FIGS. 28A-28C are perspective views of alternative embodiments of a spherical marker that may be implanted into tissue and located using a probe.

FIG. 30A is a side view of another exemplary embodiment of a delivery cannula for delivering a marker.

FIG. 30B is a cross-sectional view of the delivery cannula of FIG. 30A taken along line 30B-30B.

FIG. 31A is a side view of the delivery cannula of FIGS. 30A and 30B after delivering the marker.

FIG. 31B is a cross-sectional view of the delivery cannula of FIG. 31A taken along line 31B-31B.

FIGS. 32 and 33 are cross-sectional views of a breast showing a method for implanting the marker of FIG. 25 into the breast using the delivery cannula of FIGS. 30A-31B.

FIGS. 33A and 33A are details of the marker being implanted in the breast as shown in FIGS. 32 and 33, respectively.

FIGS. 36-40 are cross-sectional views of a breast showing a delivery device for delivering the marker of FIG. 35 and showing a method for introducing the deliver device into the breast to implant the marker adjacent one or more lesions.

FIGS. 43-46 are cross-sectional views of a breast showing a delivery device for delivering the marker of FIG. 42 and showing a method for introducing the deliver device into the breast to implant the marker adjacent one or more lesions.

FIGS. 51-53 are cross-sectional views of a breast, showing a method for implanting a marker, such as the marker of FIGS. 47A and 47B, within a target tissue region within the breast.

FIGS. 51A-53A are details of FIGS. 51-53, respectively.

FIG. 57A is a schematic representation of a signal from a probe striking and reflecting from a marker, while

DETAILED DESCRIPTION OF THE EXEMPLARY EMBODIMENTS

Figure 1:
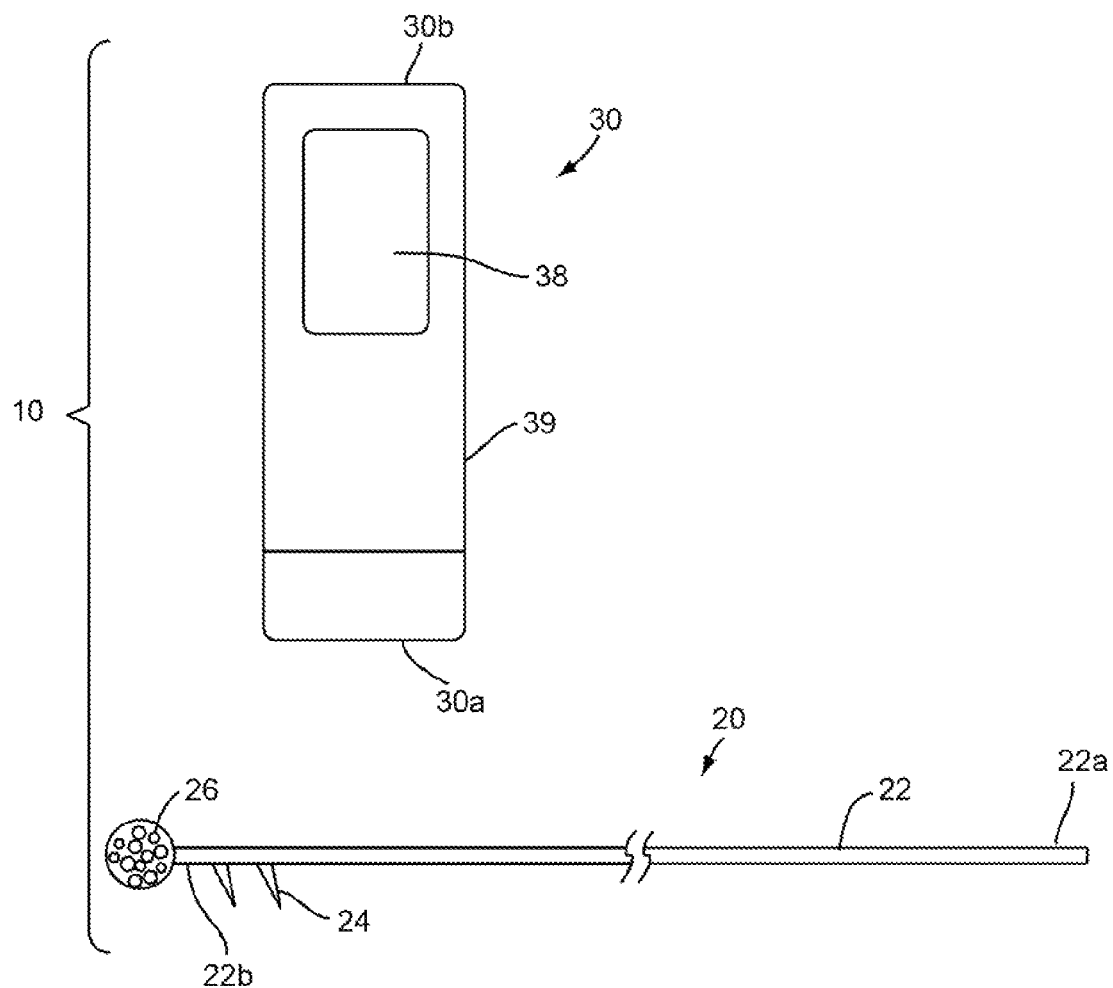
FIG. 1 is a front view of an exemplary embodiment of a system for localizing a target tissue region within a body including a localization wire and a probe.

Turning to the drawings, FIG. 1 shows an exemplary embodiment of a system 10 for localization of a target tissue region within a patient's body, such as a tumor, lesion, or other tissue structure within a breast or other location within a body. The system 10 generally includes a marker device or localization wire 20 and a probe 30 for detecting at least a portion of the localization wire 20 using electromagnetic pulses, waves, or other signals, such as radar. The localization wire 20 may include an elongated member or shaft 22 including a proximal end 22a, a distal end 22b, and a target 26 on the distal end 22b. Optionally, the system 10 may include one or more additional localization wires and/or targets (not shown) in addition to localization wire 20.

The shaft 22 may be formed from a relatively rigid material, e.g., a solid rod or hollow tubular body, having sufficient column strength to facilitate percutaneous introduction of the localization wire 20 through tissue. The shaft 22 may have a length sufficient to extend from a location outside a patient's body through tissue to a target tissue region, e.g., between about half and ten centimeters (0.5-10 cm). Optionally, the shaft 22 may be malleable or otherwise plastically deformable, e.g., such that the shaft 22 may be bent or otherwise formed into a desired shape, if desired.

The target 26 may include one or more features on the distal end 22b of the shaft 22 to facilitate localization of the distal end 22b using the probe 30. In the exemplary embodiment shown, the target 26 may be a bulbous structure, e.g., a sphere having a larger diameter than the distal end 22b of the shaft 22, e.g., between about half and five millimeters (0.5-5 mm). Optionally, the target 26 may include one or more features to enhance reception and/or reflection of electromagnetic signals and/or ultrasound signals. For example, the target 26 may be formed from one or more materials and/or may have a surface finish that enhances detection by radar and/or ultrasound, e.g., similar to the markers described elsewhere herein. In alternative embodiments, other shapes and/or geometries may be provided, e.g., cubes, triangles, helixes, and the like, including one or more corners and/or edges that may enhance radar reflection and/or detection, similar to other embodiments herein.

In addition or alternatively, the target 26 may have a size and/or shape approximating the size and/or shape of the lesion 42, e.g., to facilitate identifying a desired margin around the lesion 42. For example, the size and/or shape of the lesion 42 may be determined in advance, and a target 26 may be selected from a set of different size and/or shape targets and secured to the shaft 22 (or each target may be provided on its own shaft). In addition or alternatively, if multiple localization wires and/or targets are provided, each target may have a different shape and/or features, e.g., to facilitate distinguishing the targets from one another using the probe 30.

In one embodiment, the shaft 22 and target 26 may be integrally formed from the same material. Alternatively, the target 26 may be formed from different material(s) than the shaft 22, and the target 26 may be secured to the distal end 22b, e.g., by bonding with adhesive, welding, soldering, interference fit, threads or other cooperating connectors, and the like. Thus, in this alternative, the target 26 may be formed from material that enhances detection by radar and/or ultrasound relative to the shaft 22.

Optionally, if multiple targets are to be implanted, each target may have a surface, shape, and/or additional material feature that may distinguish a particular target relative to one or more others. For example, each target may absorb or reflect a particular electromagnetic signal that is specific to that target and can be used to uniquely identify it.

In another option, the localization wire 20 may include one or more anchoring elements 24 on the distal end 22b, e.g., adjacent the target 26, although the target 26 itself may stabilize the localization wire 20 sufficiently that anchoring elements 24 may be unnecessary. As shown, the anchoring elements 24 include a plurality of barbs 24 (two shown) that extend transversely from the shaft 22, e.g., angled proximally away from the target 26. Thus, the barbs 24 may be configured for anchoring the localization wire 20 in position after the localization wire 20 is inserted into tissue, e.g., allowing the localization wire 20 to be advanced distally through tissue while preventing subsequent proximal withdrawal. For example, the barbs 24 may be sufficiently flexible such that the barbs 24 may be compressed against or otherwise adjacent the shaft 22, e.g., to minimize a profile of the localization wire 20 to facilitate advancement, yet resiliently biased to return outwardly to a transverse orientation, as shown.

The probe 30 may be a portable device having electromagnetic signal emitting and receiving capabilities, e.g., a micropower impulse radar (MIR) probe. For example, as shown in FIG. 1, the probe 30 may be a handheld device including a first end 30a intended to be placed against or adjacent tissue, e.g., a patient's skin or underlying tissue, and a second opposite end 30b, e.g., which may be held by a user. Alternatively, the probe 30 may include a portable device (either a stand-alone device, or a probe coupled to other supporting equipment, not shown) having ultrasound emitting and receiving capabilities, e.g., similar to conventional ultrasound imaging devices.

Figure 10:
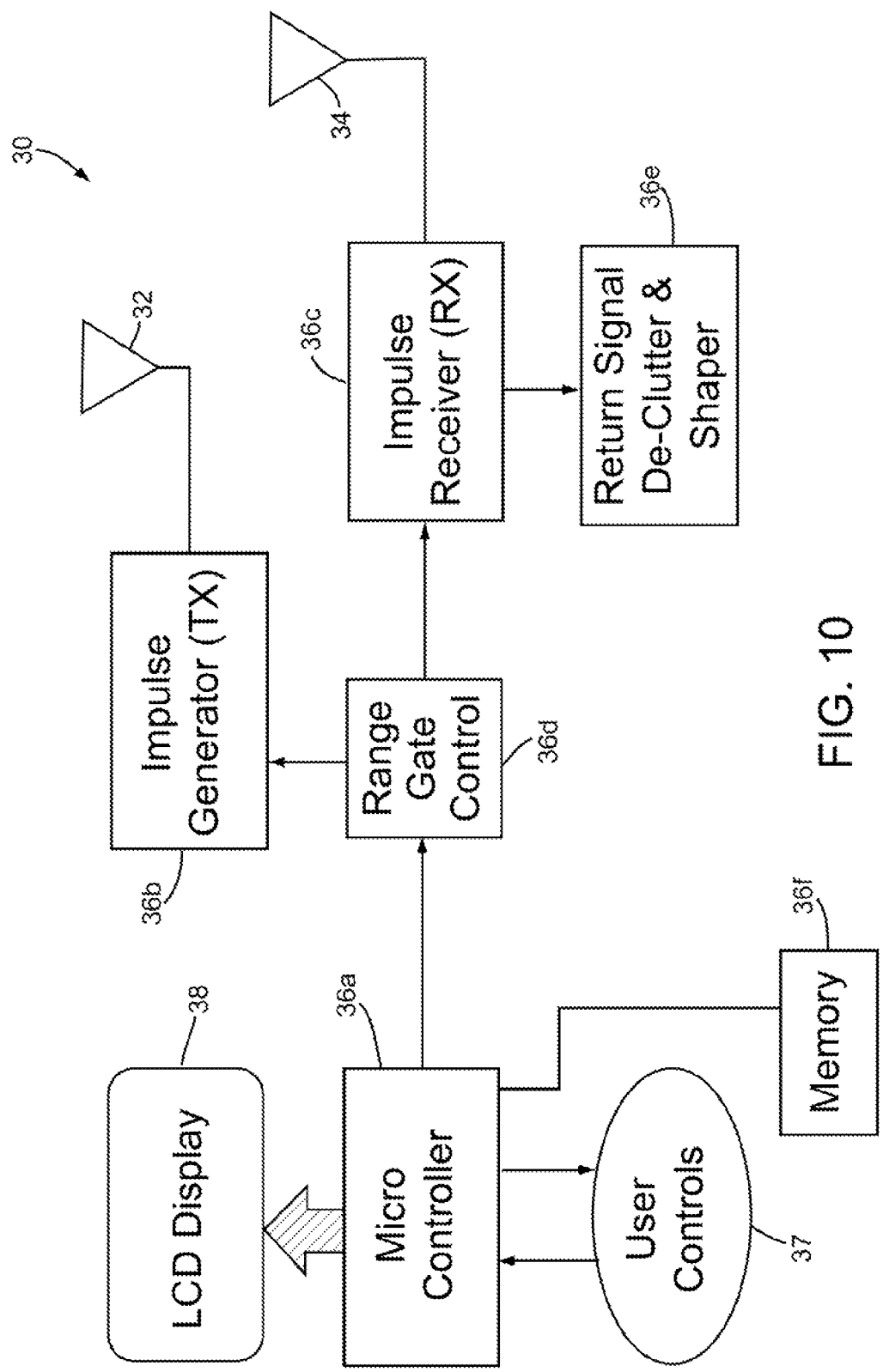
FIG. 10 is a schematic showing an exemplary embodiment of a probe that may be included in various systems for localizing markers.

With additional reference to FIG. 10, the probe 30 generally includes one or more antennas, e.g., a transmit antenna 32 and a receive antenna 34, one or more processors or controllers 36, and a display 38. The processor 36 may include one or more controllers, circuits, signal generators, gates, and the like (not shown) needed to generate signals for transmission by the transmit antenna 32 and/or to process signals received from the receive antenna 34. The components of the processor 36 may include discrete components, solid state devices, programmable devices, software components, and the like, as desired.

For example, as shown, the probe 30 may include an impulse generator 36b, e.g., a pulse generator and/or pseudo noise generator (not shown), coupled to the transmit antenna 32 to generate transmit signals, and an impulse receiver 36c for receiving signals detected by the receive antenna 34. The processor 36 may include a micro controller 36a and a range gate control 36d that alternately activate the impulse generator 36b and impulse receiver 36c to transmit electromagnetic pulses, waves, or other signals via the antenna 32, and then receive any reflected electromagnetic signals via antenna 34. Exemplary signals that may be used include microwave, radio waves, such as micro-impulse radar signals, e.g., in the Ultra Low bandwidth region.

In exemplary embodiments, each of the antennas 32, 34 may be a UWB antenna, e.g., a horn obtrusive physical profile, a dipole and patch, or a co-planar antenna, such as a diamond dipole antenna, a single ended elliptical antenna ("SEA"), a patch antenna, and the like. Alternatively, the processor 36 may activate a single antenna to operate alternately as a transmit antenna and a receive antenna (not shown) instead of providing separate antennas 32, 34.

For example, each antenna 32, 34 may be a TEM horn antenna, such as that disclosed in "TEM Horn Antenna for Ultra-Wide Band Microwave Breast Imaging," published in Progress in Electromagnetics Research B, Vol. 13, 59-74 (2009), the entire disclosure of which is expressly incorporated by reference herein. Alternatively, each antenna 32, 34 may be a patch antenna, such as those disclosed in U.S. Publication No. 2008/0071169, published Mar. 20, 2008, and in "Wideband Microstrip Patch Antenna Design for Breast Cancer Tumour Detection," by Nilavalan, et al., published in Microwaves, Antennas, & Propagation, IET, Volume 1, Issue 2 (April 2007), pp. 277-281, the entire disclosures of which are expressly incorporated by reference herein. The patch antenna may be coupled to an enclosure (not shown), e.g., filled with dielectric material, to facilitate use with micro-impulse radar.

Figure 10A:
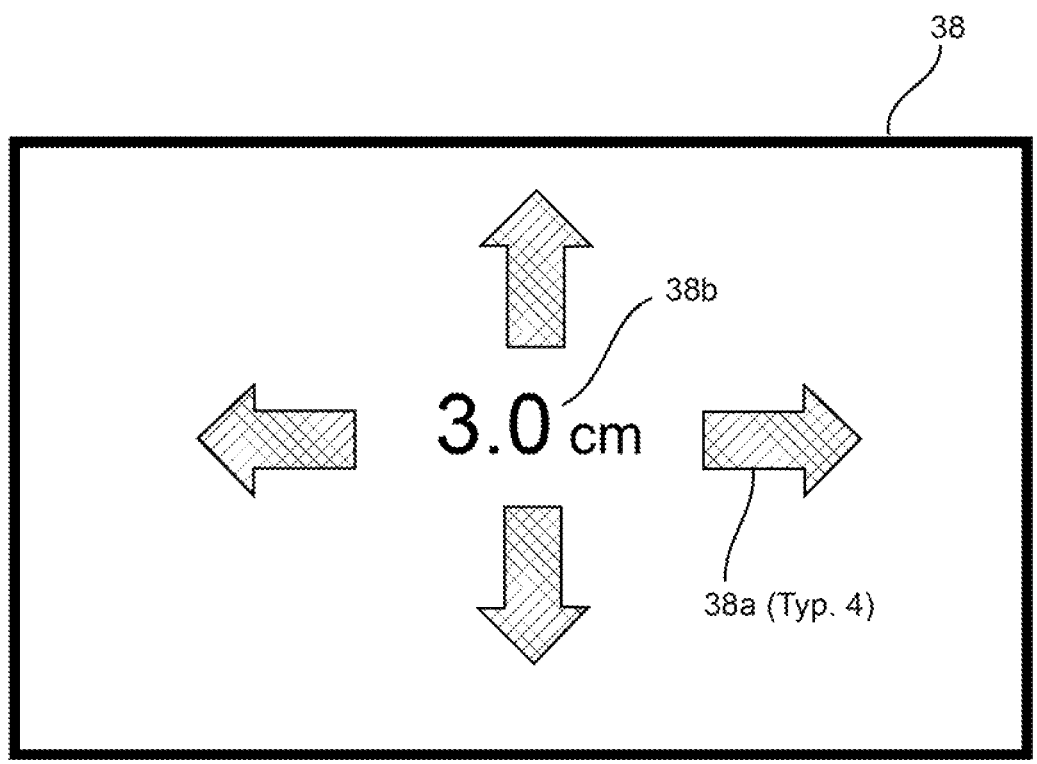
FIG. 10A is an exemplary display output that may be provided on a probe, such as the probe instrument shown in FIG. 10.
Figure 10B:
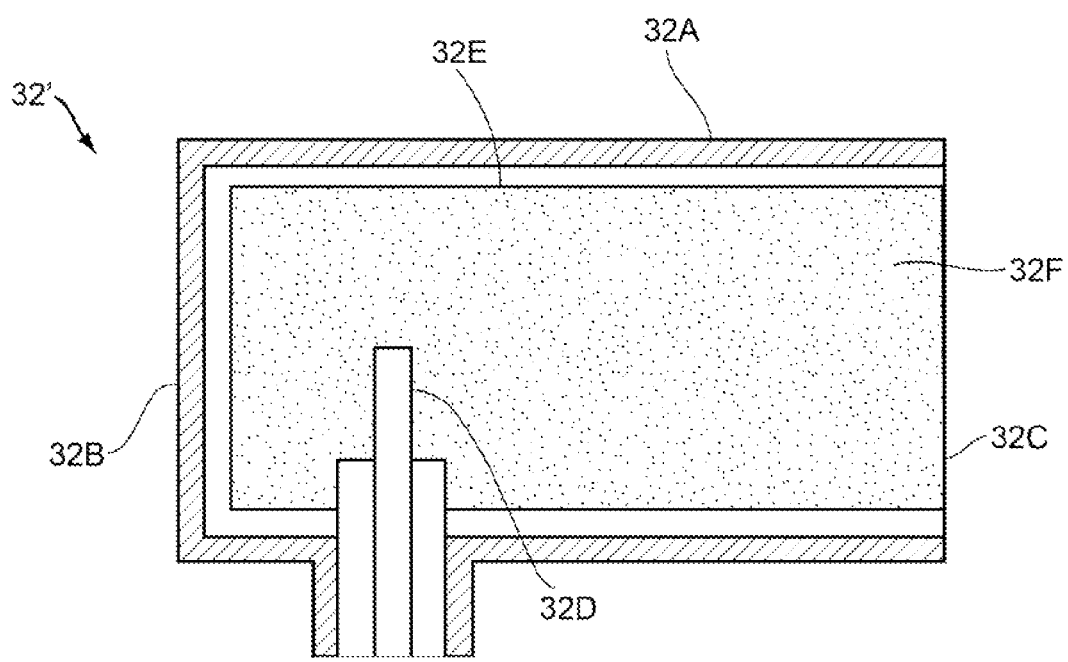
FIG. 10B is a cross-sectional view of an antenna that may be provided in a probe, such as that shown in FIG. 10.

In another alternative embodiment, each antenna may be a waveguide horn, e.g., as shown in FIG. 10B. As shown, antenna 32' includes a casing 32A that is closed on a first end 32B, and open on a second end 32C, and within which a waveguide 32D is mounted. The walls of the casing 32A may be lined with an absorber material 32E, e.g., a broadband silicone absorber material, such as Eccosorb-FGM40, sold by Emerson & Cuming Microwave Products N.V. of Westerlo, Belgium. The volume within the casing 32A may be filled with a dielectric 32F, e.g., having a relative permittivity of 10. In an exemplary embodiment, the antenna 32' may be a square waveguide horn configured to operate at ultrawide band frequencies ("UWB") between about three and ten Gigahertz (3-10 GHz), e.g., having a width of about fifteen by fifteen millimeters (15×15 mm), and a length between the first and second ends 32B-32C of about thirty millimeters (30 mm). The open end 32B may be oriented outwardly from a probe within which the antenna 32' is mounted, e.g., such that the open end 32B may contact or otherwise be coupled with tissue through which the antenna 32' is intended to transmit and/or receive signals, as described elsewhere herein.

The signals from the impulse receiver 36c may be filtered or otherwise processed, e.g., by a return signal de-clutter and shaper circuit 36e, before being communicated to the micro-controller 36a for further processing, display, storage, transmission, and the like. The circuit 36e may receive signals from the antenna 34, e.g., return echo noise and clutter, may de-clutter the signals, e.g., using LPF, and/or may include digital adaptive filtering and/or pulse shapers, as desired. The micro-controller 36a may then interpret the received and/or processed signals to identify a spatial relationship, e.g., distance, angle, orientation, and the like, of the target 26 or other structures relative to the probe 30, as described further below. Exemplary embodiments of processors and/or other components that may be included in the probe 30 are disclosed in U.S. Pat. Nos. 5,573,012 and 5,766,208, issued to McEwan, the disclosures of which are fully and expressly incorporated by reference herein.

In an alternative embodiment, the probe 30 may be configured to operate as a magneto-radar system, such as that disclosed in U.S. Pat. No. 6,914,552, issued to McEwan, the entire disclosure of which is expressly incorporated by reference herein. For example, the probe 30 may include a magnetic field excitation source, e.g., an electromagnet (not shown), coupled to a generator and/or current coil driver (not shown), which may be provided within or external to the probe 30. For example, the probe may induce a magnetic field to a marker or other target, generating a pole to pole vibration at a specific frequency that the radar unit may identify and/or recognize to provide a distance measurement or location coordinates. Such a probe may be useful when the target is implanted in tissue, bone, or bodily fluid with a relatively high impedance or dielectric constant that may attenuate the radar pulse from reaching the target or the reflected signal from reaching the radar antenna.

Returning to FIG. 10, the probe's display 38 may be coupled to the micro-controller 36a for displaying information to a user of the probe 30, e.g., spatial or image data obtained via the antenna(s) 32, 34. For example, the display 38 may simply be a readout providing distance, angle, orientation, and/or other data based on predetermined criteria, e.g., based on the relative location of the target 26 to the probe 30, as described further below. FIG. 10A shows an exemplary embodiment of an output for display 38 that may be provided, which may include an array of arrows or other indicators 38a and a distance readout 38b. For example, the micro-controller 36a may analyze the received signals to determine in which direction relative to the probe 30 a marker (not shown) may be located and activate the appropriate arrow 38a, and display a distance (e.g., "3 cm" shown) to the marker. Thus, the user may be able to identify in what direction and how far in that direction the marker is located, thereby providing the user guidance towards the marker and the target tissue region within which the marker is implanted.

In addition or alternatively, the display 38 may provide other information, e.g., real-time images of the region towards which the probe 30 is oriented, i.e., beyond the first end 30a, operational parameters of the probe 30, and the like. Optionally, the probe 30 may include one or more other output devices in addition to or instead of the display 38. For example, the probe may include one or more speakers (not shown) that may provide audio output, one or more LEDs or other light sources that provide visual output, and the like e.g., to provide information such as spatial information, operation parameters, and the like. For example, a speaker or LED may be activated when the probe 30 reaches a predetermined threshold distance from the marker, e.g., a desired margin, or may be activated when successively closer distances are achieved.

Optionally, the probe 30 may include other features or components, such as one or more user interfaces, memory, transmitters, receivers, connectors, cables, power sources, and the like (not shown). For example, the probe 30 may include one or more batteries or other internal power sources for operating the components of the probe 30. Alternatively, the probe 30 may include a cable (not shown) that may be coupled to an external power source, e.g., standard AC power, for operating the components of the probe 30.

Returning to FIG. 10, the user controls 37 may include one or more input devices, such as a keypad, touch screen, individual buttons, and the like (not shown). The user controls 37 may allow the user to perform simple operations, e.g., turn the probe 30 on and off, reset the probe 30, and the like, or may allow more complicated control of the probe 30. For example, the user controls 37 may allow the sensitivity or other parameters of the probe 30 to be adjusted, may allow data to be captured, stored, transmitted remotely, and the like.

Optionally, the probe 30 may include internal memory 36f that may record or otherwise store data obtained via the antenna(s) 32, 34 and/or micro-controller 36a. For example, the micro-controller 36a may automatically record data during operation, or may be instructed to selectively save data to the memory 36f. In addition or alternatively, the micro-controller 36a may transfer data to one or more external devices, e.g., for storage, display, and the like. For example, the probe 30 may include one or more cables (not shown) to allow such data transfer and/or the probe 30 may include a transmitter and/or receiver (not shown) for wirelessly transferring data and/or receiving commands, e.g., via radio frequency, infrared, or other signals.

As shown in FIGS. 1 and 10, all of the internal components of the probe 30 may be provided in a housing or casing 39 such that the probe 30 is self-contained. For example, the casing 39 may be relatively small and portable, e.g., such that the entire probe 30 may be held in a user's hand. Optionally, as shown in FIG. 1, the first end 30a of the casing 39 may be formed from like or different materials than other portions of the casing 39. For example, the first end 30a may be formed from materials that easily accommodate passage of electromagnetic signals therethrough, e.g., from the transmit antenna 32 and/or to the receive antenna 34, without substantial interference. Optionally, the materials may be selected to reduce interference, match impedance, or otherwise facilitate transmitting and receiving signals via the probe 30 into and out of a patient's body. In addition or alternatively, if desired, the probe 30 may include a handle, finger grips, and/or other features (not shown) to facilitate holding or otherwise manipulating the probe 30.

Figure 11:
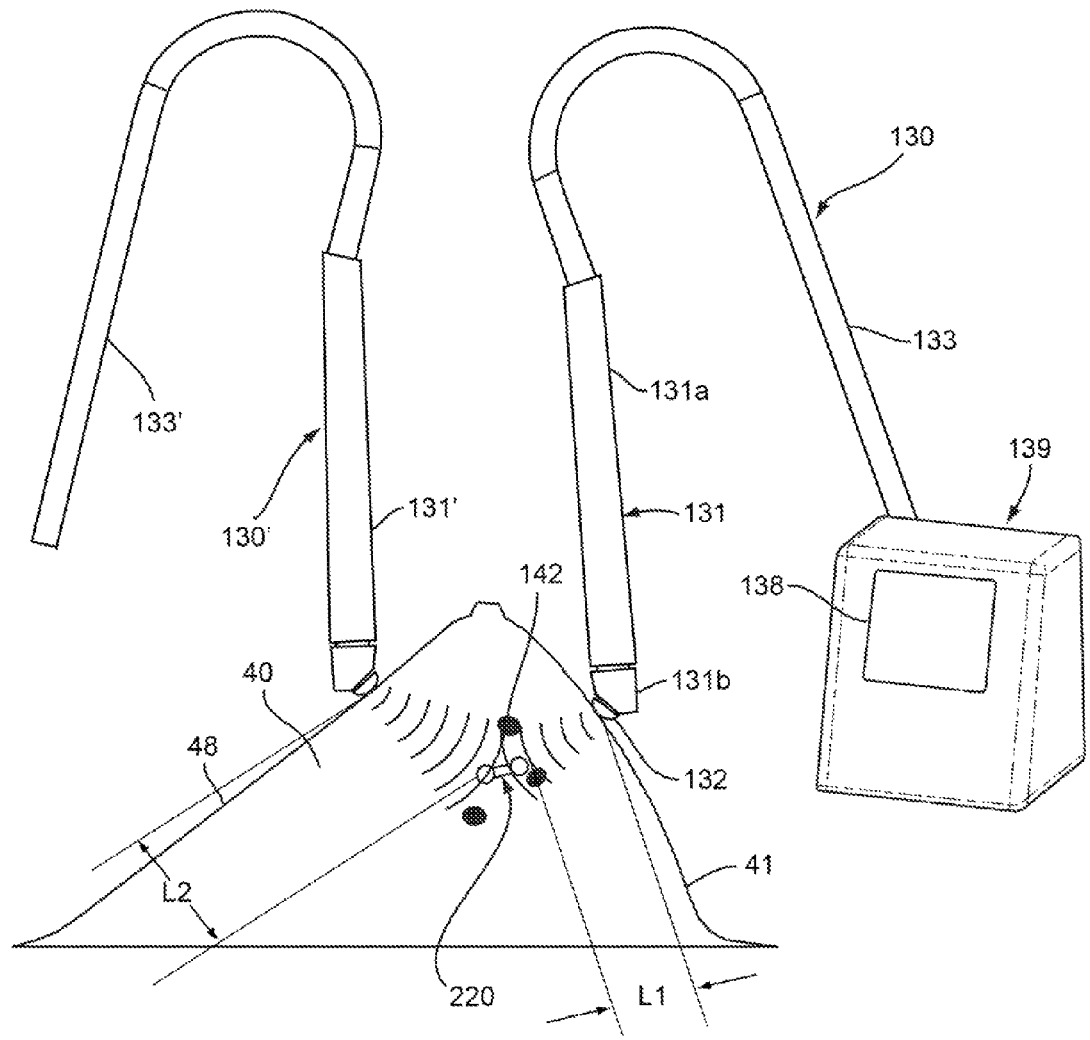
FIG. 11 shows another exemplary embodiment of a system for localizing a target tissue region within a body including a marker implanted in a breast and a probe instrument including a handheld probe for locating the marker and a controller coupled to the probe.

Alternatively, as shown in FIG. 11, a probe instrument 130 may be provided that includes a separate controller 139 including one or more of the components within a casing remote from a handheld probe 131. For example, the handheld probe 131 may include an elongate housing 131a including a tip 131b with one or more antennas 132. The controller 139 may include one or more processors for controlling the antenna(s) 132, a display 138, and the like, similar to the previous embodiments. The handheld probe 131 may be coupled to the processor(s) in the controller 139 by one or more cables 133. For example, an impulse generator, impulse receiver, and/or gate control may be provided within the casing of the controller 139 or, optionally, within the housing 131a, if desired. In one embodiment, the cable 133 may be removably connectable to a connector (not shown) on the controller 139 for electrically coupling the antenna 132 of the handheld probe 131 to the electronics within the controller 139. Thus, the handheld probe 131 may be a disposable, single-use device while the controller 139 may be used during multiple procedures by connecting a new handheld probe 131 to the controller 139, which may remain out of the surgical field yet remain accessible and/or visible, as desired, as explained further below.

Turning to FIGS. 2A-5, the localization system 10 of FIG. 1 may be used during a medical procedure, for example, in a breast biopsy or lumpectomy procedure, e.g., to facilitate localization of a lesion or other target tissue region 42 and/or to facilitate dissection and/or removal of a specimen from a breast 41 or other body structure. It should be noted that, although the system 10 is described as being particularly useful in localization of breast lesions, the system 10 can also be used in localization of other objects in other areas of the body, e.g., as described elsewhere herein.

Figure 2A:
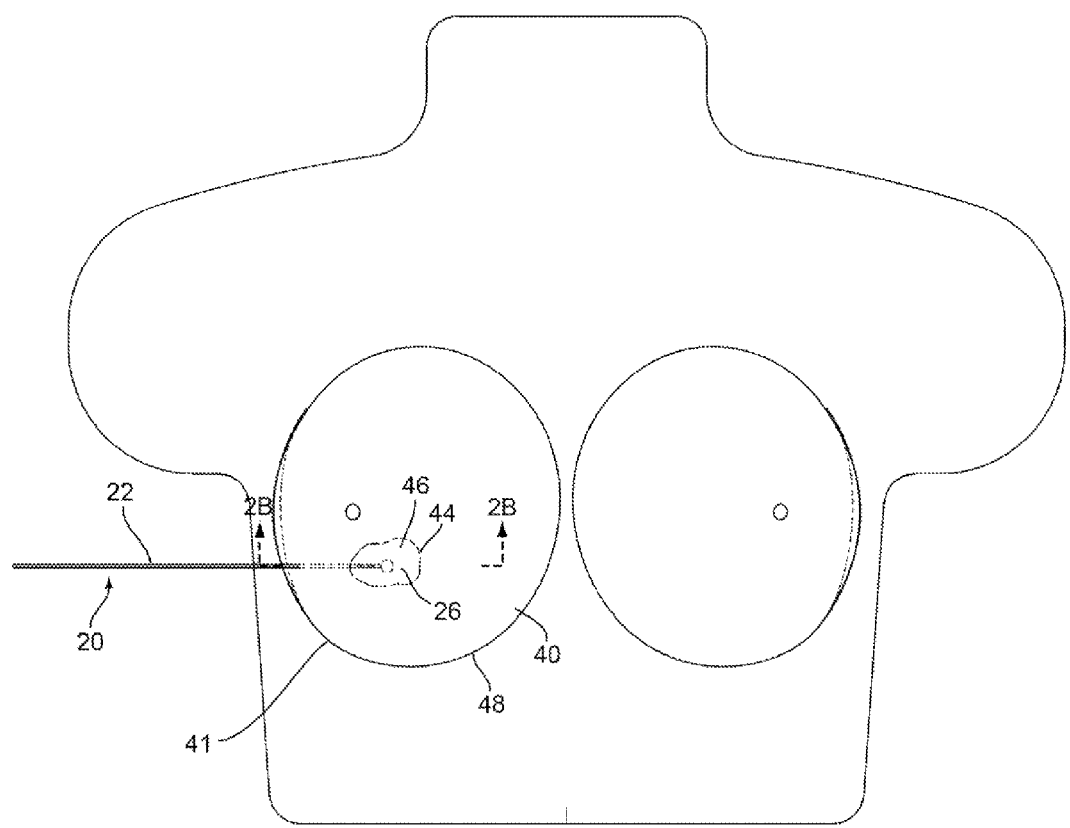
FIG. 2A is a front elevation view of a torso of a patient's body, showing the localization wire of FIG. 1 being inserted into a target tissue region within a breast, e.g., a tumor or other lesion.

Before the procedure, a target tissue region, e.g., a tumor or other lesion, may be identified using conventional methods. For example, as shown in FIG. 2A, a lesion 42 within a breast 41 may be identified, e.g., using mammography and/or other imaging, and a decision may be made to remove the lesion 42. The dashed line 44 surrounding the tumor 42 defines a "clear" margin, e.g., indicating the size and shape of a desired tissue specimen 46 that is to be removed during the procedure. For example, the margin 44 may be selected to ensure that the remaining tissue after removing the specimen 46 is substantially clear of cancerous or other undesired cells. In an exemplary embodiment, the distance between the outer boundaries of the lesion 42 and the outer edges or margin 44 of the tissue specimen 46 may be between about one and ten millimeters (1-10 mm), e.g., at least about two millimeters (2 mm) or at least about one centimeter (1 cm).

Figure 2B:
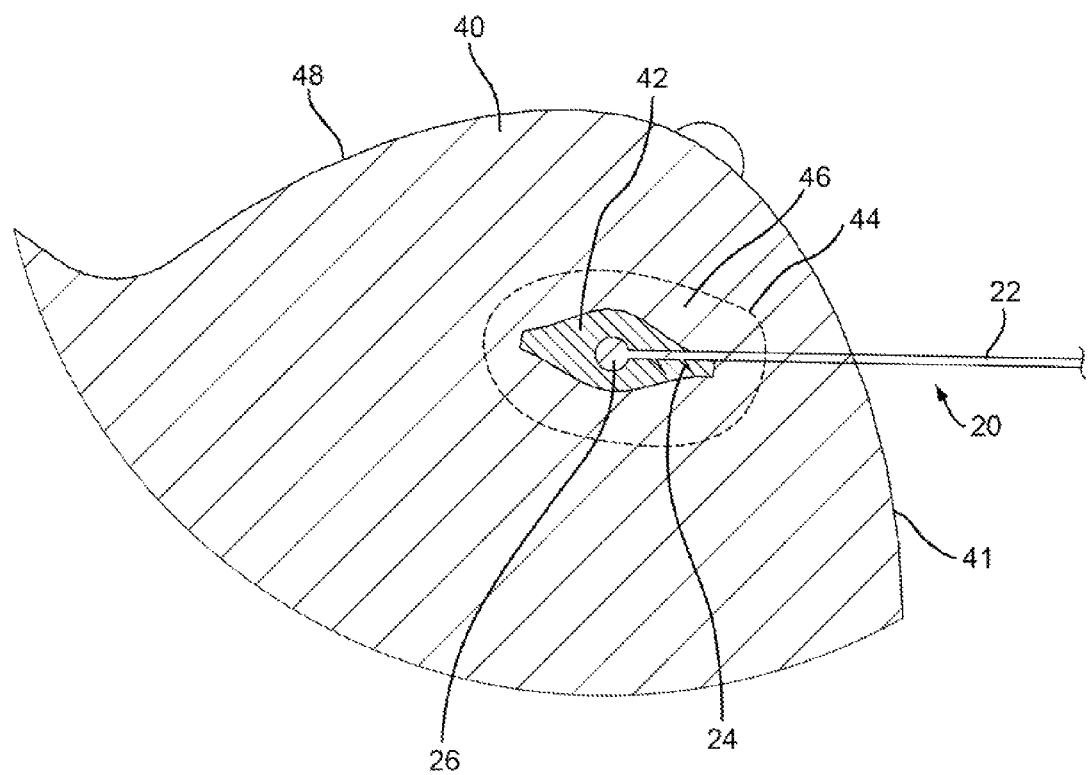
FIG. 2B is a cross-sectional view of the breast, taken along line 2B-2B in FIG. 2A, showing a target on the localization wire disposed within the target tissue region.

Referring to FIGS. 2A and 2B, the localization wire 20 may be introduced percutaneously through tissue 40, e.g., from the patient's skin 48 through intervening tissue until the target 26 is positioned within the lesion 42. In an exemplary embodiment, the localization wire 20 may be introduced through a delivery sheath (not shown), which may be placed previously using a needle and/or dilator (also not shown), similar to the cannula 340 described with reference to FIGS. 20-22 elsewhere herein. For example, a cannula or delivery sheath having a sharpened tip may be penetrated through the skirt 48 and intervening tissue 40 into the lesion 42, e.g., using ultrasound or x-ray imaging for guidance, and then the localization wire 20 may be advanced through the cannula. Alternatively, a needle having a sharpened tip may be advanced through tissue and then a delivery sheath may be advanced over the needle (not shown), e.g., along with a dilator between the needle and delivery sheath. Once the delivery sheath is positioned such that it extends from the skin 48 to the lesion 42, the needle and any dilator may be removed. The distal end 22b of the localization wire 22 may then be advanced through the delivery sheath until the target 26 is positioned within the lesion 42, whereupon the delivery sheath may be removed. Optionally, the localization wire 22 may include one or more markers (not shown) on the distal end, e.g., radiopaque or echogenic markers, on or adjacent the target 26, to facilitate imaging the target 26 and/or distal end 22b of the localization wire 22. External imaging may then be used during and/or after introduction of the localization wire 20 to ensure that the target 26 is properly positioned within the lesion 42.

If the localization wire 20 includes anchoring element(s), such as barbs 24, the barbs 24 may be compressed inwardly when the localization wire 20 is advanced through the delivery sheath. Once the target 26 is positioned within the lesion 42, the delivery sheath may be withdrawn, whereupon the barbs 24 may resiliently expand outwardly into the adjacent tissue. Thus, the barbs 24 on the distal end 22b of the shaft 22 may anchor the localization wire 20 relative to the lesion 42, e.g., such the target 26 may be substantially secured in a fixed position within the lesion 42. In addition or alternatively, a bandage, tape, and the like (not shown) may be used to secure the proximal end 22a of the localization wire 22a to the patient's skin 48, e.g., to prevent migration of the localization wire 22.

Figure 3:
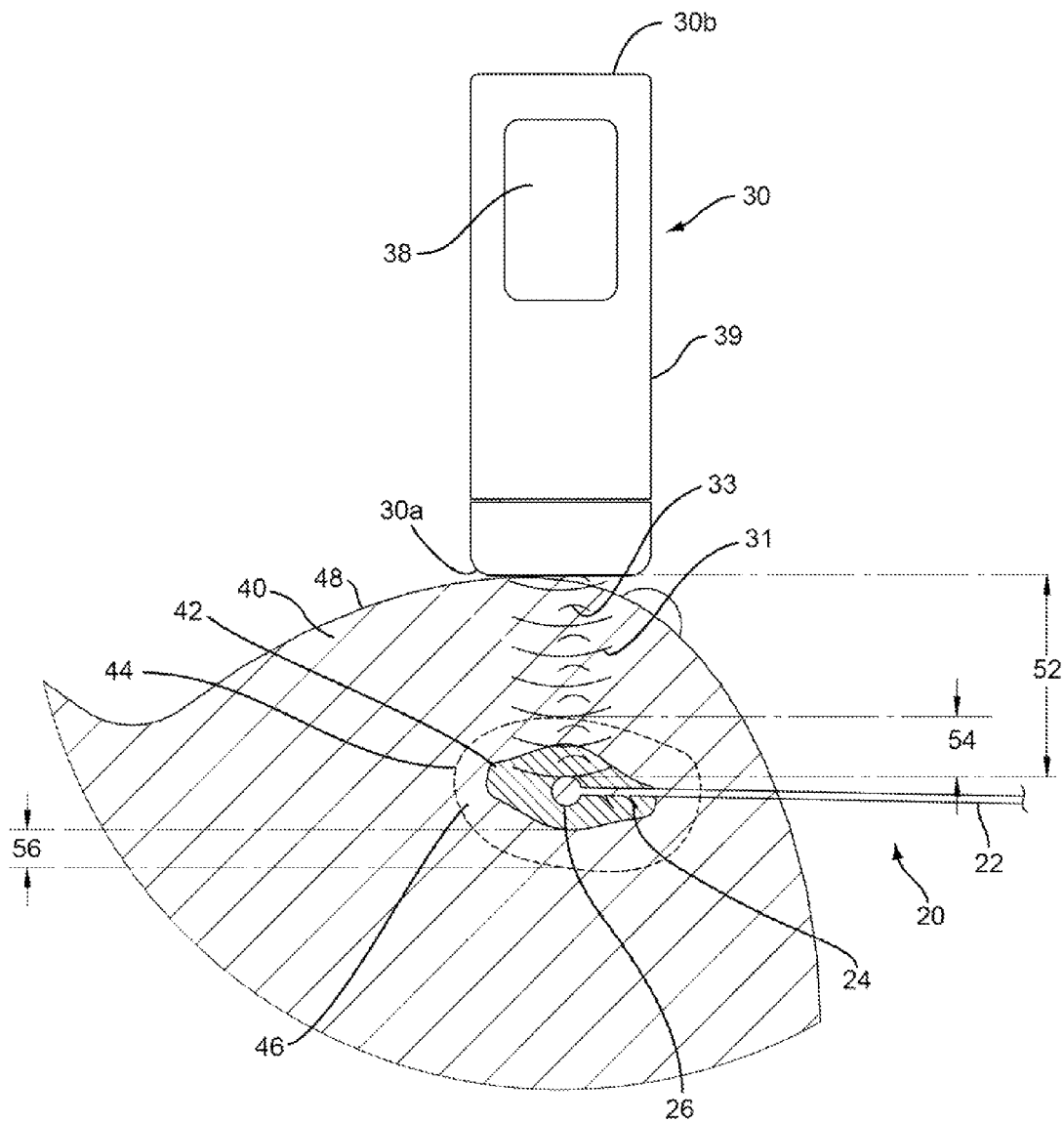
FIG. 3 is a cross-sectional view of the breast depicted in FIGS. 2A and 2B, showing the probe of FIG. 1 being used to take a first distance measurement to the target of the localization wire, e.g., to determine the distance from the skin to the lesion, a desired margin, and/or a size of a specimen to be removed from the breast.

After the localization wire 20 is correctly positioned and/or secured, the first end 30a of the probe 30 may be placed adjacent or in contact with the patient's skin 48, e.g., generally above the lesion 42, and/or otherwise aimed generally towards the target 26, and activated, as shown in FIG. 3. The transmit antenna 32 (not shown, see FIG. 10) of the probe 30 may emit electromagnetic signals 31 that travel through the tissue 40 and are reflected off of the target 26. The signals 33 may be reflected back to the receive antenna 34 (not shown, see FIG. 10) in the probe 30. The probe 30 may then determine a spatial relationship between the target 26 and the first end 30a of the probe 30, e.g., a distance 52 between the target 26 and the probe 30 (and the patient's skin 48 if contacted by the first end 30a of the probe 30), e.g., based on the distance traveled by the signals 31, passage of time between transmission of signals 31 and reception of reflected signals 33, and the like. Optionally, the probe 30 may also determine a relative angle between the target 26 and the first end 30a, e.g., to facilitate determining a proper direction of dissection.

In one embodiment, the micro-controller 36a (not shown, see FIG. 10) of the probe 30 may filter or otherwise analyze received signals to identify the target 26, e.g., based on recognition of the size, shape, or other aspects of the target 26. Thus, the micro-controller 36a may automatically be able to identify the target 26 and distinguish it from other structures that may be present in the patient's body. Alternatively, the micro-controller 36a may simply identify any objects reflecting signals back to the probe 30, which presumably would identify the target 26. For example, the micro-controller 36a may calculate the distance 52 and/or an angle relative to an axis extending orthogonally from the first end 30a of the probe 30, and display this spatial information on the display 38. This information may facilitate localizing the target 26, and consequently the lesion 42, which may provide guidance to a surgeon dissecting tissue overlying the lesion 42, e.g., by providing a direction and depth of dissection to access the target tissue region including the lesion 42.

In addition or alternatively, other information may be displayed on the display 38 if desired. For example, the display 38 may provide a distance 54 between the target 26 and the outer margin 44 of the target tissue specimen 46, which may facilitate defining the targeted size and shape of the tissue specimen 46 to be removed. To determine the distance 54, the probe 30 may automatically subtract a predetermined distance between the desired margin 44 and the target 42, e.g., based on preset parameters programmed into the processor 36 of the probe 30 or based on dimensions provided to the micro-controller 36a by the user immediately before the procedure, e.g., via user controls 37 (not shown, see FIG. 10).

Figure 4:
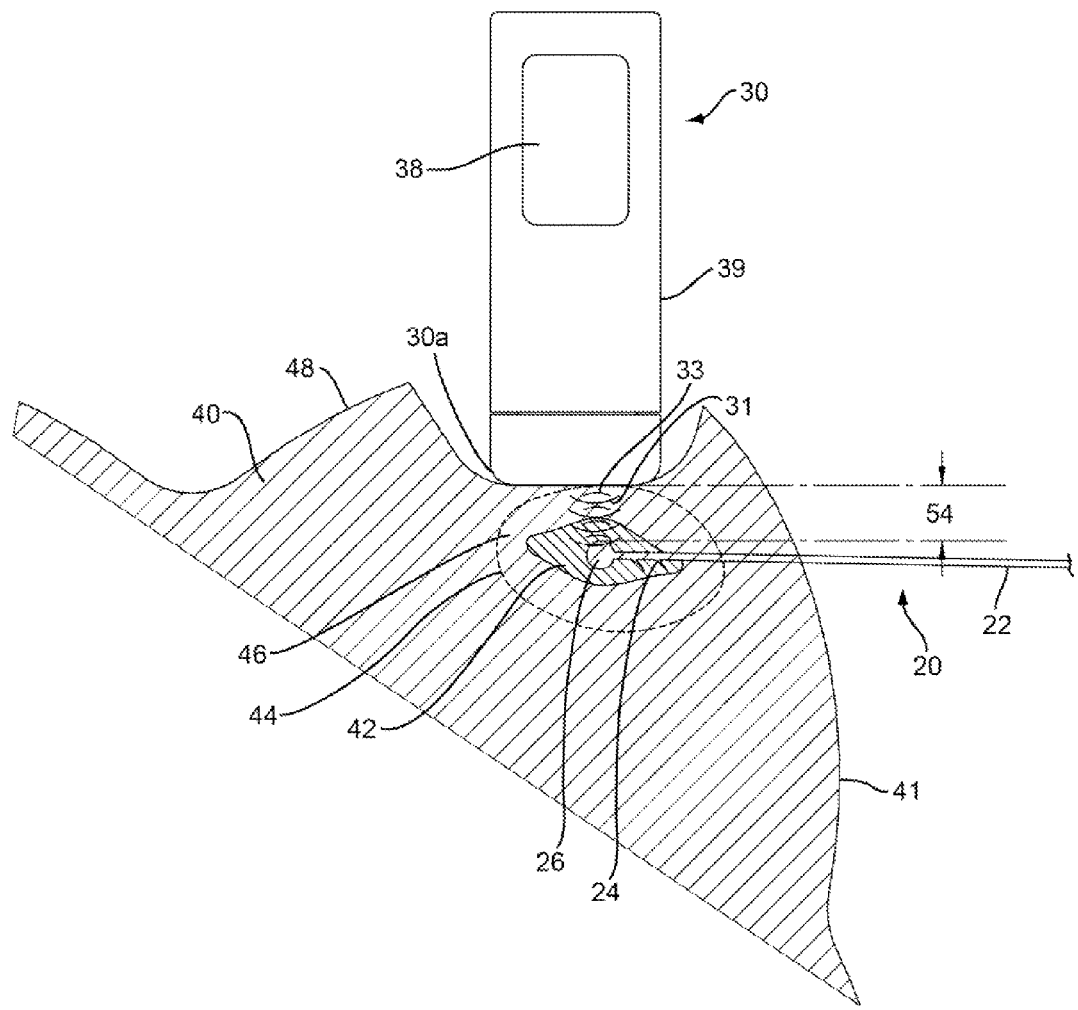
FIG. 4 is a cross-sectional view of the breast depicted in FIGS. 2A, 2B, and 3 after initial dissection has been performed, showing the probe being used to take a second distance measurement, e.g., to determine whether the tissue has been dissected sufficiently to reach the desired margin for the specimen to be removed.

Optionally, with continued reference to FIG. 3, the probe 30 may be positioned at several locations against or otherwise adjacent the skin 48 and spatial information obtained, if desired. Such information may facilitate the surgeon determining an optimal approach path for dissection, e.g., the shortest path to the lesion 42, or otherwise help orient the surgeon relative to the lesion 42 in three dimensions. After the distance 52 between the patient's skin 48 and the target 26 from a desired location on the skin 48 is determined, the tissue 40 may be dissected to reach the predetermined outer edge 44 of the tissue specimen 46, as shown in FIG. 4. For example, an incision may be made in the patient's skin 48 at the location where the probe 30 was placed and the intervening tissue dissected using known methods until the depth corresponding to the margin 44 is achieved. Optionally, at any time during dissection, the probe 30 may be placed against or adjacent the exposed tissue and spatial information obtained to confirm the approach and/or depth of dissection.

With continued reference to FIG. 4, if desired, once the surgeon believes the desired margin 44 has been reached, another length measurement may be taken with the probe 30 to verify that the predetermined distance 54 to the target 26 has been reached. For example, the first end 30a of the probe 30 may be placed in contact with the bottom surface of the dissected tissue area, signals 31 may be transmitted by the transmit antenna 32, and signals 33 may be received by the receive antenna 34 in order for the probe 30 to determine the distance between the bottom surface of the dissected tissue area and the target 26. After verifying that the desired margin 44 of the tissue specimen 46 has been reached, the tissue specimen 46 may be excised or otherwise removed using conventional lumpectomy procedures with the target 26 remaining within the removed specimen 46. If desired, the target 26 may be separated from the shaft 22 to facilitate removal of the specimen 46, e.g., by cutting the distal end 22b of the shaft 22, by disconnecting any connectors (not shown) between the shaft 22 and target 26, and the like.

Figure 5:
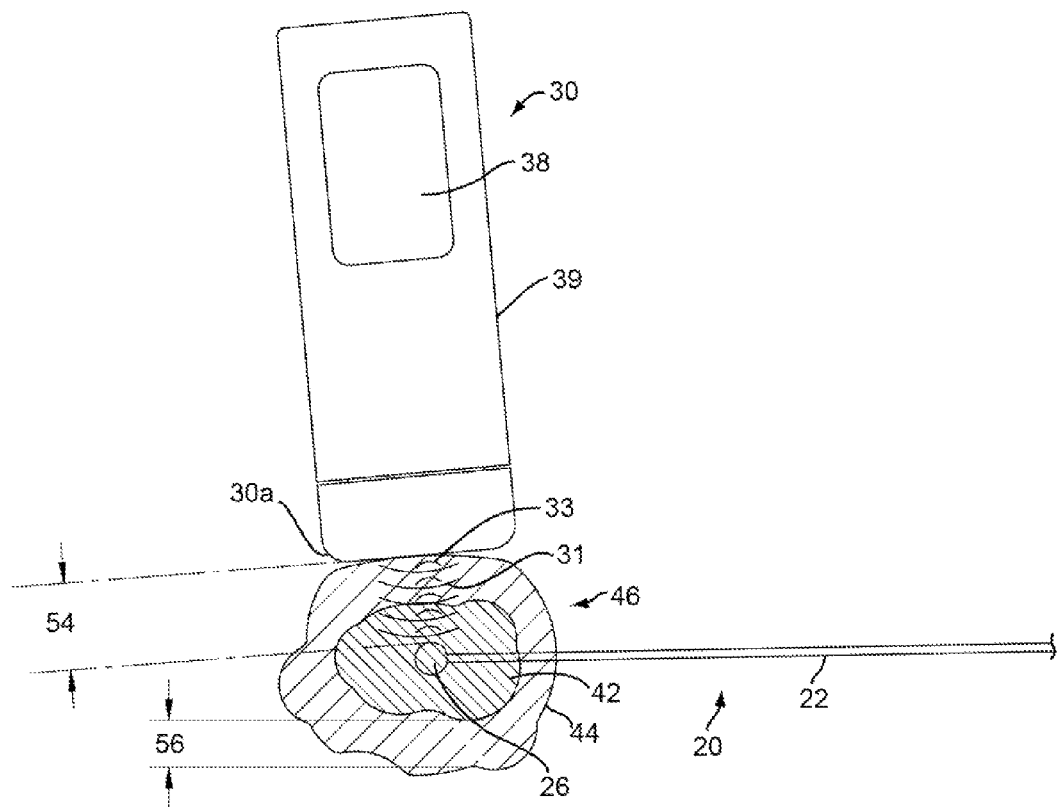
FIG. 5 is cross-sectional view of an excised tissue specimen taken from the breast of FIGS. 2A and 2B, showing the probe being used to take a third distance measurement, e.g., to confirm that the desired margin around the lesion has been achieved.

Turning to FIG. 5, if desired, the probe 30 may be used to analyze the excised tissue specimen 46, e.g., to confirm that the desired margin 44 has been achieved around the target 26, and consequently around the lesion 42. As shown, transmit signals 31 are transmitted by the probe 30 and signals 33 are reflected off the target 26 and received by the probe 30, whereupon the probe 30 may determine and display the distance 54 and/or any other spatial information. In this manner, it can be verified that the predetermined tissue margin has been achieved.

Turning to FIGS. 6-9, another exemplary embodiment of a system 110 for localizing a lesion or other tissue structure, e.g., a plurality of non-palpable lesions 142, is shown that includes a probe 30 and a plurality of implantable markers or targets 120. The probe 30 may be a portable device capable of transmitting electromagnetic signals and receiving reflected signals, similar to the embodiments described elsewhere herein.

The markers 120 may include a plurality of implantable elements sized for introduction through tissue into a region surrounding the lesion 142. For example, the markers 120 may be formed as a plurality of strips, cylinders, helixes, spheres, and the like, e.g., having features to enhance reflection of electromagnetic and/or ultrasound signals transmitted by the probe 30, similar to the target 26 described above with reference to FIG. 1 and/or the markers described further elsewhere herein, e.g., with reference to FIGS. 23A-28C, 34A, 34B, 41A, and 41B.

Figure 6:
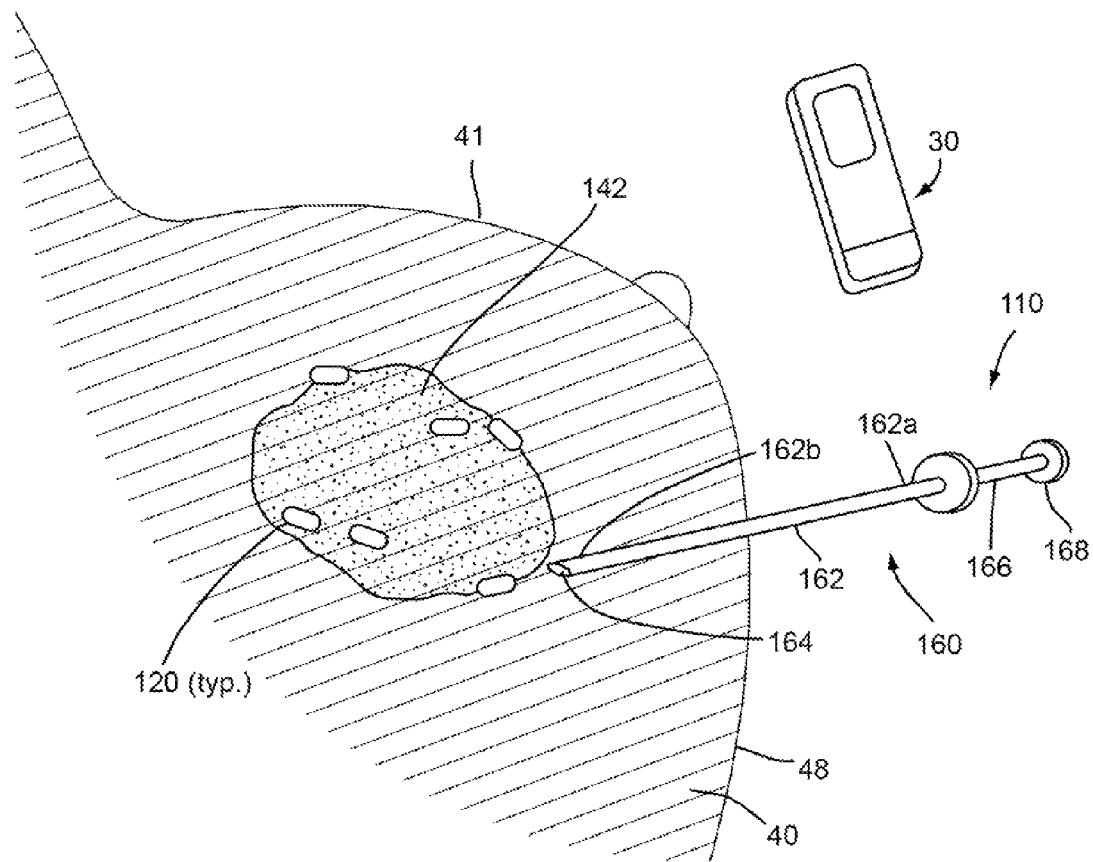
FIG. 6 is a perspective view of a breast, showing a delivery device being used to deliver a plurality of markers around one or more lesions, e.g., a group of non-palpable lesions, within the breast.

As shown in FIG. 6, the markers 120 may be elongate strips, e.g., rectangular or other shaped markers having a length between about half to four millimeters (0.5-4.0 mm), a width between about half and two millimeters (0.5-2.0 mm), and a thickness between about half and three millimeters (0.5-3.0 mm). The markers 120 may be formed from metal or other material that may enhance detection by the probe 30, e.g., having a desired dielectric constant. In addition or alternatively, the markers 120 may be formed from bioabsorbable material, e.g., gelatin, polylactic acid (PLA), polyglycolic acid (PGA), and the like, such that the markers 120 may be implanted within tissue and then dissolved or otherwise absorbed by the tissue over time, e.g., over several days, weeks, or months.

Optionally, the markers 120 may be formed from radiopaque material, radioactive material, and/or echogenic material, which may facilitate imaging or otherwise monitoring the markers 120, e.g., during introduction, after placement during a procedure, or afterwards if the markers 120 remain within the patient's body after the procedure. In addition, if desired, each marker 120 may have a surface, shape, and/or additional material feature that may distinguish one or more of the markers from others, as described elsewhere herein. For example, each marker 120 may modulate an incident signal from the probe 30 in a predetermined manner and/or absorb or reflect a particular electromagnetic signal that is specific to that marker 120 and may be used to uniquely identify it.

In addition, as shown in FIG. 6, the system 110 may also include one or more delivery devices 160 for introducing the markers 120 into a patient's body. For example, a delivery device 160 may be provided that includes a shaft 162 including a proximal end 162a and a distal end 162b sized for introduction through tissue into a target tissue region (not shown) and carrying one or more markers 120. The delivery device 160 may include a lumen 164 extending at least partially between the proximal and distal ends 162a, 162b of the shaft 162, and a pusher member 166 slidable within the shaft 162 for selectively delivering one or more markers 120 successively or otherwise independently from the lumen 164.

As shown, the distal end 162b of the shaft 162 may be beveled and/or otherwise sharpened such that the shaft 162 may be introduced directly through tissue. Alternatively, the delivery device 160 may be introduced through a cannula, sheath, or other tubular member (not shown) previously placed through tissue, e.g., as described elsewhere herein.

Optionally, the distal end 162b may include a band or other feature, e.g., formed from radiopaque, echogenic, or other material, which may facilitate monitoring the distal end 162b during introduction, e.g., using fluoroscopy, ultrasound, electromagnetic signals, and the like.

As shown, the pusher member 166 includes a piston or other element (not shown) disposed within the lumen 164 adjacent the marker(s) 120 and a plunger or other actuator 168 coupled to the piston for advancing the piston to push the marker(s) 120 from the lumen 164. As shown, the plunger 168 may be manually advanced to deliver one or more markers 120 successively from the lumen 164. Alternatively, a trigger device or other automated actuator (not shown) may be provided on the proximal end 162b of the shaft 162, which may advance the piston sufficiently with each activation, e.g., to delivery an individual marker 120 from the distal end 162b.

Figure 7:
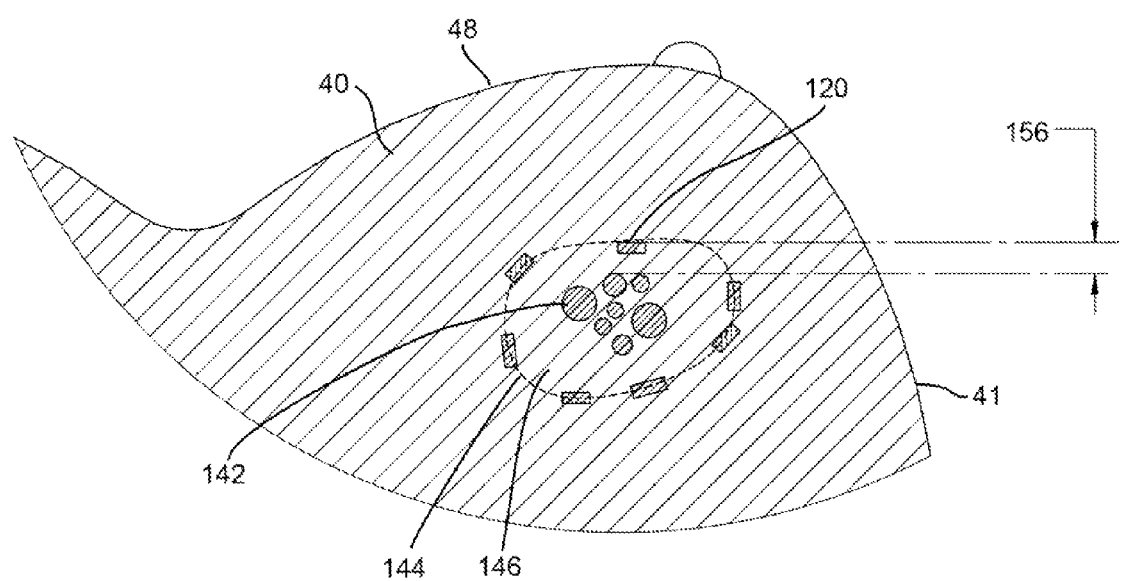
FIG. 7 is a cross-sectional view of the breast of FIG. 6, showing a plurality of markers placed around the lesions.

Returning to FIGS. 6-9, an exemplary method is shown for using the markers 120 and probe 30 to localize a lesion or other target tissue region 142 within a breast 41 or other tissue structure. As shown in FIGS. 6 and 7, the markers 120 may be implanted within the tissue 40 to delineate a desired margin or volume 144 of a tissue specimen 146 to be excised. For example, the shaft 162 of the delivery device 160 may be inserted percutaneously through the patient's skin 48, through any intervening tissue 40, and the distal end 162b positioned within or around the lesion 142, e.g., using external imaging to guide the distal end 162b to a desired location. Once in position, the plunger 168 may be advanced (or the shaft 162 withdrawn relative to the plunger 168) to deliver a marker 120 into the tissue. The delivery device 160 may be advanced further to another location and/or removed entirely from the breast 41 and reintroduced through another location of the skin 48 into the target tissue region, e.g., to deliver one or more additional markers 120. Introduction of the marker 120 may be imaged or otherwise monitored, e.g., using x-ray, radar, and/or ultrasound, to ensure proper placement and/or deployment of the marker 120, and the marker 120 may include features to enhance or otherwise facilitate such imaging, similar to other embodiments herein.

Alternatively, the delivery device 160 may carry only a single marker 120, and multiple delivery devices (not shown) may be provided for delivering each of the markers 120. In addition or alternatively, a stereotactic device (not shown) may be used, e.g., to introduce one or multiple delivery devices into the patient's body in a desired three-dimensional array or other arrangement for localizing the lesion 142. In a further alternative, the markers 120 may be replaced with multiple localization wires, similar to wire 10, one or more catheters (not shown) which may be delivered sequentially, simultaneously, and the like. Optionally, the catheter(s), wire(s), or other devices may be expandable, e.g., at a distal region (not shown) to facilitate dilating and/or identifying a specimen volume or region.

In the exemplary embodiment shown in FIGS. 6 and 7, the markers 120 surround a group of non-palpable lesions 142, e.g., before or during a procedure to remove a specimen volume surrounding the lesions 142. The distance 156 between the outer edge 144 of the tissue specimen 146 and the lesions 142 may be selected to ensure that the volume of tissue removed is sufficient to ensure clear margins, similar to the methods described above.

As shown in FIG. 7, after the markers 120 have been implanted, the probe 30 may be placed against or otherwise adjacent the patient's skin 48 (e.g., it may be unnecessary to contact the patient's skin 48 with the probe 30 to transmit and receive signals into and from the tissue 40), and the probe 30 may be used to determine the distance 152 (and/or other spatial information) between the probe 30 and the markers 120, similar to the previous embodiments. In particular, the signals 31 emitted by the probe 30 may be received at the markers 120 and reflected back to a receiver in the probe 30 as signals 33, and the probe 30 may use the signals to determine the distance 152 between the patient's skin 48 and the markers 120.

Figure 8:
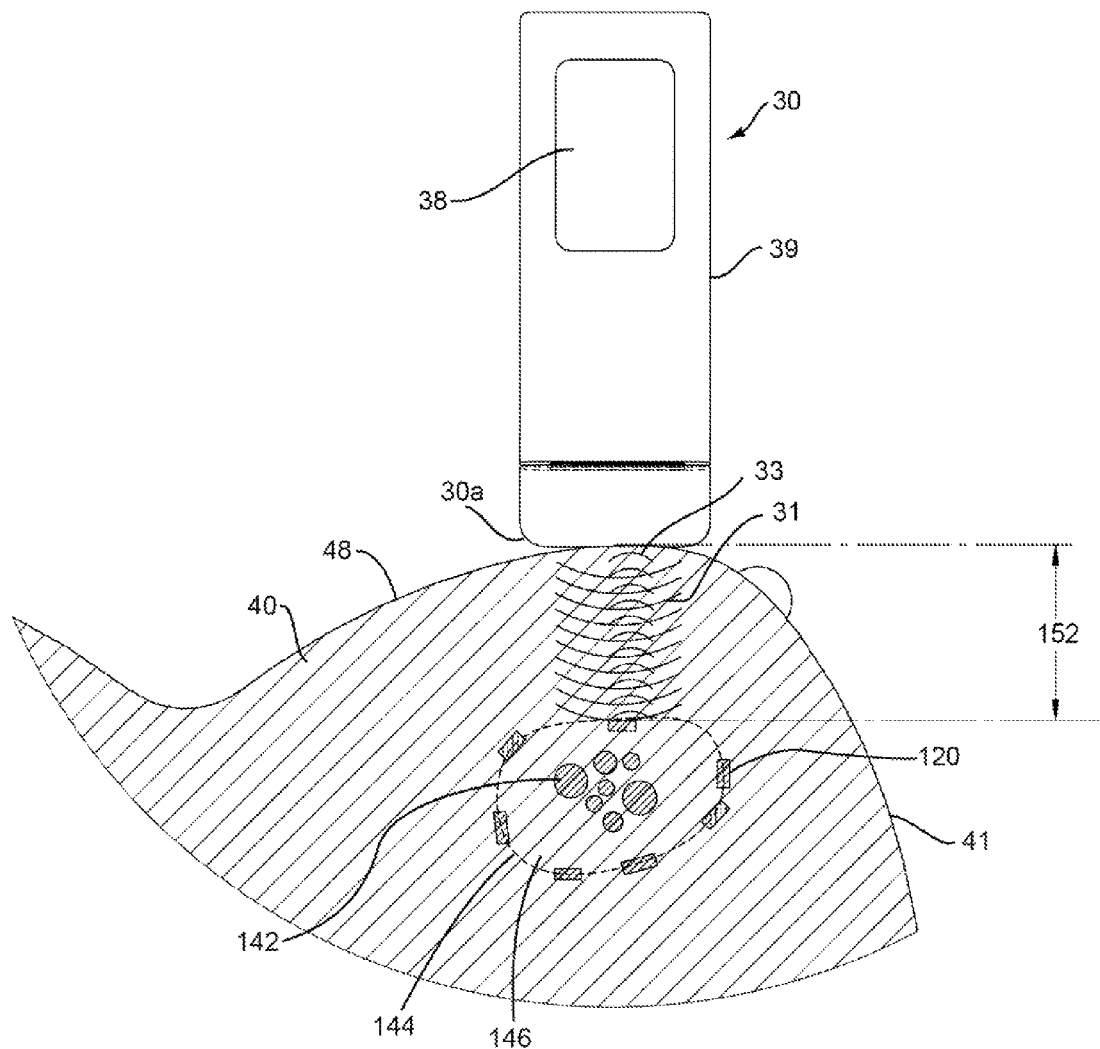
FIG. 8 is a cross-sectional view of the breast depicted in FIGS. 6 and 7, showing a probe being used to take a first set of distance measurements, e.g., to determine a distance to one or more of the markers.
Figure 9:
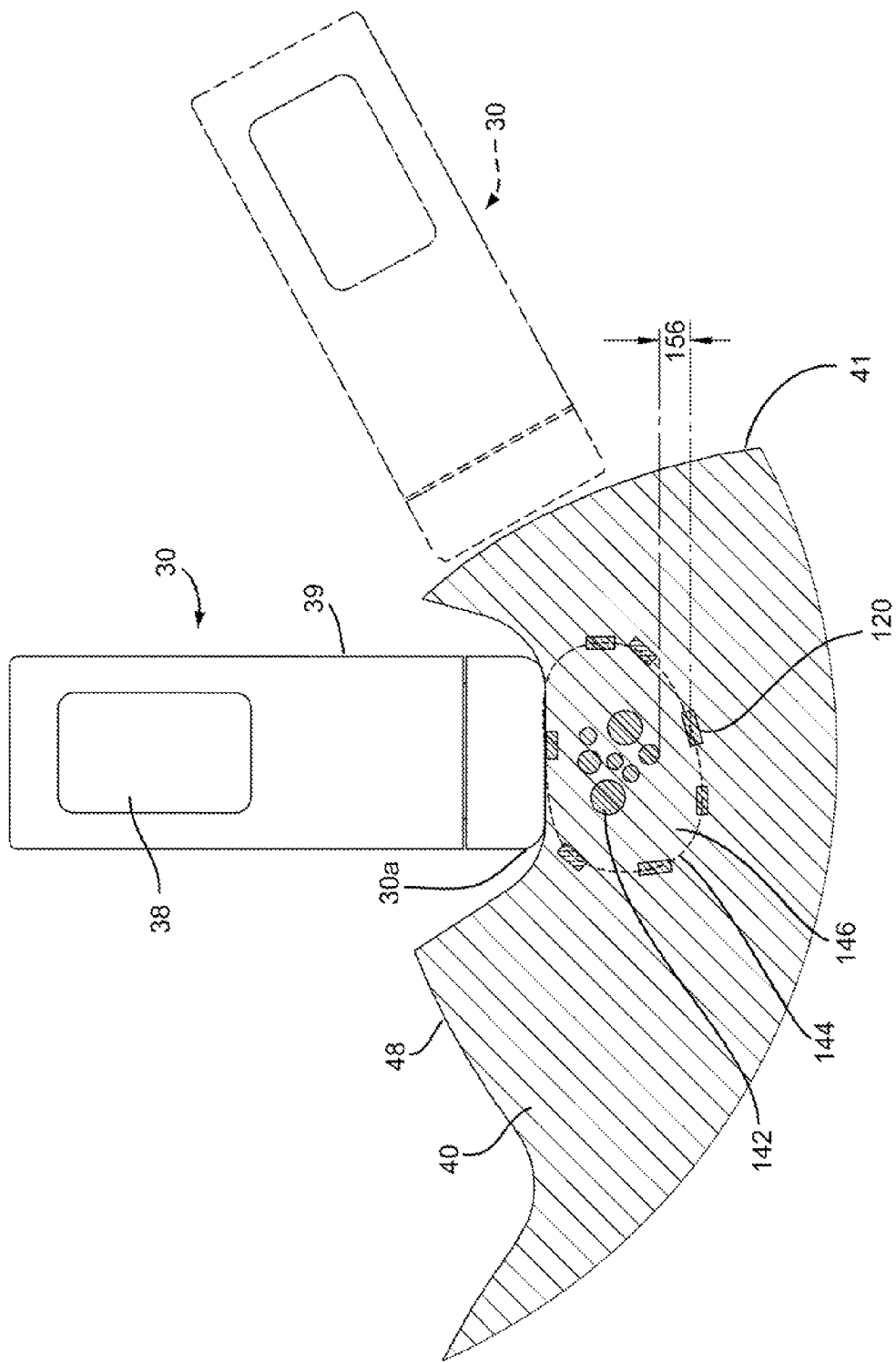
FIG. 9 is a cross-sectional view of the breast depicted in FIGS. 6-8, showing the probe being used to facilitate dissection down to the markers, e.g., to define a desired margin around a specimen to be removed from the breast.

The tissue 40 surrounding the lesions 142 may then be dissected until one of the markers 120 is encountered, as shown in FIG. 8. At this point, another measurement may be taken with the probe 30 to ensure proper dissection depth. The probe 30 may then be repositioned, as shown in phantom in FIG. 8, to locate another one of the markers 120 around the periphery 144 of the tissue specimen 146. The resulting distance measurements may be used to determine a desired margin volume for excision around the lesions 142. This process may be repeated as often as desired to facilitate measuring the desired margin based on the distance to the markers 120 during excision of the tissue specimen 146 around the lesions 142. The tissue specimen 146 may include the markers 120 therein such that all of the markers 120 are removed with the tissue specimen 146. Alternatively, the desired margin may be defined within the markers 120 such that the markers 120 remain within the breast after the tissue specimen 120 is removed. In this alternative, the markers 120 may be bioabsorbable or may be inert and remain indefinitely within the patient's breast 41.

Turning to FIGS. 11-15, another exemplary system and method are shown for localizing one or more lesions 142 within a breast 41 and/or removing a tissue specimen 146 (shown in FIGS. 14A-15A) including the lesion(s) 142. Similar to the previous embodiments, the system includes one or more markers 220 and a probe instrument 130, which may facilitate localizing the lesion(s) 142 and/or ensuring desired margins are achieved for the tissue specimen 146 removed from the breast 41. The probe instrument 130 includes a handheld probe 131 coupled to a processor 139 including one or more processors for controlling operation of the probe 131, as described above. Also as described above, the handheld probe 131 includes an elongate housing 131a including one or more antennas 132 on or within a tip 131b on one end of the probe 131 that may be placed against the skin 48 or other tissue and/or otherwise oriented generally towards the marker 220 and/or lesion(s) 142.

The processor 139 may include one or more processors for controlling the antenna(s) 132, a display 138, and the like, similar to the previous embodiments. The handheld probe 131 may be coupled to the processor 139 by one or more cables 133. For example, an impulse generator, impulse receiver, and/or gate control may be provided within the processor 139, which may be controlled to emit and receive signals via the antenna(s) 132.

Figure 14:
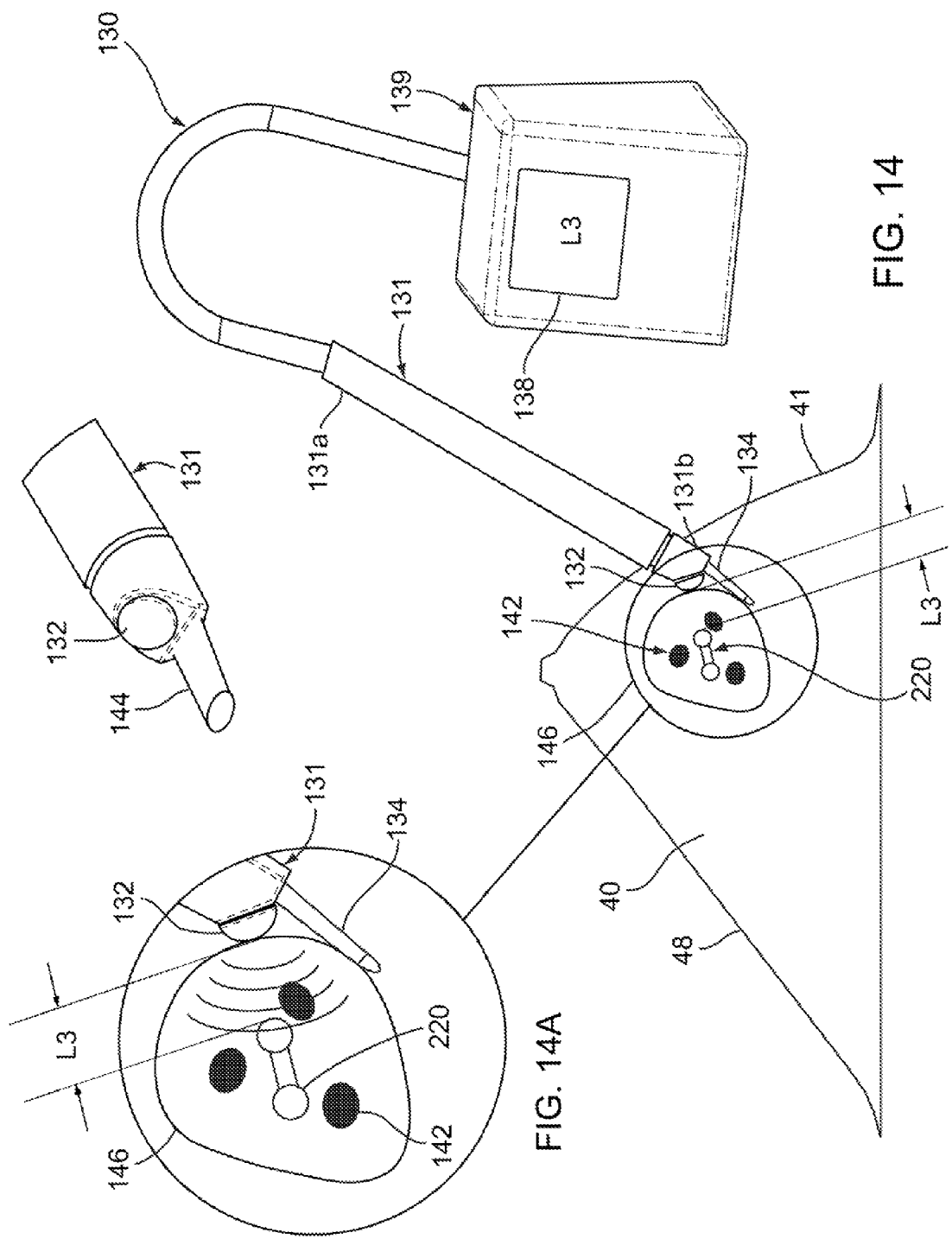

Optionally, as shown in FIGS. 14 and 14A, the handheld probe 131 may include a dissecting feature 133, e.g., extending from the tip 131b of the housing 131a. In one embodiment, the dissecting feature 133 may be a relatively flat blunt dissector fixed to the tip 131b of the probe 131, e.g., having a length of about ten to fifty millimeters (10-50 mm) and/or a width of about one to ten millimeters (1-10 mm). Alternatively, the dissecting feature 133 may be retractable, e.g., such that the dissecting feature 133 may be initially retracted within the housing 131a, but may be selectively deployed when desired to dissect layers of tissue to access tissue adjacent the marker 220. In a further alternative, the dissecting feature 133 may include a sharpened blade or edge, which may facilitate cutting through the patient's skin 48 and/or underlying layers of tissue 40.

Figure 12:
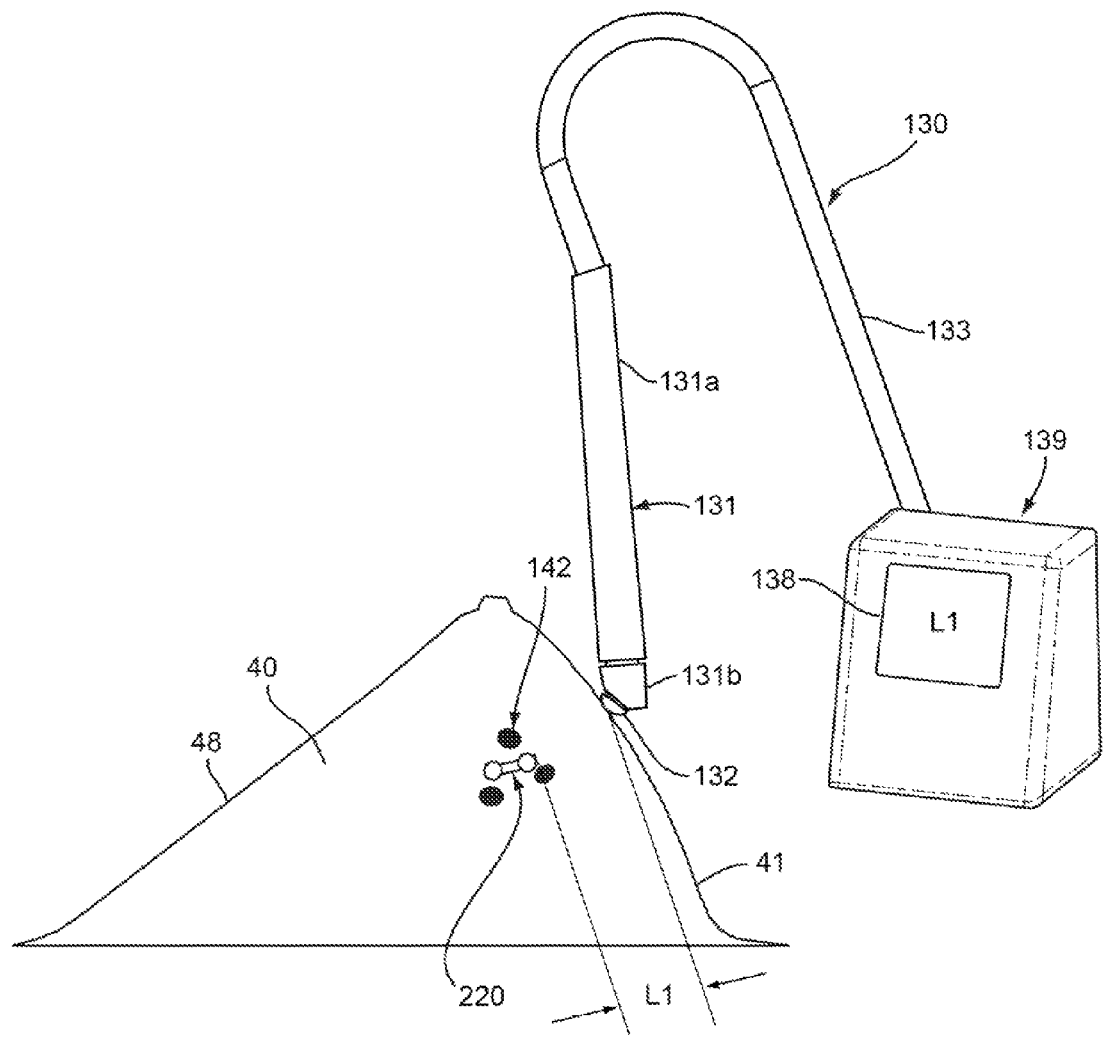
FIGS. 12-15 are side views of the system of FIG. 11 being used to locate the marker to facilitate removing a tissue specimen from the breast including the lesion.

Initially, as shown in FIG. 11, during use, one or more markers 220 may be implanted within the target tissue region, e.g., using the markers and/or methods described elsewhere herein. The probe 131 may be coupled to the processor 139, e.g., by cable 133, and the tip 131b placed against the skin 48. The probe 131 may be activated, e.g., to obtain an initial distance measurement from the tip 131b of the probe 131 to the marker 220 using the antenna(s) 132, thereby providing an approximate distance to the lesion(s) 142. The distance measurement may be displayed on the display 138 of the processor 139, e.g., as shown in FIG. 12, and/or otherwise provided to the user. In addition or alternatively, as described above, a speaker may provide the distance measurement, e.g., using a synthesized voice, one or more tones identifying corresponding distances, and the like, to identify the distance. For example, the processor 139 may analyze the received signals to determine the actual distance from the tip 131b of the probe 131 to the marker 220, and may provide the actual measurement via the speaker. Alternatively, the speaker may provide a tone corresponding to a predetermined threshold, e.g., a first tone for a first threshold distance, a second tone or multiple tones for a second, closer distance, and the like, thereby indicating to the user that they are getting closer to the marker 220.

As shown in FIG. 11, with the probe 131 on a first side of the breast 41, a measurement L1 is obtained, while with the probe 131' placed on a second opposite side of the breast 41, a measurement L2 is obtained, which is greater than L1. With this information, the physician may decide to initiate dissection on the first side since it provides a shorter path requiring less tissue dissection than a path initiated from the second side, as shown in FIG. 12.

Figure 13:
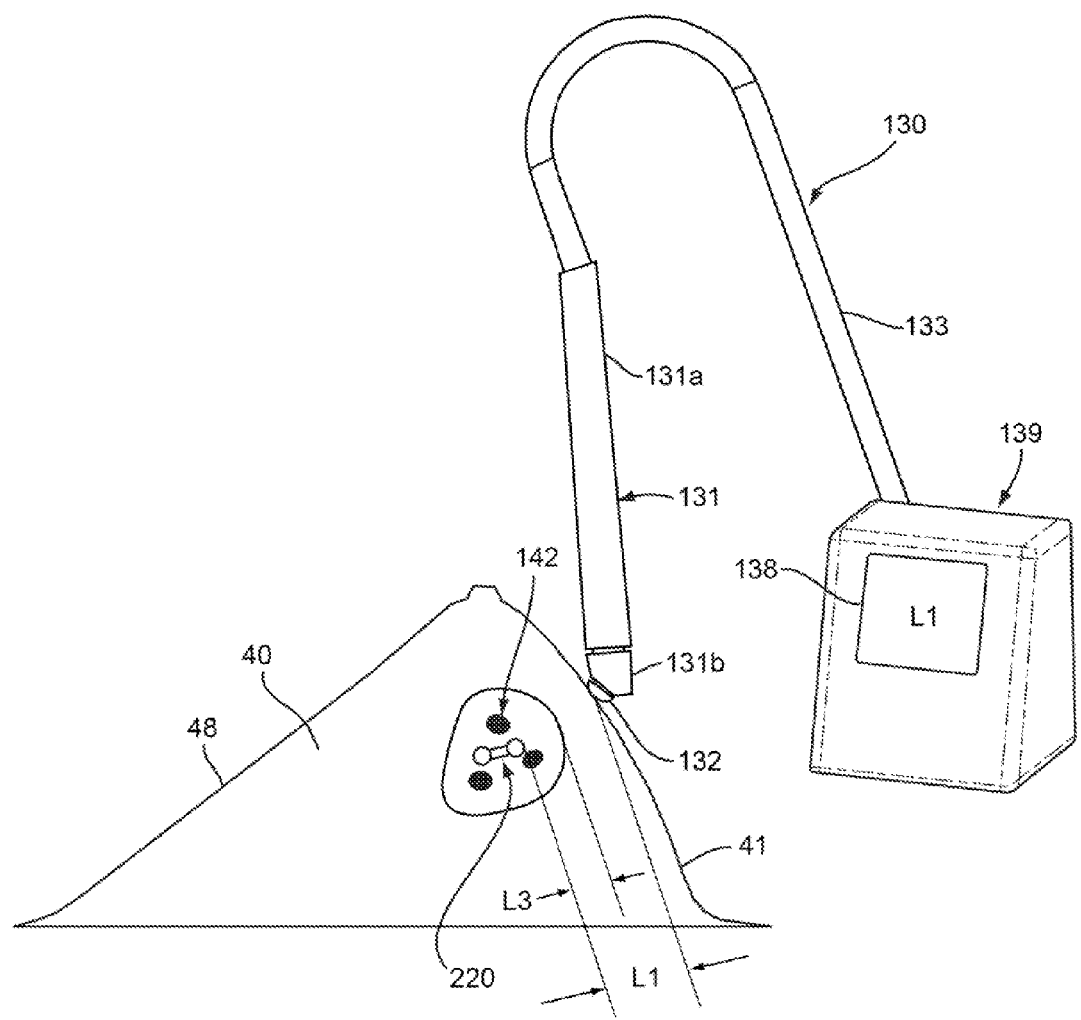

Turning to FIG. 13, the probe 131 may be used to identify a desired margin L3 around the marker 220 and consequently around the lesion(s) 142. For example, if a desired margin L3 of one centimeter (1 cm) is desired, the probe 131 may be display or otherwise provide the actual distance L1 from the probe 131 to the marker, as shown on the display 138, thereby indicating that the probe 131 remains outside the margin L3. Alternatively, if the processor 139 knows the desired margin L3, the display 138 may provide the difference between the actual distance L1 and the desired margin L3 (i.e., L1-L3), thereby informing the physician of the depth of dissection necessary to attain the desired margin.

Optionally, as shown in FIGS. 14 and 14A, if the probe 131 includes the blunt dissector 144, the blunt dissector 144 may be deployed from the tip 131b of the probe 131 (if not permanently deployed) and advanced through the tissue 40 towards the marker 220, e.g., until the desired margin L3 is attained. The probe 131 may then be manipulated to dissect tissue around the marker 220 using the blunt dissector 144 and/or using one or more additional dissectors, scalpels, or other tools (not shown).

Figure 15:
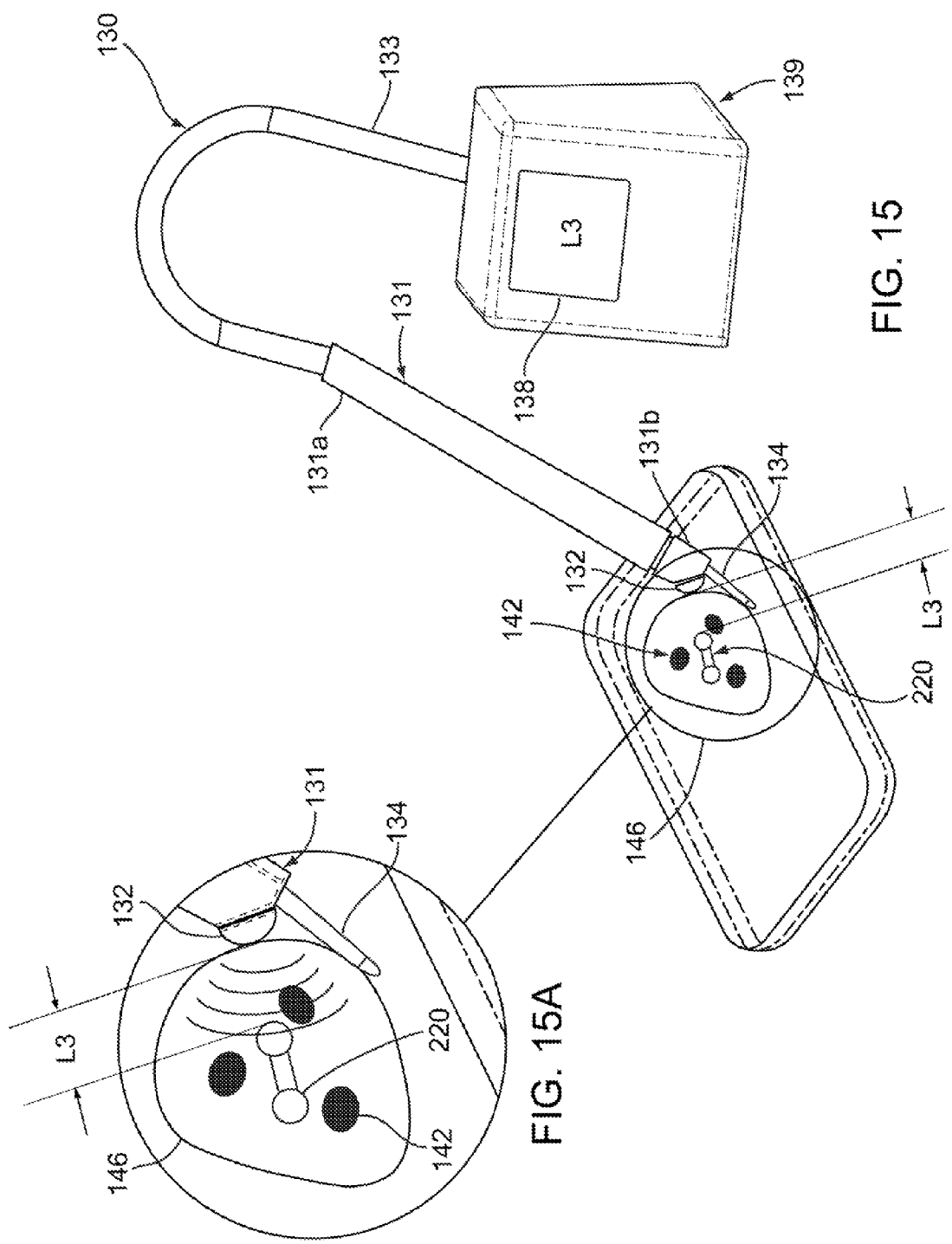

As shown in FIGS. 15 and 15A, a tissue specimen 146 has been removed from the breast 41 that includes the marker 220 and the lesion(s) 142 therein. Optionally, the probe 131 may then be used to confirm that the desired margin L3 was achieved around the marker 220, thereby providing confirmation that sufficient tissue has been removed from the breast 41, similar to the previous embodiments.

Figure 16:
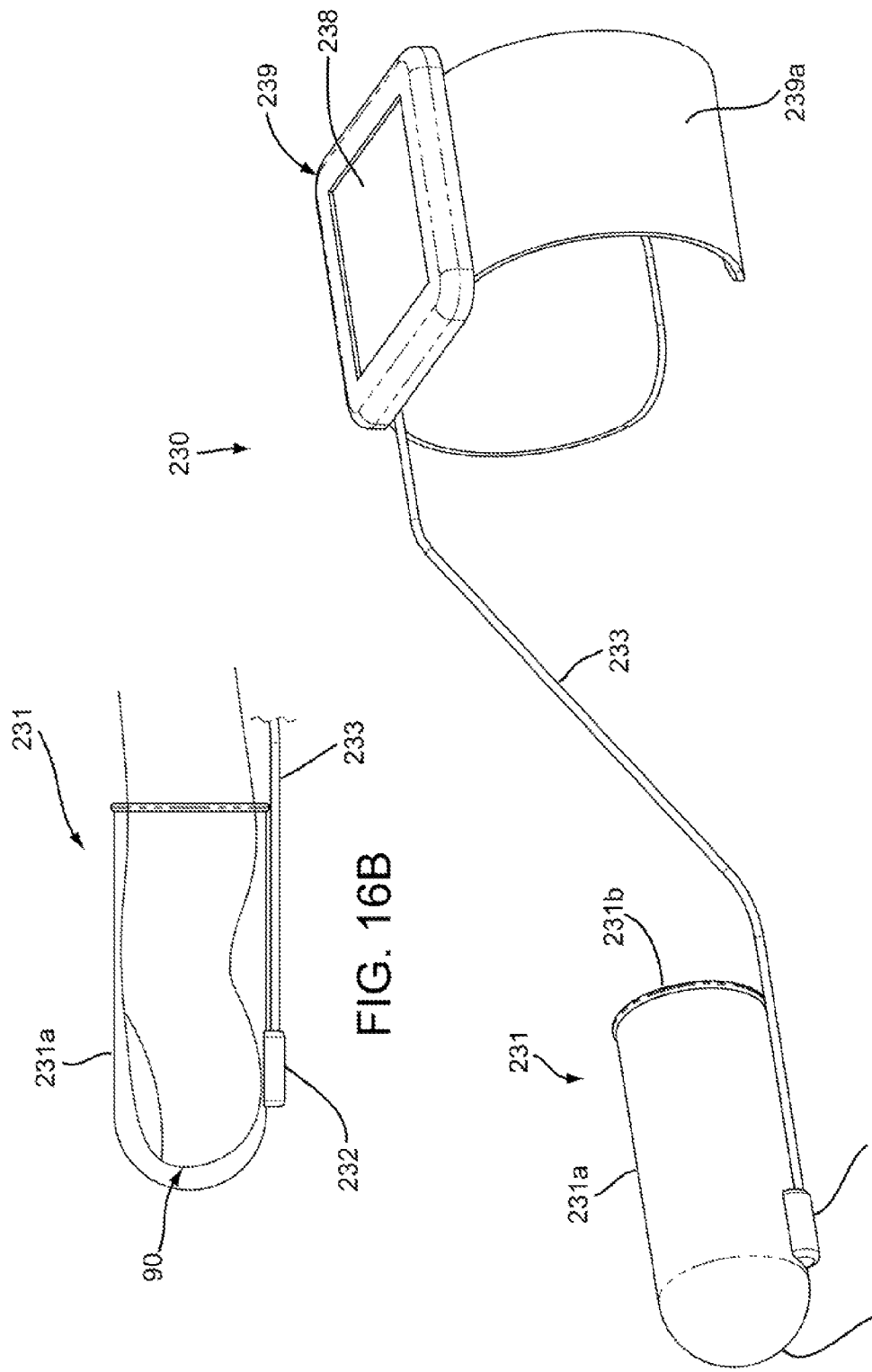
FIG. 16A is a perspective view of another exemplary embodiment of a probe instrument including a finger cot with integral probe and a controller coupled to the probe.
FIG. 16B is a side view detail of the finger cot of FIG. 16A showing a finger received therein.

Turning to FIGS. 16A and 16B, still another embodiment of a system is shown that includes one or more markers 220, a probe 231 including a finger cot 231a carrying one or more antennas 232, and a processor 239 coupled to the antenna(s) 232, e.g., by cable 233. The finger cot 231a may be a flexible sleeve, e.g., including an open end 231b into which a finger 90 may be inserted, a closed end 231c, and having sufficient length to be securely received over the finger 90. For example, the finger cot 231a may be formed from elastic material, such as a relatively thin layer of latex, natural or synthetic rubber, and the like, e.g., similar to surgical or examination gloves, having sufficient flexibility to expand to accommodate receiving the finger 90 while compressing inwardly to prevent the finger cot from 231a sliding off the finger 90 during use.

The antenna(s) 232 may be provided adjacent the closed end 231c, as shown. For example, the antenna(s) 232 may include a transmit antenna and a receive antenna (not shown), similar to the previous embodiments, provided within a casing. The casing may be attached to the finger cot 231a, e.g., adjacent the closed end 231c, for example, by bonding with adhesive, fusing, one or more overlying bands (not shown), and the like.

The processor 239 may include one or more components for operating the antenna(s) 232 and/or processing signals received from the antenna(s) 232, e.g., coupled to the antenna(s) 232 by cable 233 and including display 238, similar to the previous embodiments. In the embodiment shown, the processor 239 includes one or more clips 239a, straps, belts, clamps, or other features (not shown) that allow the processor 239 to be removably secured to the arm of a user whose finger is inserted into the finger cot 231a. For example, the clips 239a may be curved to extend partially around a user's forearm, and the clips 239a may be sufficiently flexible to open them to receive an arm therein and then resiliently close to engage at least partially around the arm. Alternatively, the processor 239 may be provided in a casing (not shown) that may be placed remotely from the patient and/or user, e.g., similar to the processor 139 described above.

Figure 17:
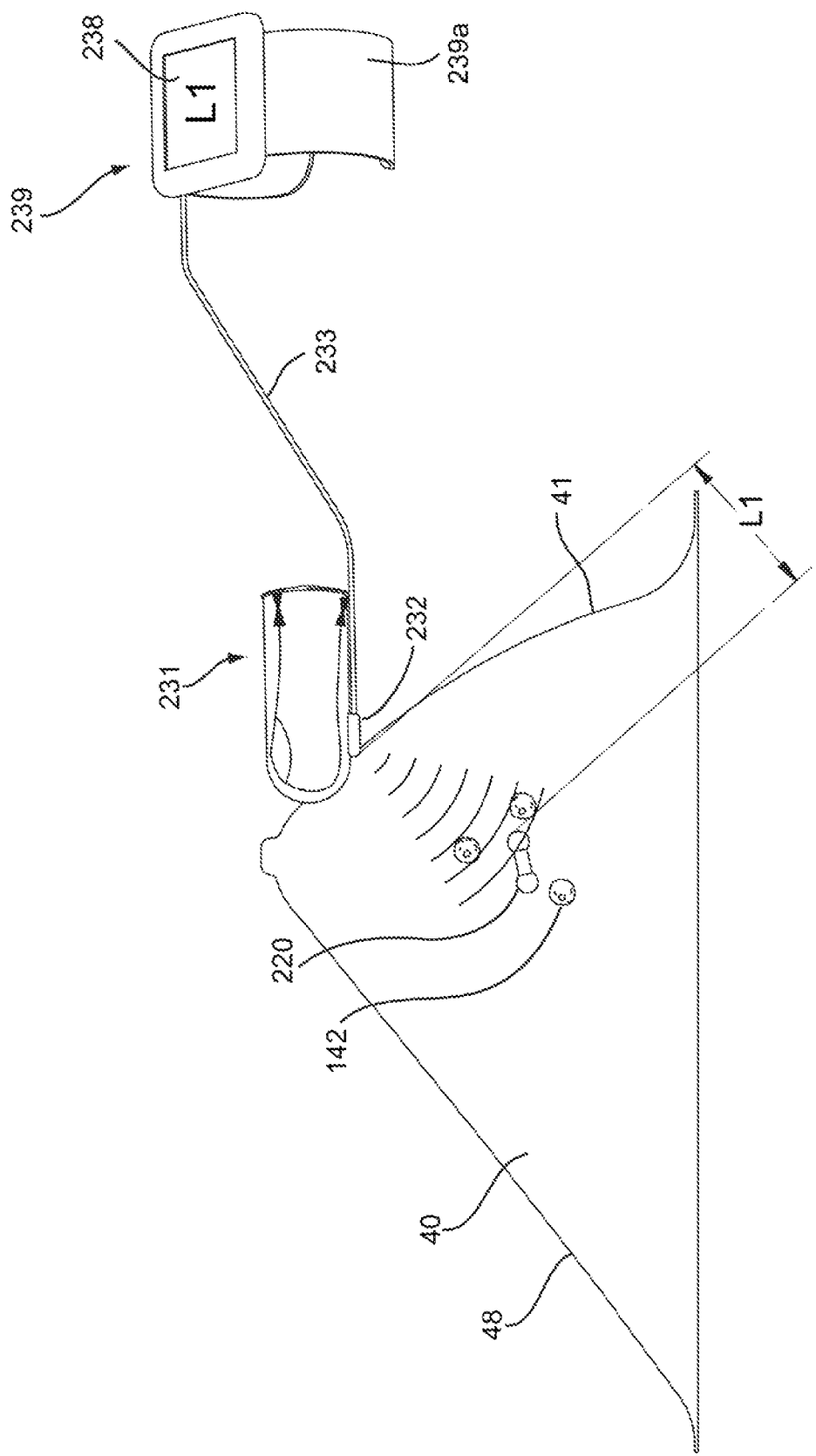
FIGS. 17 and 18 are cross-sectional views of a breast showing a marker implanted adjacent lesions and located using the probe instrument of FIGS. 16A and 16B during dissection of breast tissue to remove a tissue specimen including the lesions.
Figure 18:
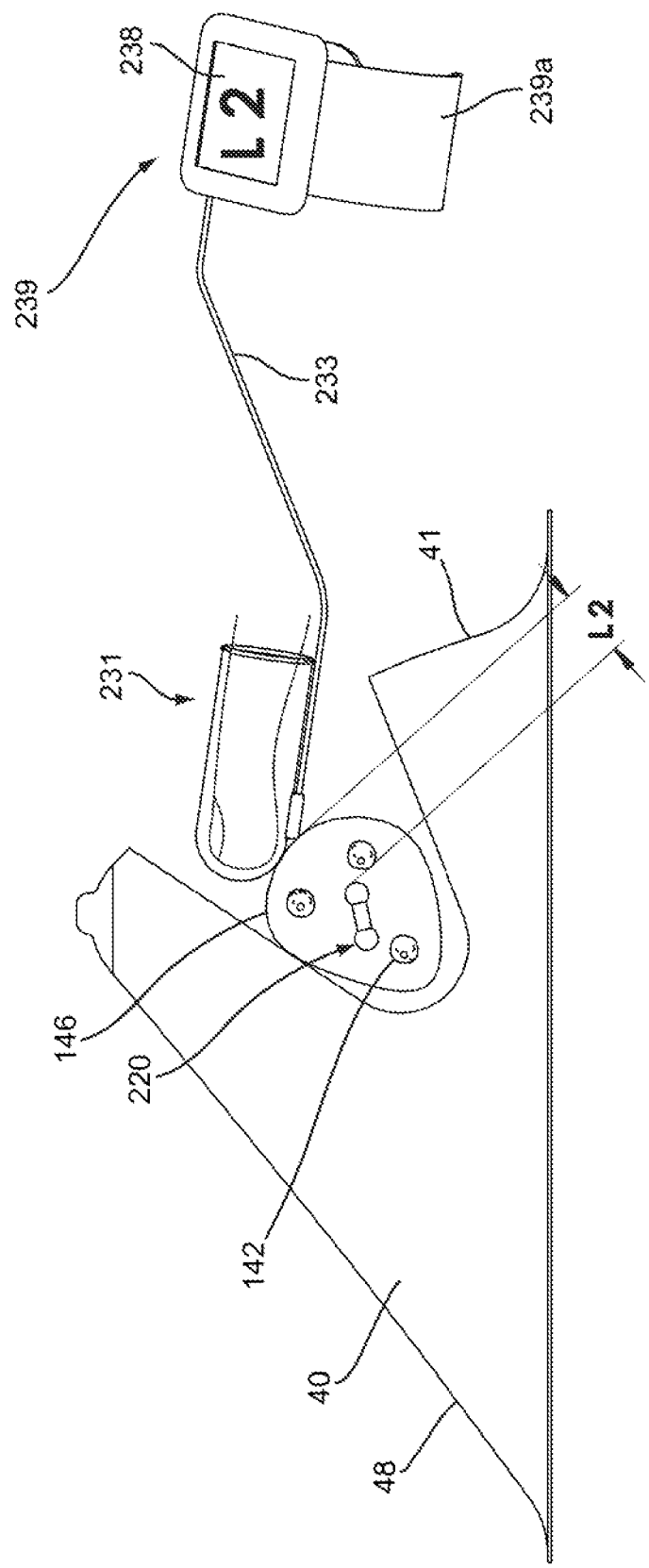

With additional reference to FIGS. 17 and 18, during use, a physician or other user may insert one of their fingers 90, e.g., their index finger or thumb, into the finger cot 231a, and the processor 239 may be activated to send and receive signals via the antenna(s) 232, similar to the previous embodiments.

As shown in FIG. 17, the finger 90 inserted into the finger cot 231a may be placed against the patient's skin 48 and distance measurements obtained to identify the distance to the marker 220. As the tissue overlying the marker 220 is dissected, the user may insert the finger 90 into the path created, as shown in FIG. 18, thereby providing direct feedback to the user of the location of the marker 220, and consequently, the lesion(s) 142, relative to the finger 90. Thus, this embodiment of the probe 231 may provide tactile feedback as well as distance measurements, which may facilitate dissection and/or removal of a tissue specimen 146 including the marker 220 and lesion(s) 142 therein. For example, as shown in FIG. 17, an initial distance measurement L1 may be obtained informing the user of the depth of dissection needed, while, as shown in FIG. 18, a distance measurement L2 may be obtained (corresponding to the desired margin), thereby informing the user that sufficient dissection has been achieved and the tissue specimen 146 may be isolated and removed, similar to the previous embodiments.

Turning to FIGS. 19-22, still another system is shown for localizing and/or accessing a target tissue region, e.g., including one or more lesions 142. Generally, the system includes a probe instrument 330, including a handheld probe 331 coupled to a processor 339, similar to the previous embodiments. For example, the probe 331 includes one or more antennas 332, and the processor 238 includes a display 338.

Figure 19:
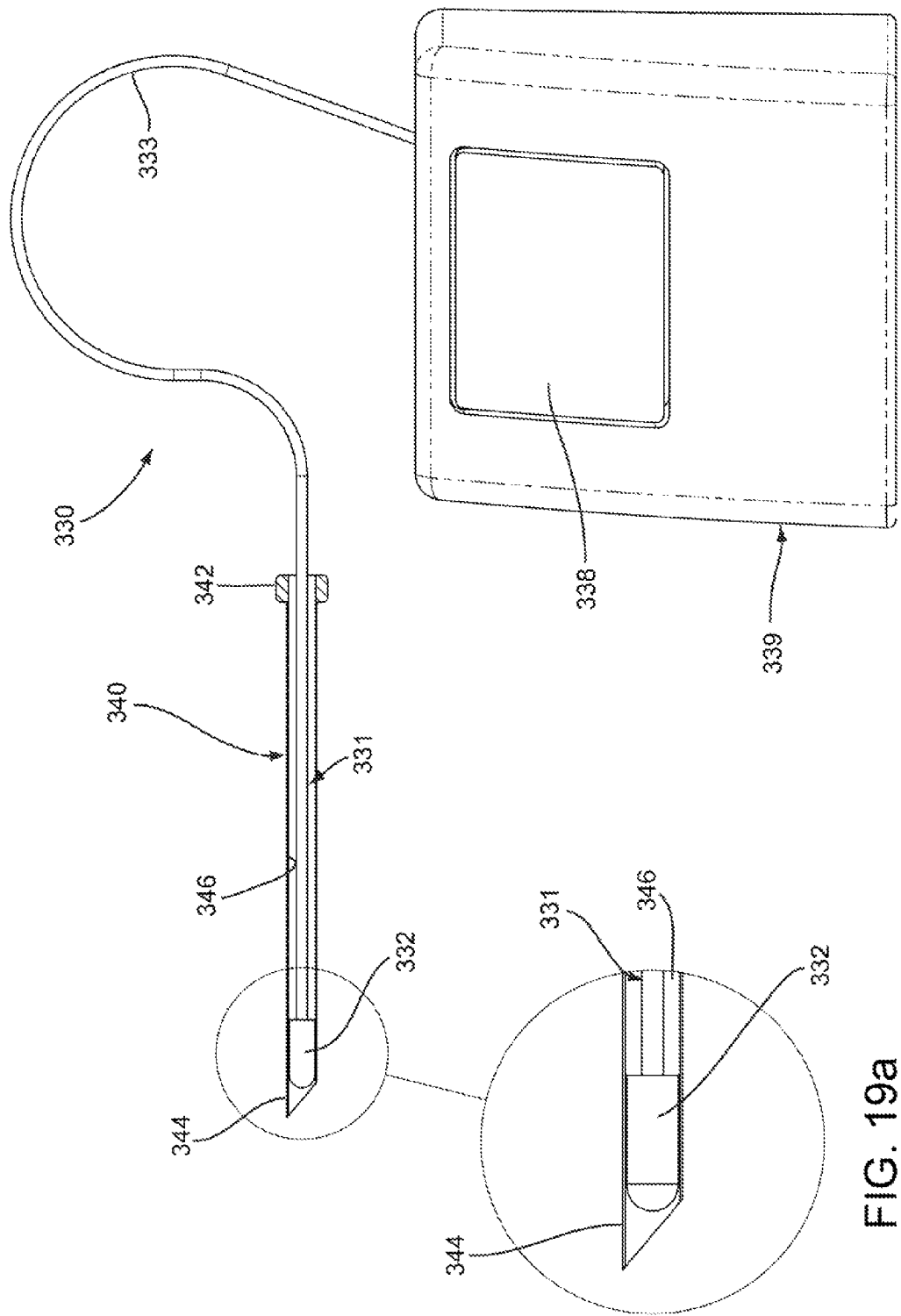
FIG. 19 is a side view of yet another exemplary embodiment of a probe instrument including a cannula carrying a probe and a controller coupled to the probe.

In addition, the system includes a cannula or other tubular member 340 that includes a proximal end 342, distal end 344, and a lumen 346 extending therebetween. The cannula 340 may be a substantially rigid tubular body having a size such that the probe 331 may be received within the lumen 346, as shown in FIG. 19. As shown, the distal end 344 may be beveled, sharpened, and/or otherwise formed to facilitate advancement directly through tissue. Alternatively, the distal end 344 may be tapered and/or rounded (not shown), e.g., such that the cannula 340 may be advanced over a needle (not shown) either before or after the needle has been introduced into the tissue 40, similar to the previous embodiments.

With reference to FIG. 19, before use, the probe 330 may be inserted into the lumen 346 of the cannula 340, e.g., such that the antenna(s) 332 are disposed immediately adjacent the distal end 344 of the cannula 340. Optionally, the cannula 340 and/or probe 331 may include one or more connectors (not shown) for releasably securing the probe 331 relative to the cannula 340, e.g., to maintain the antenna(s) 332 adjacent the distal end 344, while allowing the probe 331 to be removed when desired. In addition or alternatively, the cannula 340 may include one or more seals (not shown), e.g., within the proximal end 342 and/or distal end 344, to provide a substantially fluid-tight seal when the probe 331 is disposed within the lumen 346 and/or when the probe 331 is removed. For example, a hemostatic seal (not shown) may be provided in the proximal end 342 that may provide a seal to prevent fluid flow through the lumen 346, yet accommodate receiving the probe 331 or other instruments (not shown) therethrough.

Figure 20:
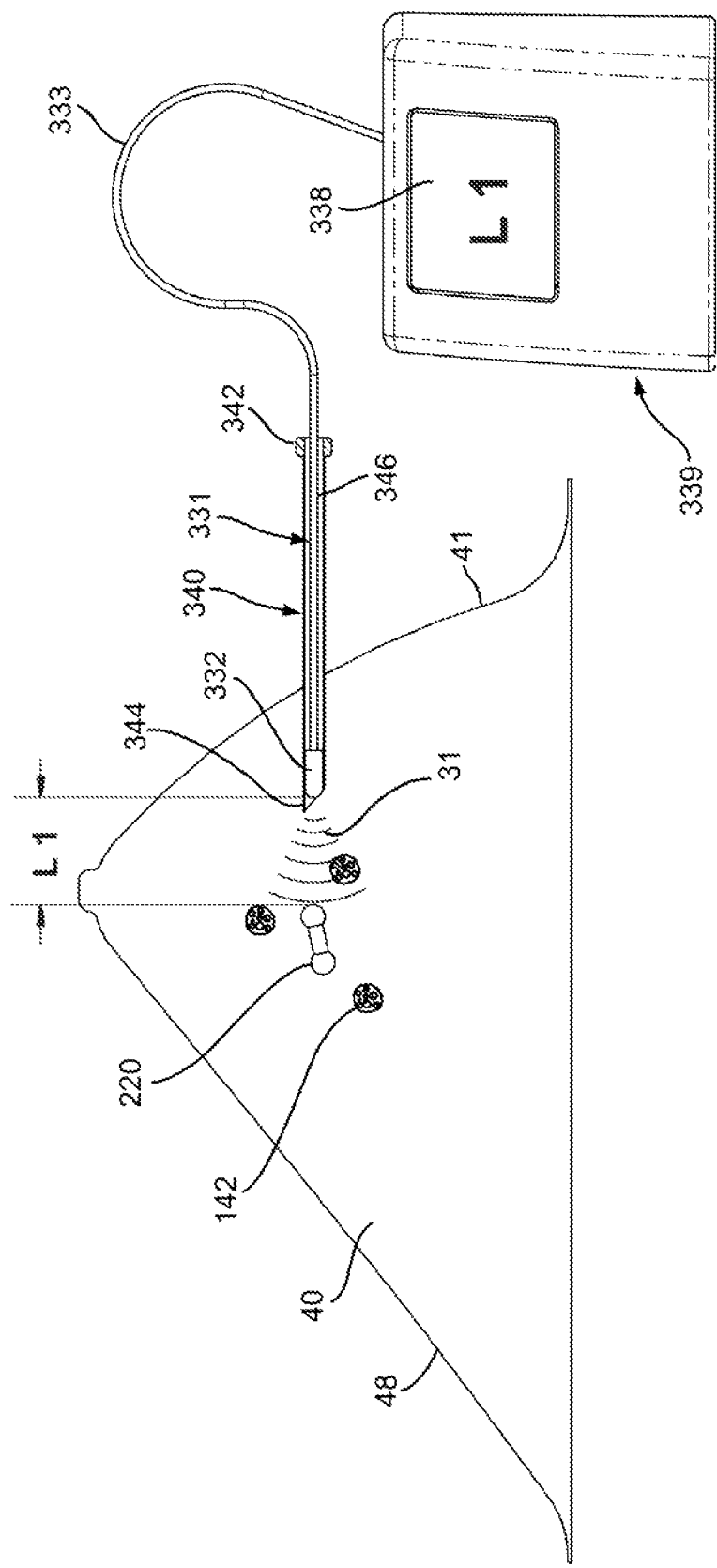
FIGS. 20-22 are cross-sectional views of a breast having a marker implanted adjacent lesions and showing a method for placing the cannula into the breast to provide access to the site of the lesions.
Figure 21:
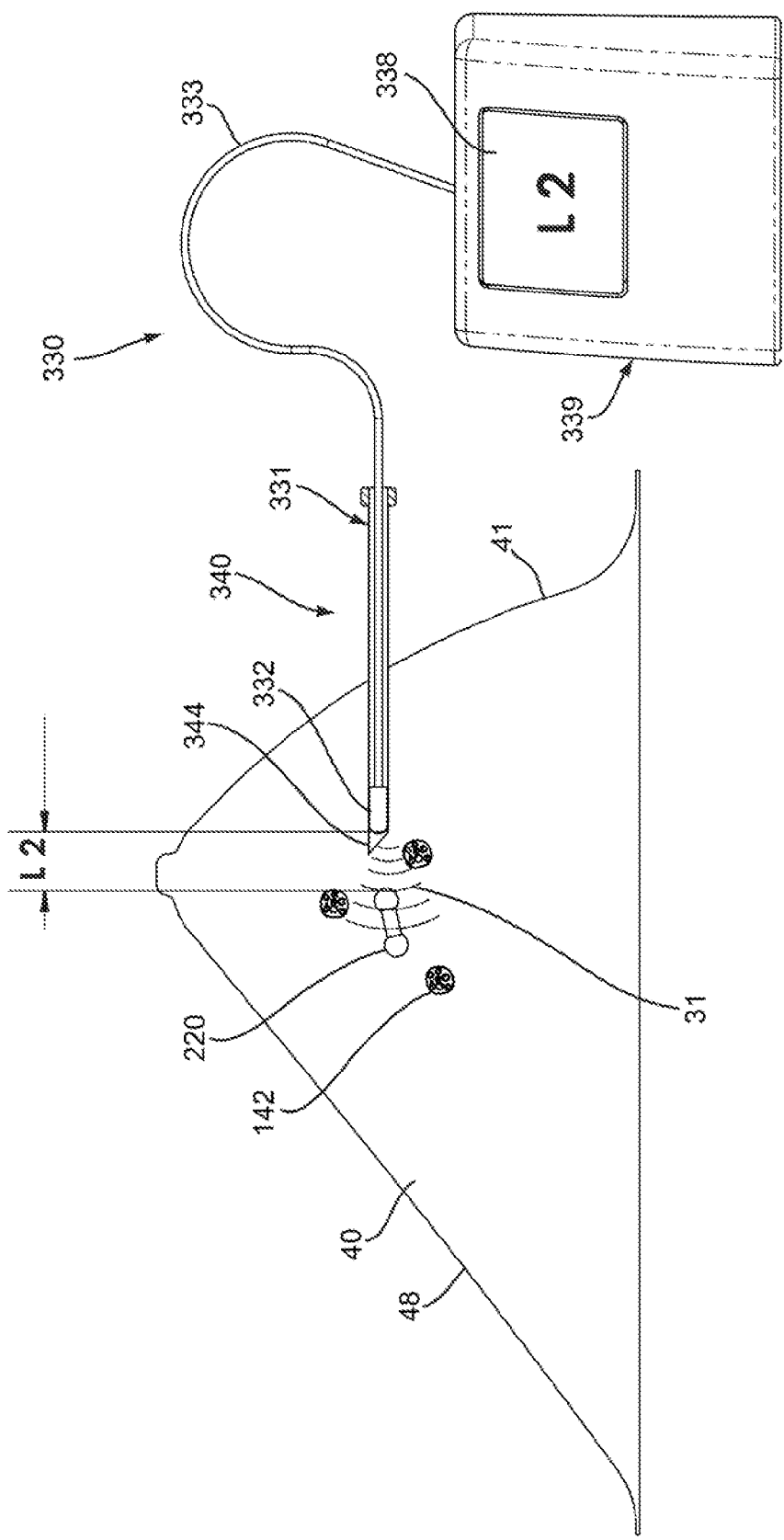

Turning to FIG. 20, during use, with the probe 331 activated and within the cannula 340, the distal end 344 of the cannula 340 may be inserted through the patient's skirt 48 and tissue 40 towards the marker 220. As shown, the probe 331 may transmit signals 31 and the display 338 of the processor 339 may provide a distance measurement L1 or other indication of the relative location of the marker 220 to the antenna(s) 332 based on the reflected signals received by the antenna(s) 332, and consequently, relative to the distal end 344 of the cannula 340. Thus, the depth of penetration and/or direction of advancement of the cannula 340 may be adjusted based upon the information provided by the probe 331 and processor 339. For example, as shown in FIG. 21, the cannula 340 may be advanced until a desired distance L2 is achieved, thereby placing the distal end 344 a desired distance away from the marker 220, e.g., within a target tissue region adjacent the lesion(s) 142.

Figure 22:
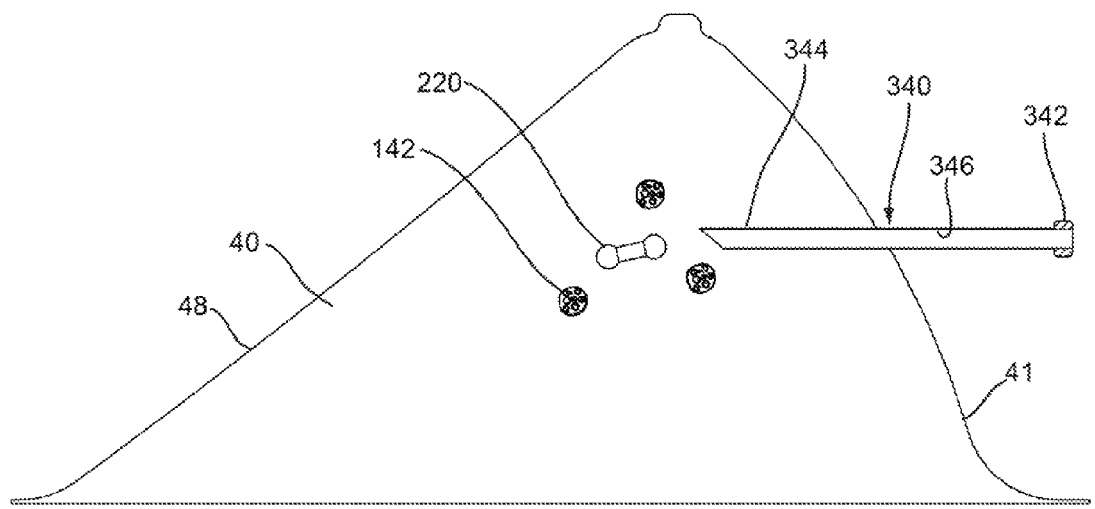

Turning to FIG. 22, with the distal end 344 of the cannula 340 placed at a desired location relative to the lesion(s) 142, the probe 331 may be removed, leaving the cannula 340 in place, as shown. The cannula 340 may thereby provide a passage for accessing the target tissue region, e.g., to perform one or more diagnostic and/or therapeutic procedure. For example, a needle or other tool (not shown) may be advanced through the lumen 346 of the cannula to perform a biopsy and/or to deliver fluids or other diagnostic or therapeutic material into the target tissue region. In addition or alternatively, one or more instruments (not shown) may be introduced through the cannula 340 for removing a tissue specimen, e.g., including the lesion(s) 142, for delivering radiation therapy, and/or other procedures. When access is no longer needed, the cannula 340 may simply be removed. Alternatively, if it is desired to relocate the cannula 340 during a procedure, the probe 331 may be reintroduced into the lumen 346 and the cannula 340 relocated within the tissue with the probe 331 providing additional guidance.

In FIGS. 11-22, markers 220 are shown, which may be implanted or otherwise placed within the tissue 40, e.g., within or otherwise adjacent the lesion(s) 142, using methods similar to those described above. As shown, the markers 220 are generally elongate bodies including relatively narrow middle stem portions between bulbous ends. The markers 220 may be formed from desired materials and/or may include surface features similar to other markers herein, which may facilitate localization of the markers 220 and/or distinguishing markers from one another.

Turning to FIGS. 23A-28C, additional embodiments of markers are shown that may be used in any of the systems and methods described herein. For example, turning to FIGS. 23A-23C, a first exemplary marker 320 is shown that includes a core wire 322 carrying a plurality of beads or segments 324. The core wire 322 may be an elongate member, e.g., a solid or hollow structure having a diameter or other maximum cross-section between about half and two millimeters (0.5-2 mm) and a length between about one and ten millimeters (1.0-10 mm). The core wire 322 may be formed from elastic or superelastic material and/or from shape memory material, e.g., stainless steel, Nitinol, titanium, and the like, such that the core wire 322 is biased to a predetermined shape when deployed within tissue, as explained further below. Alternatively, the core wire 322 may be substantially rigid such that the marker 320 remains in a fixed shape, e.g., linear or curved, as described further below.

Figure 24A:
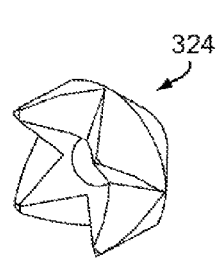
FIGS. 24A-24C are perspective, end, and side views, respectively, of a bead that may be used for making an implantable marker, such as the marker of FIGS. 23A-23D.
Figure 24B:
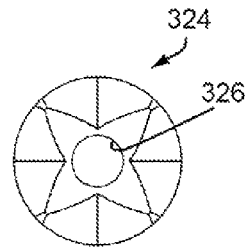
Figure 24C:
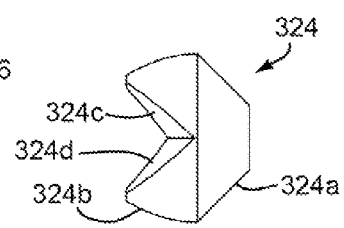

As best seen in FIGS. 24A-24C, the beads 324 may include a plurality of individual annular bodies, e.g., each defining a portion of a generally cylindrical or spherical shape. The beads 324 may be formed from desired materials similar to the previous embodiments, e.g., metals, such as stainless steel, Nitinol, titanium, and the like, plastic materials, or composite materials. The beads 324 may be formed by injection molding, casting, machining, cutting, grinding base material, and the like. In addition, a desired finish may be applied to the beads 324, e.g., by sand blasting, etching, vapor deposition, and the like.

As best seen in FIG. 24B, each bead 324 may include a passage 326 therethrough for receiving the core wire 322 (not shown, see, e.g., FIGS. 23A-23C) therethrough. The beads 324 may include shapes and/or surface features to allow the beads 324 to be nested at least partially adjacent one another when secured onto the core wire 322, yet allow the marker 320 to change shape, e.g., as the core wire 322 changes shape. In addition, the beads 324 include surface geometries to enhance reflection of electromagnetic waves, e.g., radar, and/or ultrasound waves, for example, including one or more recesses around a periphery of the beads that include multiple surfaces with adjacent surfaces defining abrupt angles, e.g., between about forty five and one hundred thirty five degrees (45-135°), or, e.g., about ninety degrees (90°). For example, as best seen in FIG. 24C, each bead 324 may include a first convex or bulbous end 324a and a second concave end 324b including flat surfaces 324d. As shown in FIG. 25B, adjacent beads 324' may define recesses 324c' between the flat surfaces 324d' on the concave end 324b' of a first bead 324 and a surface 324e' on the bulbous end 324a' of the adjacent bead 324'. The surfaces 324d' and 324e' may define abrupt corners therebetween, e.g., dihedral or trihedral corners, which may enhance detection using radar, e.g., defining angles of about ninety degrees (90°).

Optionally, as shown in FIGS. 25A and 25B, the beads 324' may include a desired surface finish 324f intended to customize reflected signals generated when electromagnetic signals strike the surfaces of the beads 324.' For example, the surface finish 324f may include a plurality of pores or dimples formed in the beads 324' and having a desired diameter and/or depth. In addition or alternatively, the surface finish 324f may define echogenic features that enhance imaging and/or identifying the beads 324' using ultrasound imaging. As explained above, the probes and processors described elsewhere herein may analyze such reflected signals to uniquely identify a particular marker, e.g., when multiple markers are implanted or otherwise placed within a patient's body.

Returning to FIGS. 23A-23C, during assembly, a plurality of beads 324 may be placed over and secured to the core wire 322 to provide a finished marker 320. For example, the core wire 322 may be inserted successively through the passages 326 in the beads 324 until beads 324 extend substantially between the ends of the core wire 322. The beads 324 may be secured to the core wire 322, e.g., by crimping individual beads 324 onto the core wire 322, crimping or otherwise expanding the ends of the core wire 322 after sliding on sufficient beads 324, bonding with adhesive, fusing, and the like. Thus, the beads 324 may be substantially permanently attached to the core wire 322 such that the beads 324 cannot move or the beads 324 may be free floating on the core wire 322, e.g., which may facilitate bending or otherwise shaping the core wire 322, and consequently the marker 320.

Alternatively, the marker 320 may be formed from a single piece of material, e.g., such that the shapes and surfaces defined by the beads 324 shown in FIG. 23A are formed in the workpiece. In this alternative, the core wire 322 may be eliminated, or a passage may be formed through the workpiece for receiving the core wire 322.

In one embodiment, the marker 320 may define a substantially fixed shape, e.g., a linear shape as shown in FIGS. 23A and 23B, or a curvilinear shape, as shown in FIGS. 23D and 26A-26C. For example, the core wire 322 of the marker 320 may be sufficiently flexible such that the marker 320 may be straightened, e.g., to facilitate loading the marker 320 into a delivery device and/or otherwise delivering the marker 320, yet the marker 320 may be biased to a curvilinear or other nonlinear shape.

As shown in FIG. 23D, the marker 320 may be biased to assume a wave configuration, e.g., a serpentine or other curved shape lying within a plane. For example, the core wire 322 may be formed from elastic or superelastic material that is shape set such that the core wire 322 is biased to the wave configuration, yet may be resiliently straightened to a linear configuration. The beads 324 may be spaced apart or otherwise nested such that the beads 324 do not interfere substantially with the transformation of the core wire 322 between the linear and wave configurations, e.g., to facilitate loading the marker 320 into a delivery device and/or introducing the marker 320 into a body.

Figure 34A:
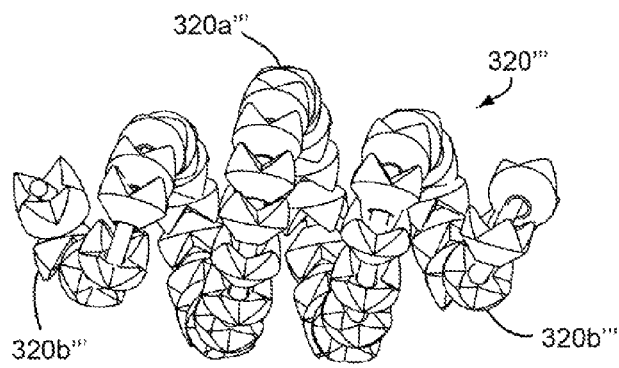
FIGS. 34A and 34B are side and end views, respectively, of yet another exemplary embodiment of a marker for implantation in tissue.
Figure 34B:
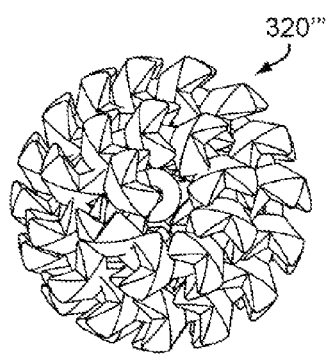
Figure 41A:
FIGS. 41A and 41B are side and end views, respectively, of still another exemplary embodiment of a marker for implantation in tissue.
Figure 41B:
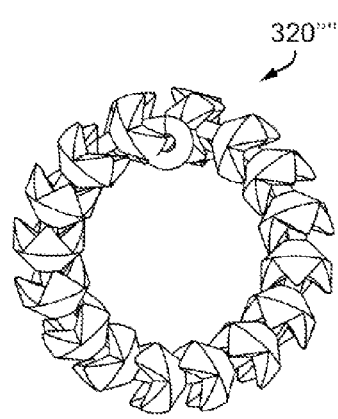

Alternatively, as shown in FIGS. 34A and 34B, a marker 320''' may be provided that is biased to assume a tapered helical shape, e.g., a prolate spheroid shape, including a relatively wide intermediate region 320a''' between tapered end regions 320b.''' Another alternative embodiment of a marker 320'''' is shown in FIGS. 41A and 41B that is biased to assume a substantially uniform diameter helical shape. One of the advantages of markers 320,''' 320'''' is that they may provide a relatively constant and/or consistent Radar Cross Section ("RCS") regardless of the reflective angle and/or position of the markers 320,''' 320'''' relative to the antenna(s) of the probe (not shown). For example, even when the markers 320,''' 320'''' are viewed along the helix axis, e.g., as viewed in FIGS. 34B and 41B, the markers 320,''' 320'''' may provide a RCS substantially similar to when viewed laterally relative to the helical axis, e.g., as viewed in FIGS. 34A and 41A. In addition, the helical configuration may provide a gap or other spacing between the formed turns of the beads 324 and its inner helical volume where embedded tissue may reside. Such a configuration may provide an enhanced marker, while minimizing obstruction, e.g., during mammography or other imaging of tissue beyond or otherwise adjacent the marker 320, e.g., compared to a contiguous surface of a solid marker, which may obstruct imaging beyond the marker.

Optionally, any of the markers described herein may be provided as a passive marker, an active marker, an active reflector, or an active transponder. For example, with reference to FIGS. 23A-23D, the marker 320 may simply be a "passive reflector," i.e., the marker 320 may simply reflect incident waves or signals striking the marker 320. The incident signals may be reflected off of the various surfaces and/or edges of the marker 320, e.g., thereby providing reflected waves or signals that may be detected by a probe, as described further elsewhere herein. One disadvantage of a passive marker is that the Radar Cross Section (RCS) may change based on the aspect angle of the antenna of the probe and the marker 320, which may cause changes in the strength of the returned signal reflected from the marker 320.

Alternatively, the marker 320 may include one or more features to provide an "active reflector," i.e., a marker 320 that includes one or more electronic circuits that modulate signals striking the marker 320 in a predetermined manner without adding external energy or power to the reflected signals. Such a marker may include an active reflector radio element that includes a modulated dipole or other type of active reflector antenna, e.g., including one or more very low power diodes and/or FET transistors that require very little current to operate. The active reflector may provide a substantially unique radar signal signature in an embedded tissue environment that may be detected and identified by a probe. In addition, the active reflector may provide a relatively larger signal return to the probe, e.g., thereby maintaining a target RCS regardless of antenna aspect.

For example, the marker 320 may include one or more circuits or other elements (not shown) coupled to or embedded in the marker 320 that may modulate incident waves or signals from the probe. In an exemplary embodiment, a nanoscale semiconductor chip may be carried by the marker 320 that does not include its own energy source and therefore merely processes and modulates the signals when they are received and reflected off the marker 320. Exemplary embodiments of active reflectors that may be provided on a marker are disclosed in U.S. Pat. No. 6,492,933, the entire disclosure of which is expressly incorporated by reference herein.

Figure 57A:
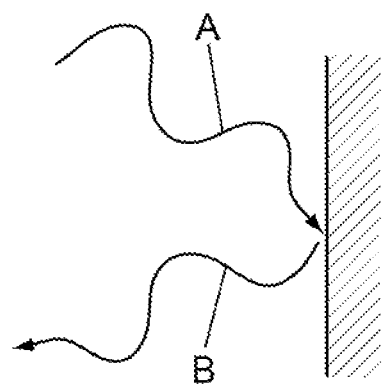
Figure 57B:
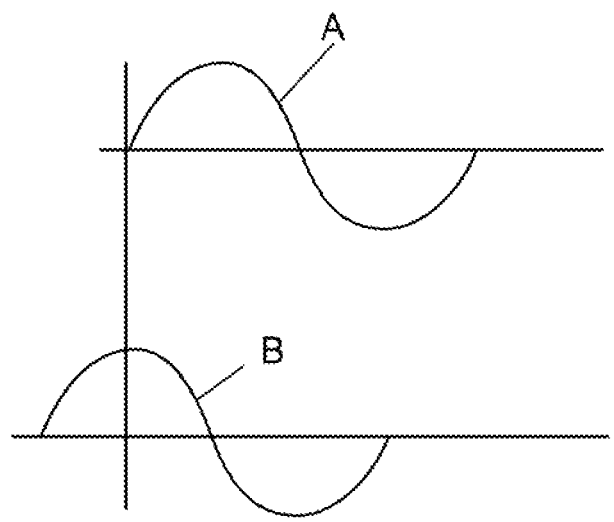
FIG. 57B shows a phase shift between the incident signal and the reflected signal.

FIGS. 57A and 57B show an example of modulation of a reflected signal B relative to an incident signal A that may be achieved using an active reflector. Incident signal A may represent waves or signals transmitted by a probe (not shown), such as any of those described elsewhere herein. As shown in FIG. 57A, the incident signal A may strike and be reflected off of a surface, e.g., of any of the markers described herein, resulting in a reflected signal B. With a passive reflector, the surface of the marker may simply reflect the incident signal A, and therefore the reflected signal B may have similar properties, e.g., bandwidth, phase, and the like, as the incident signal A.

In contrast, with an active reflector, the marker may modulate the incident signal A in a predetermined manner, for example, to change the frequency and/or phase of the reflected signal B. For example, as shown in FIG. 57B, the circuit on the marker may change an ultrawide broadband radar incident signal A into a relatively narrow band reflected signal B, e.g., between about one and ten GigaHertz (1-10 GHz), that also includes a predetermined phase shift. The relatively narrow band reflected signal B may enhance the RCS of the marker and thereby enhance detection by the probe.

In addition, as shown in FIG. 57B, the phase of the reflected signal B has been modulated by ninety degrees (90°) relative to the incident signal A. If the marker is unique in this phase shift, the phase shift may facilitate the probe identifying and distinguishing the marker from other structures, e.g., other markers having a different phase shift, tissue structures, and the like. For example, if multiple markers are to be implanted in a patient's body, each marker's circuit may be configured to impose a different phase shift (e.g., +90°, +180°, −90°, and the like) and/or bandwidth in the reflected signal. Thus, the probe may be able to easily identify and distinguish the markers from each other and/or from other structures in the patient's body.

One of the advantages of active reflectors is that the circuit does not require its own power source. Thus, the size of the circuit may be substantially reduced and, if desired, the marker may be implanted within a patient's body for an extended or even indefinite period of time, yet the marker may respond to signals from a probe to facilitate locating and/or identifying the marker.

In a further alternative, an "active marker" may be provided that includes one or more features that generate detectable energy in response to an excitation energy reference. Examples of such active markers are disclosed in U.S. Pat. No. 6,363,940, the entire disclosure of which is expressly incorporated by reference herein.

In still a further alternative, an active transponder may be provided, e.g., that retransmits or "transponds" the MIR probe's energy providing for a uniqueness of radar signal signature in an embedded tissue environment. The active transponder may include one or more electronic circuits embedded in or carried by the marker and including an internal energy source, e.g., one or more batteries, capacitors, and the like. In an exemplary embodiment, the active transponder may include a microwave receiver and/or transmitter, a data processing and storage element, and a modulation system for the returned signal. The active transponder may generate microwave energy in response to excitation microwave energy emitted by the probe, e.g., to provide a larger signal return to the probe than would be possible with only a passive marker. For example, the marker may generate RF energy including formatted data in response to a unique radar signature and/or frequency from the probe. In an exemplary embodiment, the active transponder may be quadrature modulated to emit a single side band ("SSB") signal in either the Upper Sideband Band ("USB") or the Lower Sideband ("LSB") of the MIR radar. Such a transponder may provide the possibility of multi-channel operations across the RF spectrum.

Figure 29A:
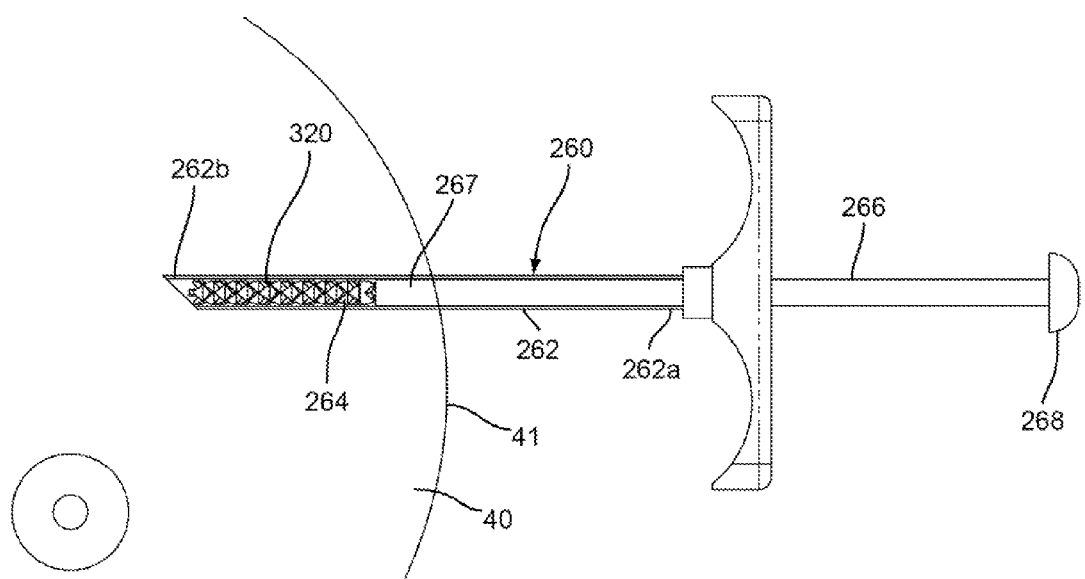
FIGS. 29A and 29B are side views of an exemplary embodiment of a delivery cannula being used to deliver the marker of FIG. 25 into a breast.
Figure 29B:
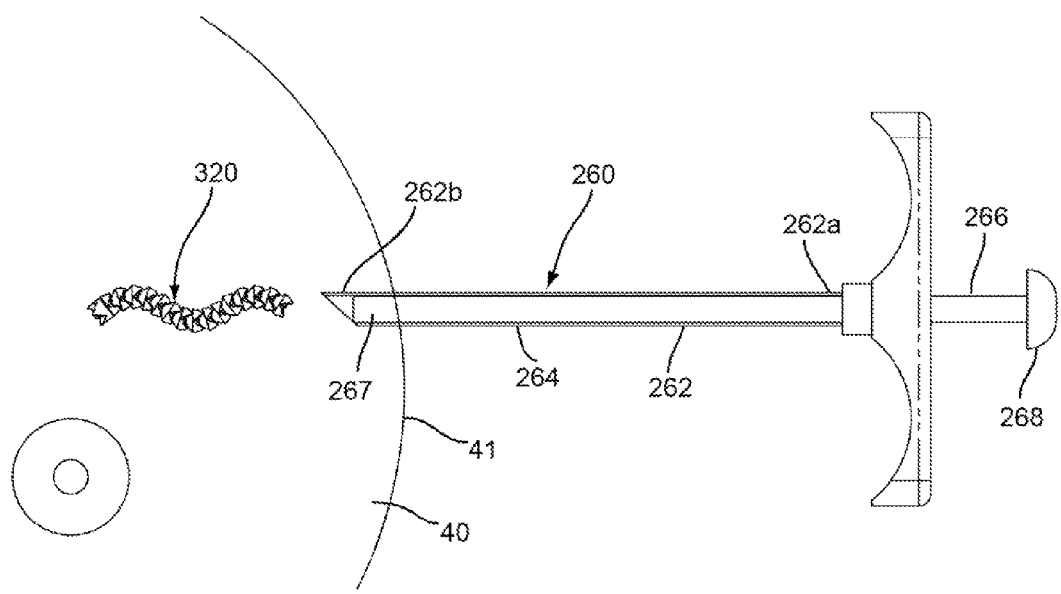

Turning to FIGS. 29A and 29B, a delivery device 260 may be provided that includes a shaft 262 including a proximal end 262a and a distal end 262b sized for introduction through tissue into a target tissue region, e.g., within breast 41, and carrying a marker 320 (or optionally multiple markers, not shown). The delivery device 260 may include a lumen 264 extending between the proximal and distal ends 262a, 262b of the shaft 262, and a pusher member 266 slidable within the shaft 262 for delivering the marker 320 of FIGS. 23A-23D from the lumen 264. As shown, the distal end 262b of the shaft 262 may be beveled and/or otherwise sharpened such that the shaft 262 may be introduced directly through tissue. Alternatively, the delivery device 260 may be introduced through a cannula, sheath, or other tubular member (not shown) placed through tissue, e.g., as described elsewhere herein. Optionally, the distal end 262b may include a band or other feature, e.g., formed from radiopaque, echogenic, or other material, which may facilitate monitoring the distal end 262b during introduction, also as described elsewhere herein.

As shown in FIG. 29A, the pusher member 266 includes a distal end 267 disposed within the lumen 264 adjacent the marker 320 and a plunger or other actuator 268 for advancing the distal end 267 to push the marker 320 from the lumen 264. As shown in FIG. 29B, once the distal end 264 of the delivery device 260 has been advanced to a desired location within tissue 40, the shaft 262 may be retracted relative to the plunger 268 to eject the markers 320 successively from the lumen 264. Alternatively, a trigger device or other automated actuator (not shown) may be provided on the proximal end 262b of the shaft 262 to delivery the marker 320 from the distal end 262b.

Turning to FIGS. 26A-26C, an alternative embodiment of a marker 320" is shown that is generally similar to the marker 320 shown in FIGS. 23A-23D, e.g., including a core wire 322" carrying a plurality of beads 324." Unlike the marker 320, however, the core wire 322" is biased to a helical shape, e.g., such that the marker 320" is biased to a helical configuration as shown. Thus, the marker 320" may be straightened, e.g., to facilitate loading into a delivery device, such as the delivery device 260 shown in FIGS. 29A and 29B, yet may be biased to return resiliently to the helical configuration.

In an alternative embodiment, any of the markers 320, 320,' or 320" may be formed at least partially from shape memory material, e.g., such that the markers may be biased to assume a predetermined configuration when heated to a target temperature. In addition or alternatively, any of the markers may be formed from bioabsorbable material, e.g., gelatin, PLA, and/or PGA material, as described elsewhere herein.

For example, with reference to the marker 320 of FIG. 24, the core wire 322 may be formed from a shape memory material, e.g., Nitinol, such that the core wire 322 is in a martensitic state at or below ambient temperature, e.g., twenty degrees Celsius (20° C.) or less, and an austenitic state at or above body temperature, e.g., thirty seven degrees Celsius (37° C.) or more. In the martensitic state, the core wire 322 may be relatively soft and malleable, e.g., such that the marker 320 may be straightened and loaded into the delivery device 260 of FIGS. 29A and 29B. The shape memory of the core wire 322 may be heat set or otherwise programmed into the material such that, when the core wire 322 is heated to the target temperature, the core wire 322 may become biased to the wave, helical, or other nonlinear shape. Thus, even if the marker 320 is bent, straightened, or otherwise deformed from its desired deployment configuration while in the martensitic state, the marker 320 may automatically become biased to assume the deployment configuration once introduced into a patient's body or otherwise heated to the target temperature.

Turning to FIGS. 27A-27C, another exemplary embodiment of a marker 420 is shown. Similar to the marker 320, the marker 420 includes a core wire 422 carrying a plurality of beads or segments 424. Each of the beads 424 includes a plurality of recesses 424c, e.g., defining dihedral or trihedral corners, for enhancing reflection of signals from a probe (not shown), such as those described elsewhere herein. The core wire 422 and beads 424 may be manufactured and assembled similar to the previous embodiments, e.g., such that the beads 424 are free to rotate on or are fixed to the core wire 422. The recesses 424c may be formed entirely in each respective bead 424 or may be defined by cooperating surfaces of adjacent beads (not shown), similar to the previous embodiments. The recesses 424c may define substantially flat or curved surfaces that meet at abrupt edges defining corners that may enhance radar detection.

Optionally, as shown in FIGS. 28A-28C, alternative embodiments of spherical markers 520, 520,' 520" are shown that include recesses 524c, 524c,' 524c" having different shapes and/or configurations. The recesses 524c, 524c,' 524c" may generate reflected signals that are substantially different than one another, e.g., such that a processor of a probe may be able to distinguish different markers based on the different reflected signals, as described above. In the embodiments shown in FIGS. 28A-28C, the markers 520, 520,' 520" are formed from a single piece of material and do not include a core wire and multiple beads. It will be appreciated that a core wire and multiple beads may be provided, if desired, for the markers 520, 520,' 520" and/or that the marker 420 of FIGS. 27A-27C may be formed from a single piece of material, if desired.

Turning to FIGS. 30A-31B, another embodiment of a delivery device 360 is shown that may be used for delivering a marker 320, such as the marker 320 shown in FIGS. 23A-23D, but which alternatively may be any of the markers described elsewhere herein. Generally, the delivery device 360 includes a needle or other tubular shaft 362 including a proximal end 362a and a distal end 362b sized for introduction through tissue into a target tissue region, e.g., within breast 41, and a lumen 364 extending between the proximal and distal ends 362a, 362b. The delivery device 360 also includes a pusher member 366 slidable within the shaft 362 for delivering the marker 320 from the lumen 364. As shown, the distal end 362b of the shaft 362 may be beveled and/or otherwise sharpened such that the shaft 362 may be introduced directly through tissue. Alternatively, the delivery device 360 may be introduced through a cannula, sheath, or other tubular member (not shown) placed through tissue, e.g., as described elsewhere herein. Optionally, the distal end 362b may include a band or other feature, e.g., formed from radiopaque, echogenic, or other material, which may facilitate monitoring the distal end 362b during introduction, e.g., using x-ray or ultrasound imaging, also as described elsewhere herein.

As shown in FIGS. 30B and 31B, the pusher member 366 includes a distal end 367 disposed within the lumen 364, e.g., initially adjacent the marker 320 as shown in FIG. 30B. The pusher member 366 may be substantially stationary relative to a handle 370 of the delivery device 360, while the shaft 362 may be retractable, e.g., for exposing the marker 320, as described further below. For example, as shown in FIG. 30B, a proximal end 366a of the pusher member 366 may be fixed to a pusher holder 372 mounted within the handle 370.

The shaft 362 may coupled to shaft holder 374, which is slidable within the handle 370. For example, the shaft holder 374 may be slidable axially from a first or distal position, shown in FIG. 30B, to a second or proximal position, shown in FIG. 31B. Thus, with the shaft holder 374 in the first position, the distal end 367 of the pusher member 366 may be offset proximally from the distal end 362b of the shaft 362, thereby providing sufficient space within the shaft lumen 364 to receive the marker 320, as shown in FIG. 30B. When the shaft holder 374 is directed to the second position, the shaft 362 is retracted until the distal end 362b of the shaft 362 is disposed adjacent the distal end 367 of the pusher member 366, e.g., as shown in FIG. 31B. The distal end 367 of the pusher member 366 prevents the marker 320 from migrating proximally during this retraction of the shaft 362 such that the marker 320 is consequently deployed from the lumen 364 of the shaft 362, as shown in FIGS. 33 and 33A.

The shaft holder 372 and shaft 362 may be biased to the second position, but may be selectively retained in the first position, e.g., to allow a marker 320 to be loaded into and delivered using the delivery device 360. For example, as shown in FIGS. 30B and 31B, the handle 370 includes a spring or other mechanism received in a recess 378 in the housing and abutting the shaft holder 374. In the first position, the spring 376 is compressed, as shown in FIG. 30B, while in the second position, the spring 376 is relaxed or in a lower potential energy state, as shown in FIG. 31B.

The handle 370 also includes an actuator for selectively retaining and releasing the shall holder 374 and shaft 362 in the first position. For example, as shown in FIG. 30B, with the shaft holder 374 in the first position, the shaft holder 374 may be rotated within the handle 370 until a proximal end 374a of the shaft holder 374 abuts or otherwise engages a distal end 372a of the pusher holder 372. Alternatively, the handle 370 may include one or more other features (not shown) that may selectively engage the shaft holder 374 in the first position. As shown in FIG. 31B, if the shaft holder 374 is rotated within the handle 370 to disengage the proximal end 374a from the distal end 372a of the pusher holder 372, the proximal end 372a may be free to travel proximally within the handle 370. Thus, once the shaft holder 374 is rotated, the spring 376 may automatically direct the shaft holder 374 proximally, thereby deploying the marker 320. It will be appreciated that other actuators, e.g., releasable detents or locks may be provided on the handle 370 and/or shaft holder 374 that may interact to releasably secure the shaft 362 in its advanced position and allow the shaft 362 to automatically retract when the actuator is activated.

Turning to FIGS. 32 and 33, the delivery device 360 may be used to deliver a marker 320 into a breast 41 or other tissue structure, e.g., within a target tissue region including one or more lesions 142, similar to the previous embodiments. Once the marker 320 is delivered, the marker 320 may be used to localize the target tissue region, e.g., using any of the systems and methods described elsewhere herein.

For example, in an exemplary procedure, the marker 320 may be placed within a target tissue region during a biopsy procedure. For example, the delivery device 360 and marker 320 may be introduced through a biopsy needle (not, shown, such as the Mammotome device from Devicor Inc. or the A-Track device from Hologic Corp.). Such a needle may used to perform a biopsy or otherwise create a tissue tract and/or extract a tissue sample from a target tissue region. In this embodiment, the shaft 322 of the delivery device 360 may be substantially rigid or flexible, if desired.

For example, similar to the method shown in FIGS. 32 and 33, the marker 320 may advanced through a biopsy needle (not shown) and implanted within the tissue 40, e.g., within the resulting biopsy tract or cavity and/or the surrounding tissue. For example, after performing a biopsy or otherwise obtaining a tissue specimen from the tissue 40, the marker 320 may be deployed within the biopsy cavity, e.g., using x-ray imaging and/or ultrasound, similar to other embodiments herein, to identify the location of the biopsy. The self-boring nature of the marker 320 as it is deployed and returns towards its helical configuration may embed or otherwise secure the marker 320 relative to the surrounding tissue 40, thereby preventing or reducing subsequent migration.

Thus, the marker 320 may provide an accurate indication of the extraction site of a tissue sample. If, upon further examination, the tissue sample is cancerous, the marker 320 may provide guidance to subsequently localize the site and/or provide surgical guidance for removing tissue surrounding the sample site, similar to other embodiments herein. If the tissue sample, the marker 320 may remain indefinitely in the tissue 40. Alternatively, if one or more portions of the marker 320 are formed from bioabsorbable material, the bioabsorbable portions may automatically be absorbed by the patient's body over time. For example, the entire marker 320 may be absorbable, or alternatively only the beads 324 may be bioabsorbable. In this alternative, the beads 324 may be absorbed over time (since the enhanced echogenicity and/or RCS of the beads 324 may no longer be needed), leaving the core wire 322 within the target tissue region. Thus, the core wire 322 may remain to be visualized using mammography or other imaging, but may have a smaller profile than the original marker 320, e.g. reduced by up to half, thereby minimizing obstruction of surrounding healthy tissue during subsequent mammography or other imaging.

Figure 35:
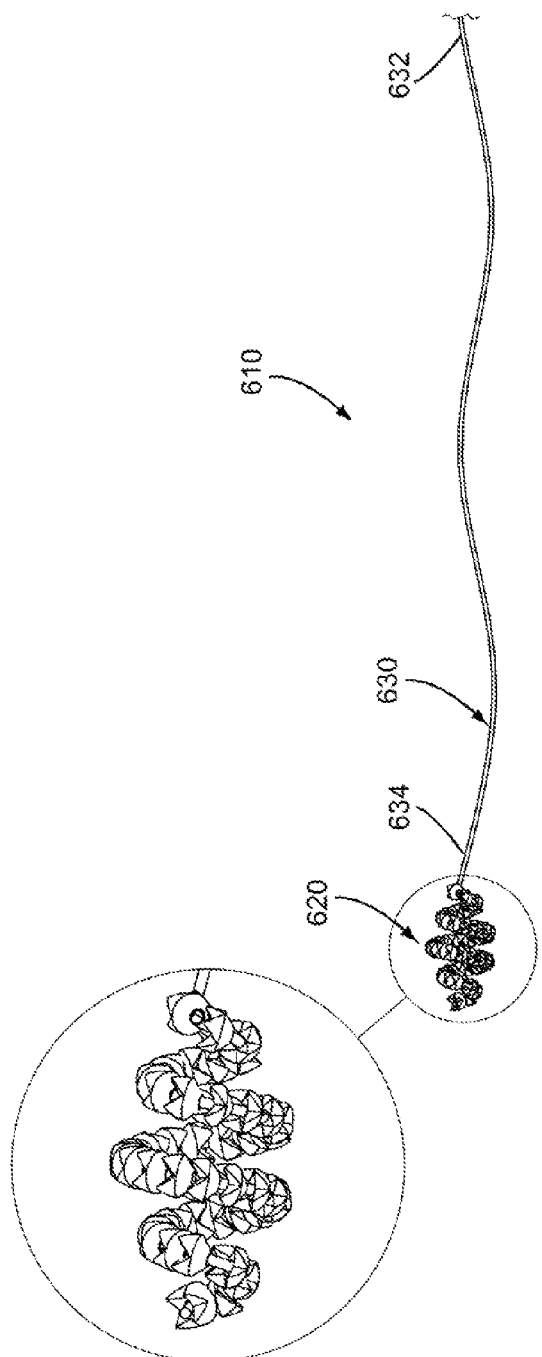
FIG. 35 is a side view of an alternative embodiment of a marker device including the marker of FIGS. 34A and 34B coupled to an elongate tether.

Turning to FIG. 35, still another embodiment of a marker device 610 is shown that includes a marker 620 coupled to a tether or other elongate element 630. The tether 630 may be a suture, e.g., formed from bioabsorbable or non-absorbable material, a wire, and the like, e.g., formed from flexible, rigid, or malleable material, and having sufficient length to extend out of a patient's body when the marker is introduced into a target tissue region. The marker 620 may be similar to the marker 320''' shown in FIGS. 34A and 34B or any of the other embodiments described elsewhere herein, and may be releasably or substantially permanently attached to a distal end 634 of the tether 630, e.g., similar to the localization wire described elsewhere herein. Adding an elongate tether 630 extending from a marker 620 may provide an additional reference of the location of the marker 620 when implanted within tissue. For example, the tether 630 may help guide a surgeon to the exact location of the marker 620 during lumpectomy surgery and/or may confirm the presence of the marker 620 inside a removed tumor volume. The tether 630 may also be used to place a tag to help identify the orientation of the marker 620 within a target tissue region, and may be left in place or removed, as desired.

Turning to FIGS. 36-41, a delivery device 660 and method are shown for implanting the marker device 610 within a target tissue region, e.g., for implanting the marker 620 within a non-palpable lesion 142 within a breast 41. Similar to previous embodiments, the delivery device 660 includes a shaft 262 including a proximal end 262a and a distal end 262b sized for introduction through tissue into a target tissue region, e.g., within breast 41, and carrying the marker device 610. The delivery device 660 may include a lumen 664 extending at least partially between the proximal and distal ends 662a, 662b of the shaft 662, and a pusher member 666 slidable within the shaft 662 for delivering the marker 620 from the lumen 664. As shown, the distal end 662b of the shaft 662 may be beveled and/or otherwise sharpened such that the shaft 662 may be introduced directly through tissue. Alternatively, the delivery device 660 may be introduced through a cannula, sheath, or other tubular member (not shown) placed through tissue, e.g., as described elsewhere herein. Optionally, the distal end 662b may include a band or other feature, e.g., formed from radiopaque, echogenic, or other material, which may facilitate monitoring the distal end 662b during introduction, also as described elsewhere herein.

Figure 36:
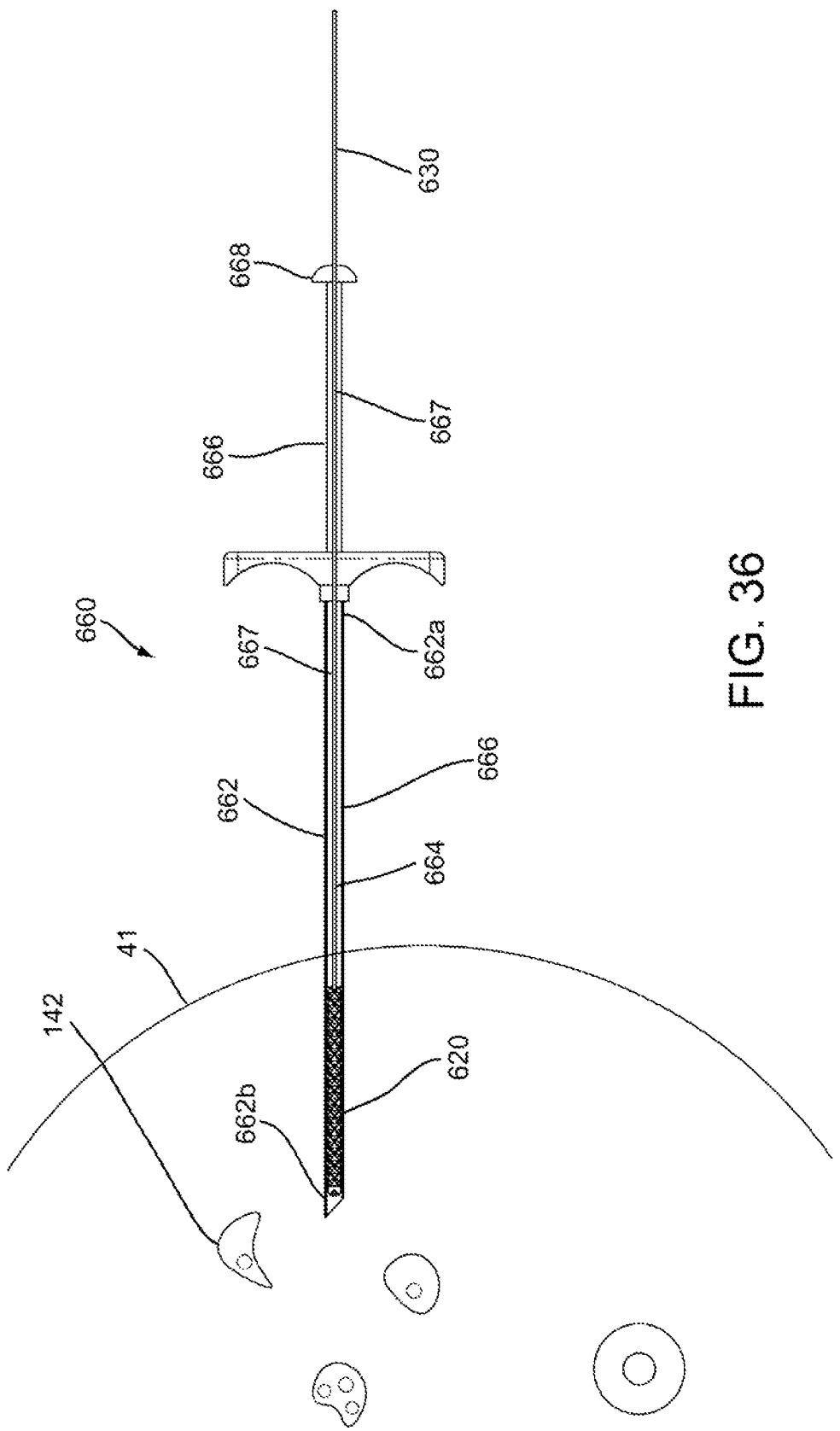

As shown in FIG. 36, the pusher member 666 includes a lumen 667 for slidably receiving the tether 630 therethrough. Thus, during manufacturing or at any time before use, the marker device 610 may be loaded in the delivery device 660 such that the marker 620 is disposed within the lumen 664 adjacent the distal end 662b and the tether 630 extends through the lumen 667 of the pusher member 666 and out a plunger 668 coupled to the pusher member 666. If the marker is 620 is biased to a helical or other shape, the marker 620 may be straightened as it is loaded into the shaft 662, as shown in FIG. 36. The marker device 610 may be implanted before a lumpectomy procedure, to replace a wire localization procedure, or at the time of a biopsy. Alternatively, the marker device 610 may be delivered through a core needle biopsy instrument or a vacuum assisted core needle system (not shown).

Figure 37:
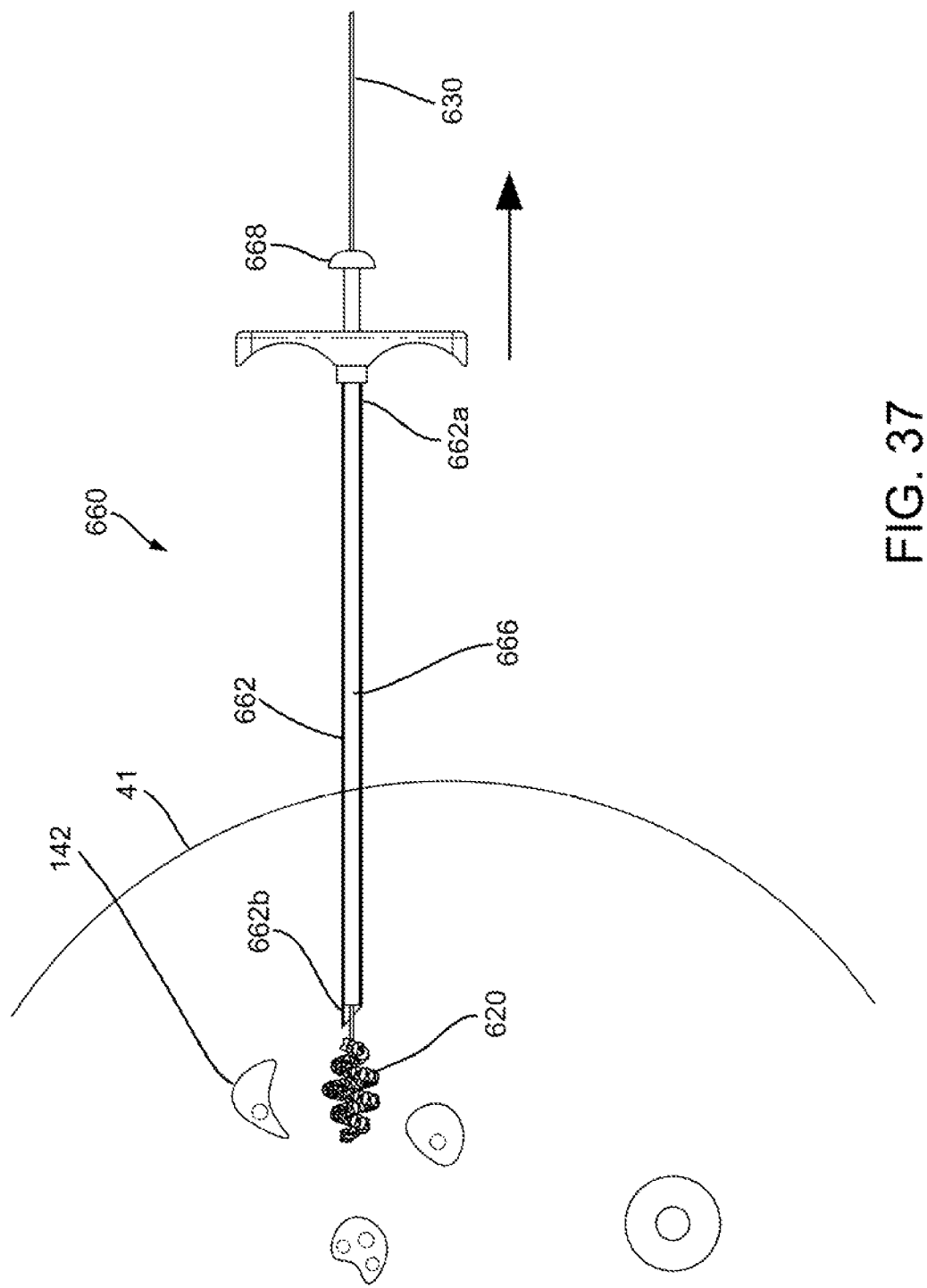
Figure 38:
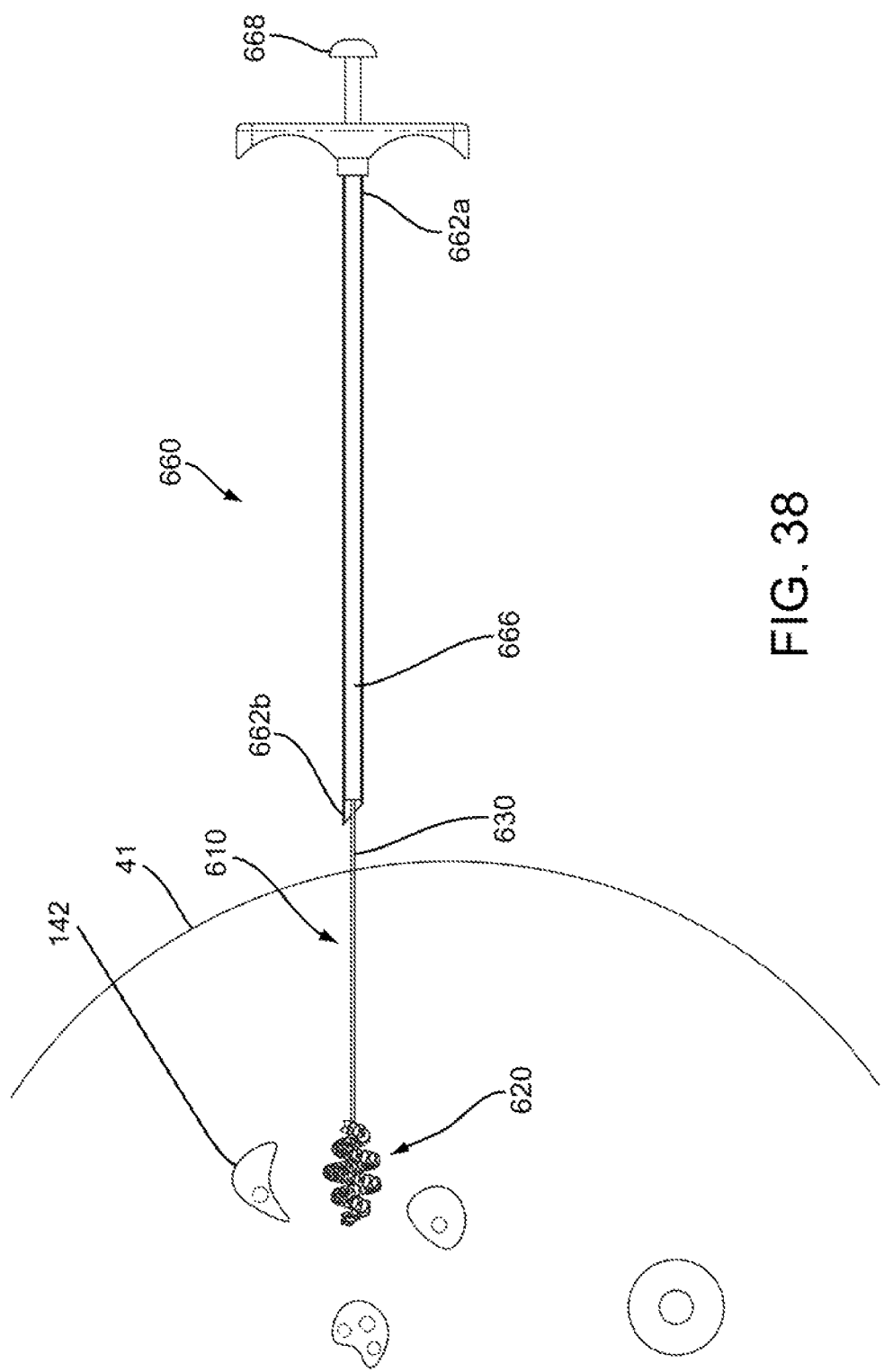
Figure 44:
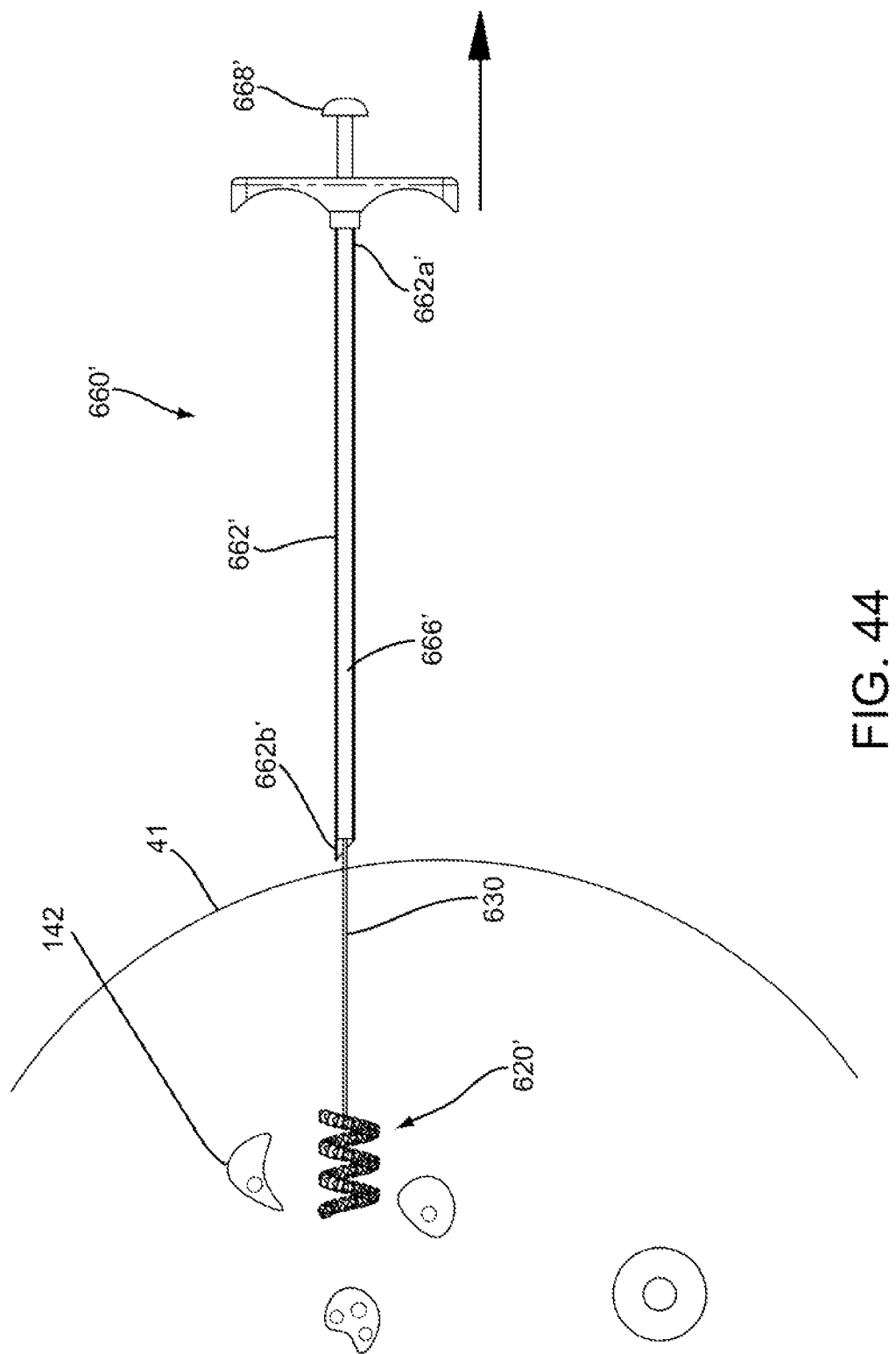

For example, during a procedure, the distal end 662b may be inserted through tissue into the target tissue region, e.g., within lesion(s) 142, as shown in FIG. 36. Once the distal end 662b of the delivery device 660 has been advanced to a desired location within tissue, the shaft 662 may be retracted relative to a plunger 668 coupled to the pusher member 666 to deliver the marker 620 from the lumen 664, as shown in FIG. 37. As shown, the marker 620 may automatically and/or resiliently change shape upon deployment, e.g., returning towards the tapered helical shape shown in FIG. 37. Turning to FIG. 38, the delivery device 660 may be withdrawn from the patient's body leaving the marker 620 within the target tissue region, e.g., within lesion(s) 142. The tether 630 may simply slide through the pusher member 666 until the end is exposed from the breast 41, e.g., as shown in FIG. 39.

Optionally, as shown in FIG. 40, the tether 630 may be separated from the marker 620, leaving the marker 620 in place within the lesion(s) 142. For example, the tether 630 may include a weakened region (not shown) immediately adjacent the marker 620, which may be broken upon application of a predetermined tension. Alternatively, the tether 630 may include a threaded distal end 634 or other connectors that may be released from the marker 620, e.g., by rotating the tether 630 to unthread the distal end 634 from the marker 620. Alternatively, the tether 630 may remain attached to the marker 620 during a subsequent lumpectomy or other procedure.

Figure 42:
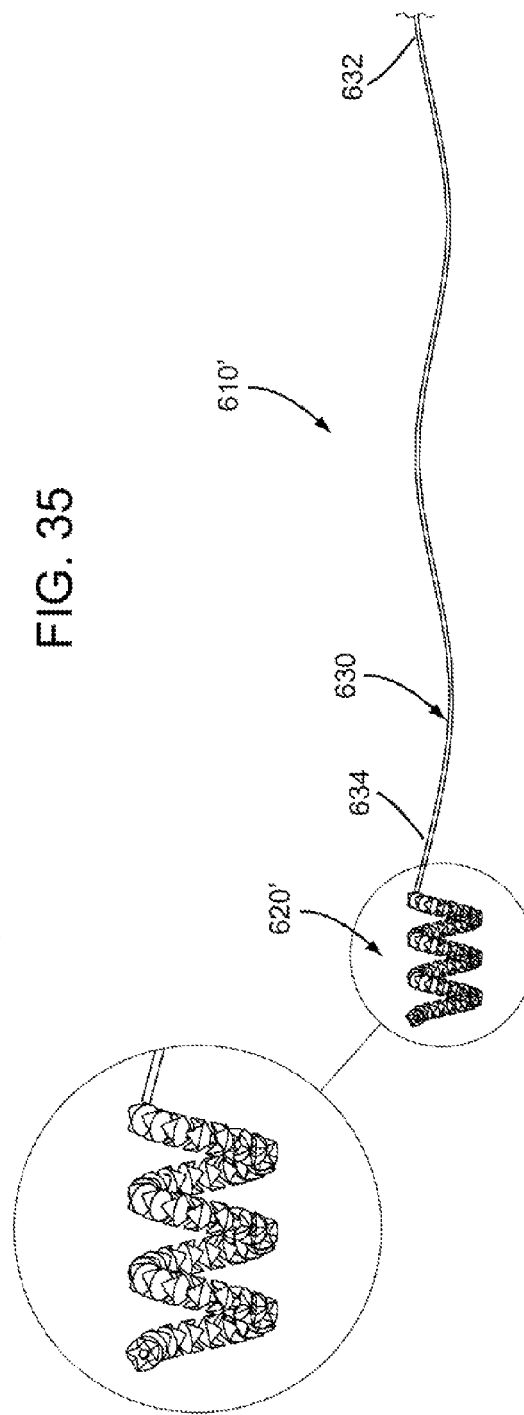
FIG. 42 is a side view of an alternative embodiment of a marker device including the marker of FIGS. 36A and 36B coupled to an elongate tether.

Turning to FIG. 42, another exemplary embodiment of a marker device 610' is shown that is generally similar to the marker device 610, i.e., including a tether 630 and a marker 620.' However, the marker 620' may be similar to the marker 320"" shown in FIGS. 41A and 41B. FIGS. 43-46 show an exemplary embodiment of a delivery device 620' and method for implanting the marker device 610,' which are generally similar to that shown in FIGS. 36-40.

Figure 47A:
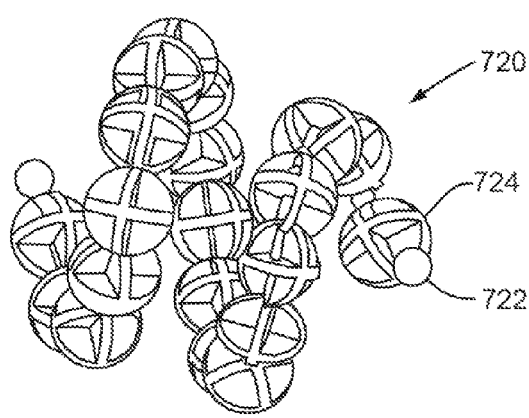
FIGS. 47A and 47B are a side and end views of another exemplary embodiment of a marker including a plurality of beads carried on a core wire and defining a wave shape in its deployed configuration.
Figure 47B:
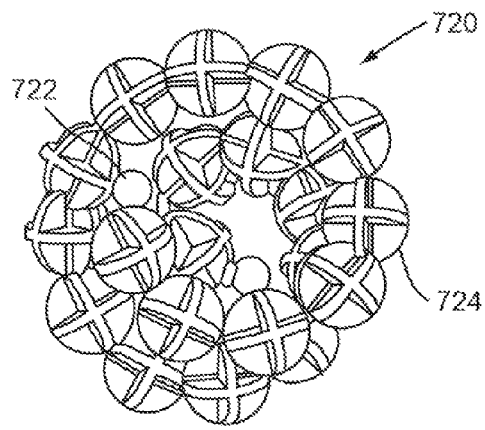

Turning to FIGS. 47A and 47B, another embodiment of a marker 720 is shown that includes a core wire 722 carrying a plurality of beads or segments 724. The core wire 722 may be an elongate member, e.g., a solid or hollow structure, formed from elastic or superelastic material and/or from shape memory material, e.g., stainless steel, Nitinol, titanium, and the like, such that the core wire 322 is biased to a predetermined shape when deployed within tissue, similar to other embodiments herein.

Figure 48A:
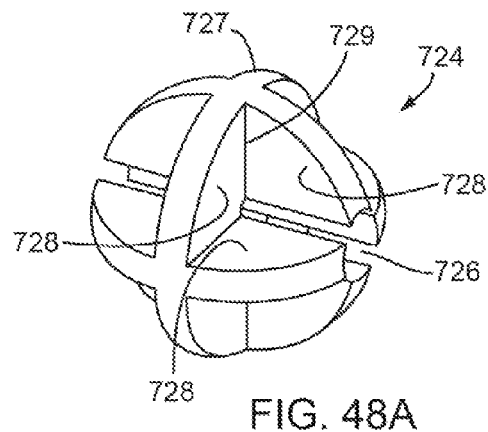
FIGS. 48A-48C are perspective, end, and side views, respectively, of a bead that may be used for making an implantable marker, such as the marker of FIGS. 47A and 47B.
Figure 48B:
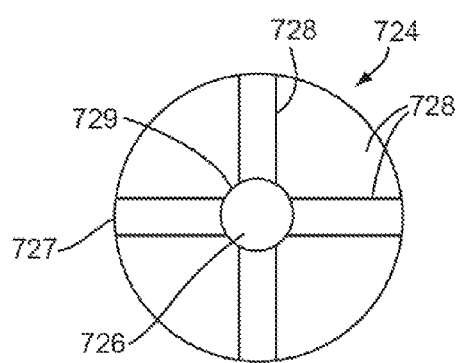
Figure 48C:
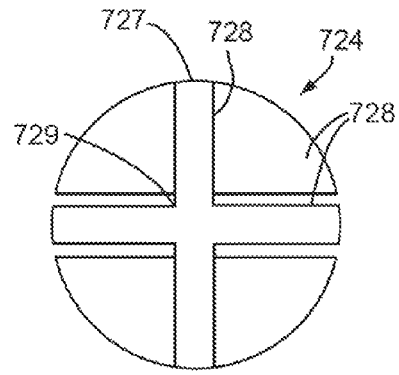

As shown in FIGS. 48A-48C, the beads 724 may include a plurality of individual annular bodies, e.g., each defining a portion of a generally cylindrical or spherical shape. The beads 724 may be formed from desired materials, e.g., metals, such as stainless steel, Nitinol, titanium, and the like, plastic materials, or composite materials, similar to other embodiments herein. Optionally, a desired finish may be applied to the beads 724, e.g., by sand blasting, etching, vapor deposition, and the like, also similar to other embodiments herein.

As best seen in FIG. 48B, each bead 724 may include a passage 726 therethrough for receiving the core wire 722 (not shown) therethrough. In addition, the beads 724 include surface geometries to enhance reflection of electromagnetic waves and/or ultrasound waves. For example, as shown, each bead 724 may define outer cruciform surfaces 727 extending around an outer surface of the bead 724 and a plurality of inward extending surfaces 728 defining dihedral or trihedral corners 729 therebetween, which may enhance detection using radar and/or ultrasound, similar to other embodiments herein.

Figure 49A:
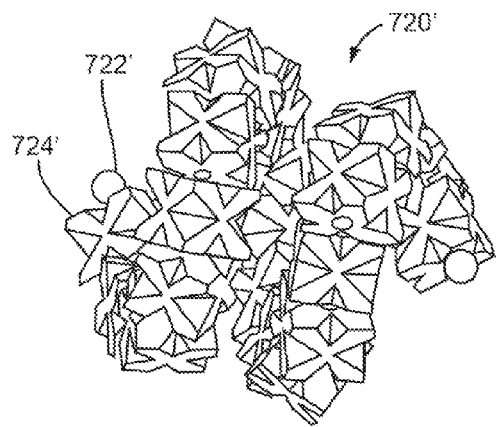
FIGS. 49A and 49B are a side and end views of yet another exemplary embodiment of a marker including a plurality of beads carried on a core wire and defining a wave shape in its deployed configuration.
Figure 49B:
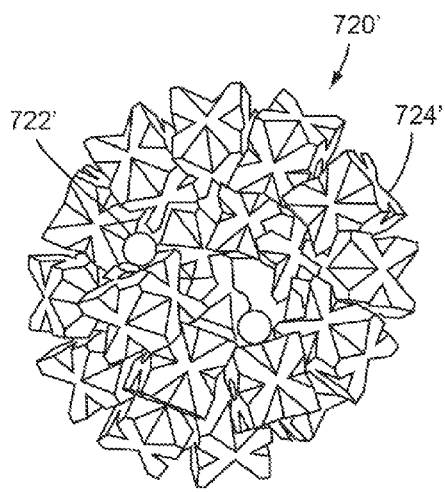
Figure 50A:
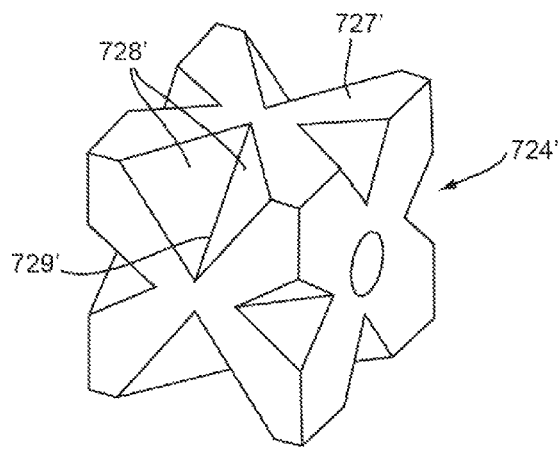
FIGS. 50A-50C are perspective, end, and side views, respectively, of a bead that may be used for making an implantable marker, such as the marker of FIGS. 49A and 49B.
Figure 50B:
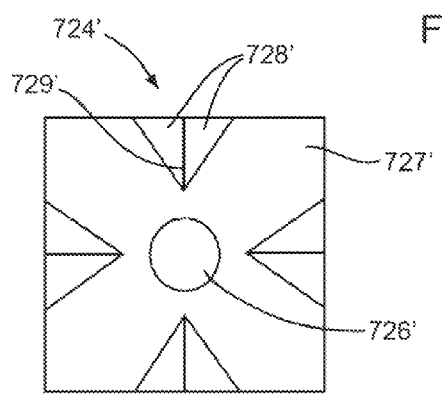
Figure 50C:
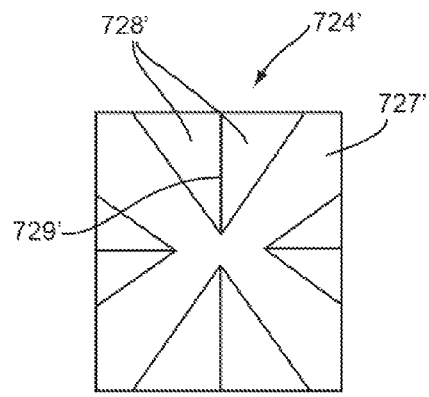

In an alternative embodiment, shown in FIGS. 49A and 49B, another embodiment of a marker 720' is shown, generally similar to the marker 720, except that the beads 724' have generally cubic shapes rather than spherical. As shown in FIGS. 50A-50C, each bead 724' may include substantially planar outer surfaces 727,' e.g., defining a substantially flat cruciform shape, and a plurality of inward extending surfaces 728' defining dihedral corners 729' therebetween. The surfaces 728, 728' may intersect one another and/or the outer surfaces 727, 727' at desired angles, e.g., substantially orthogonally, such as at ninety degrees (90°).

During assembly, a plurality of beads 724, 724' may be placed over and secured to the core wire 722, 722' to provide a finished marker 720, 720,' similar to other embodiments herein. For example, with reference to FIGS. 47A-48C, the core wire 722 may be inserted successively through the passages 726 in the beads 724 until beads 724 extend substantially between the ends of the core wire 722. The beads 724 may be secured to the core wire 722, e.g., by crimping individual beads 724 onto the core wire 722, crimping or otherwise expanding the ends of the core wire 722 after sliding on sufficient beads 724, bonding with adhesive, fusing, and the like. Thus, the beads 724 may be substantially permanently attached to the core wire 722 such that the beads 724 cannot move or the beads 724 may be free floating on the core wire 722.

As shown in FIGS. 47A-47B and 49A-49B, the marker 720, 720' may be biased to assume a tapered helical shape, e.g., a prolate spheroid shape, including a relatively wide intermediate region between tapered end regions, similar to other embodiments herein.

Turning to FIGS. 51-53, another embodiment of a delivery device 760 is shown that may be used for delivering a marker, such as the marker 720 shown in FIGS. 47A and 47B (or any of the other markers described elsewhere herein). The delivery device 760 includes a needle or other tubular shaft 762 including a proximal end 762a and a distal end 762b sized for introduction through tissue into a target tissue region, e.g., within breast 41, and a lumen 764 extending between the proximal and distal ends 762a, 762b. The delivery device 760 also includes a plunger (not shown) slidable within the shaft 762 for delivering the marker 720 from the lumen 764 and an actuator (also not shown) for advancing the plunger and/or retracting the shaft 762, similar to other embodiments herein. As shown, the distal end 762b of the shaft 762 may be beveled and/or otherwise sharpened such that the shaft 762 may be introduced directly through tissue. Alternatively, the delivery device 760 may be introduced through a cannula, sheath, or other tubular member (not shown) placed through tissue, e.g., as described elsewhere herein. Optionally, the distal end 762b may include a band or other feature (not shown), e.g., formed from radiopaque, echogenic, or other material, which may facilitate monitoring the distal end 762b during introduction, e.g., using x-ray or ultrasound imaging, also as described elsewhere herein.

The delivery device 760 may be used to deliver a marker 720 into a breast 41 or other tissue structure, e.g., within a target tissue region including one or more lesions 142, similar to the previous embodiments. Once the marker 720 is delivered, the marker 720 may be used to localize the target tissue region, e.g., using any of the systems and methods described elsewhere herein, as represented by probe 30 in FIG. 53.

For example, as shown in FIG. 51, the distal end 762b of the shaft 762 may be inserted through tissue 40 into the target tissue region, e.g., within lesion(s) 142, as best seen in FIG. 51A. Once the distal end 762b has been advanced or otherwise positioned at a desired location within the tissue 40, the shaft 762 may be retracted relative to the plunger to deliver the marker 720 from the lumen 664, as shown in FIGS. 52 and 53. As shown, the marker 720 may automatically and/or resiliently change shape upon deployment, e.g., returning towards its tapered helical shape or other shape, as best seen in FIGS. 52A and 53A. For example, as the marker 720 is initially deployed, it may "self-bore" into the tissue 40, e.g., along a helical path, as shown in FIGS. 52A and 52B, which may enhance securing the marker 720 within the tissue 40. Thus, the deployed configuration of the marker 720 may resist or prevent migration of the marker 720 relative to the lesion 142 after implantation.

As shown in FIG. 53, the delivery device 760 may then be withdrawn from the breast 41 leaving the marker 720 within the target tissue region, e.g., within lesion(s) 142.

Although the systems and methods described above relate to lesions within breasts, one or more markers or targets may be implanted or otherwise introduced into other regions of a patient's body for subsequent localization using a probe, such as probe 30 described above. For example, one or more targets may be placed within or adjacent a bile duct, femoral artery or vein, fallopian tube, or other body lumen for subsequent localization. The target(s) may be carried by a catheter, wire, or other delivery device within the lumen of the body lumen from a remote access site and secured therein, e.g., by immobilizing the catheter or wire, or by anchoring the marker(s) to, within, or through the wall of the body lumen or otherwise within the body lumen.

Figures 54, 55:
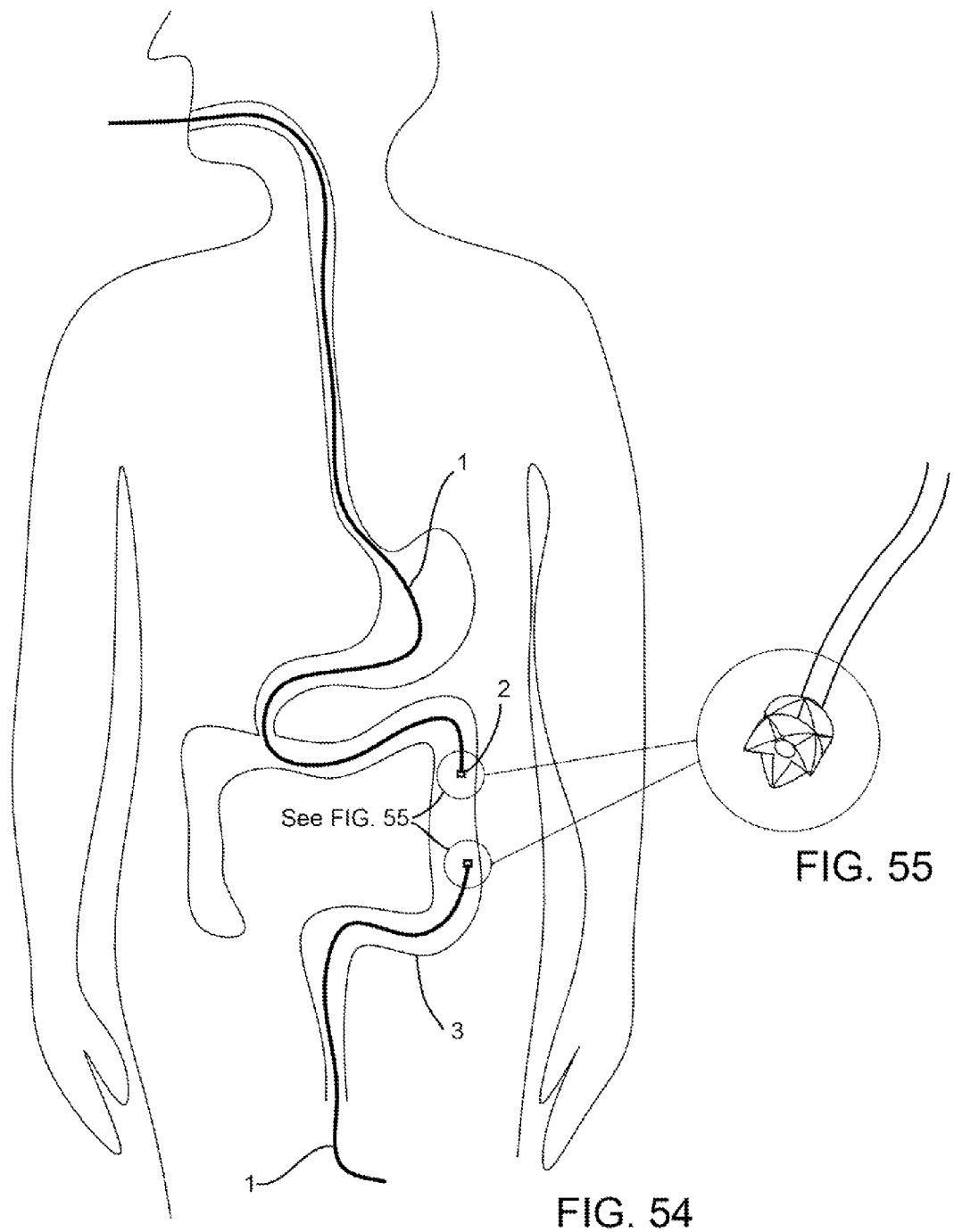
FIG. 54 is a cross-sectional view of a patient's body showing markers being introduced into the patient's gastrointestinal system.
FIG. 55 is a detail of a marker that may be introduced into the patient's body shown in FIG. 54.

For example, FIG. 54 shows a gastrointestinal tract 3 of a patient upon whom one or more diagnostic and/or therapeutic procedures are to be performed. As shown, a catheter 1 carrying a marker 2 may be introduced into the patient's GI tract 3, e.g., via, the mouth or rectum. As can be seen in FIG. 55, the catheter 1 may include a marker 2, e.g., similar to the other markers described elsewhere herein. For example, the marker 2 may include features similar to one or more of the beads 320 shown in FIGS. 23A-23C and described above. The catheter 1 and marker 2 may be advanced to a desired location within the GI tract 3, e.g., using fluoroscopy, ultrasound, or other external imaging.

Figure 56:
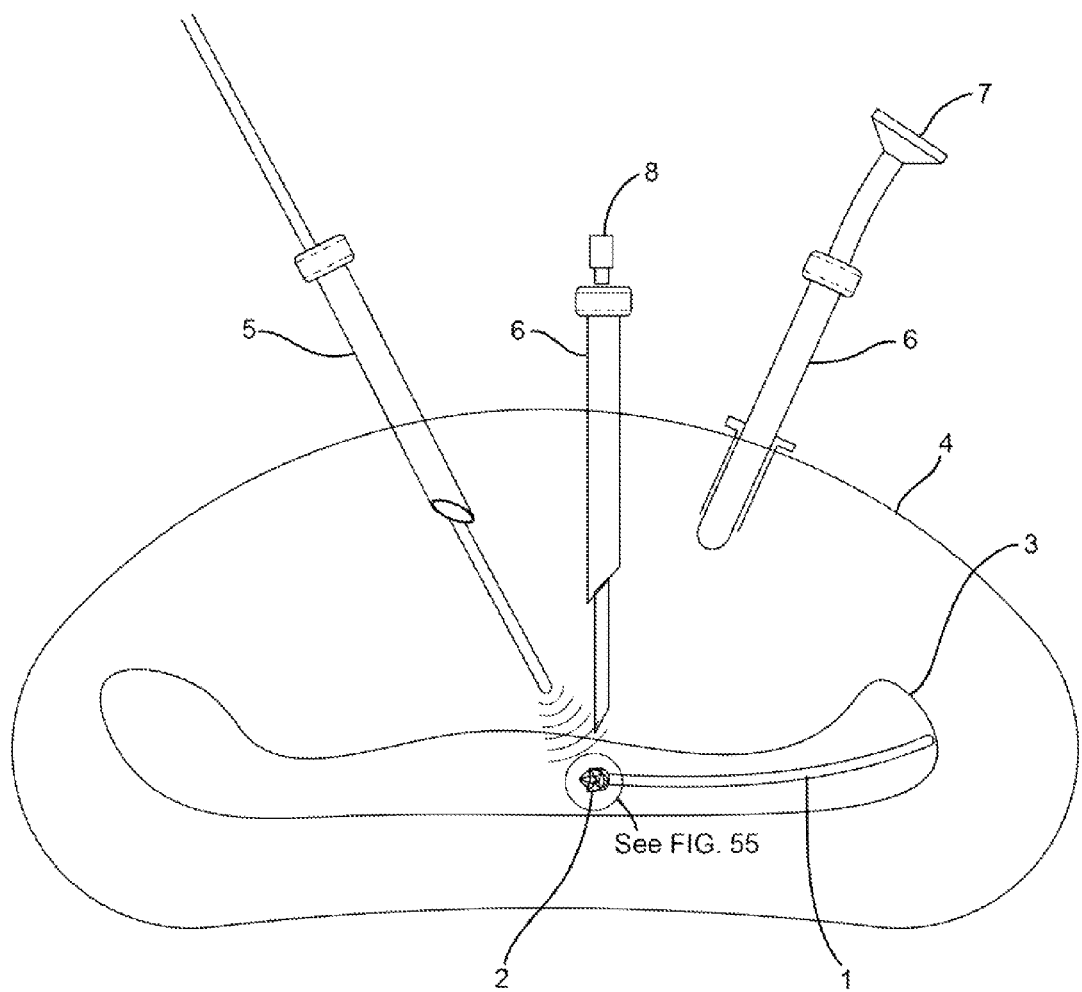
FIG. 56 is a detail of the patient's body of FIG. 54, showing instruments being introduced into the patient's body based at least in part on the location of a marker introduced into the patient's gastrointestinal system in order to perform a procedure.

A probe, such as any of those described elsewhere herein, may then be used to locate the marker 2, and thereby locate the location in the GI tract 3. It will be appreciated that other body lumens may be localized in a similar manner, e.g., to facilitate access to the body lumen, e.g., in a minimally invasive manner from outside the patient's body. For example, as shown in FIG. 56, the marker 2 may be used to locate a particular location in the GI tract 3, e.g., to facilitate puncturing the wall and enter the body lumen, to clip, cut, ligate, or otherwise close the body lumen, and the like. FIG. 56 is a cross-sectional view of an insufflated abdomen 4, e.g., using conventional laparoscopic procedures. A probe 5, which may be similar to any of the probes described elsewhere herein, may be inserted through an access cannula 6 to scan and/or detect the location of the marker 2 on the catheter 1. A laparoscope 7 may then be used to visualize the position of the probe 5 relative to the marker 2. Once the marker 2 has been located, an access sheath 8 may be used to gain access to the GI tract 3 at the desired location, e.g., to perform one or more diagnostic and/or therapeutic procedures. The marker 2 and catheter 1 may be removed once access is achieved or after the procedure(s) is complete, as desired.

In an exemplary embodiment, a marker may be introduced into a fallopian tube using a catheter, and then a needle or other device may be introduced in a minimally invasive manner, e.g., punctured through the patient's skin and tissue above the marker to access the fallopian tube, for example, to ligate, cauterize, or otherwise sever or close the fallopian tube. Alternatively, if a marker is placed within a bile duct, endoscopic access may be used under guidance of the probe 30 to access the bile duct, e.g., to perform a procedure within a patient's intestine. In a further alternative, markers may be placed in branches communicating with a length of femoral artery, vein, or other vessel intended for harvest, and then the probe 30 may be used to localize each of the branches external to the vessel, e.g., such that each branch may be cut, ligated, cauterized, and/or otherwise separated, to allow the length of vessel to be separated from the adjacent vessels and harvested.

In a further alternative, one or more markers may be implanted within a target tissue structure for localized therapy using the systems described herein. For example, the marker(s) may carry one or more drugs, radioactive material, or other therapeutic substances that may be released over an extended time within or around the target tissue region in which they are implanted. After sufficient time, e.g., after the therapeutic substance(s) have been substantially completely depleted or otherwise sufficiently delivered, the probe 30 may be used to localize the marker(s) to facilitate recovering and/or removing the marker(s), e.g., in a minimally invasive manner.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for localizing a target tissue region within a patient's body, comprising:
   implanting a target in the target tissue region within a breast of the patient's body, the target comprising a single core member having a first wire end and a second wire end generally opposite the first wire end, and an electronic circuit carried by the core member configured to provide an active reflector antenna; and
   placing a probe adjacent the target tissue region, the probe transmitting micro-impulse radar signals towards the target tissue region, receiving signals reflected from the target, and displaying spatial information to provide a spatial relationship between the target and the probe based on the reflected signals, the spatial relationship comprising a distance from the probe to the target;
   wherein the electronic circuit modulates signals from the probe that strike the target such that the signals reflected from the target enhance identification of the target by the probe.

2. The method of claim 1, wherein implanting the target in the target tissue region comprises:
   introducing a delivery device percutaneously through tissue into the target tissue region carrying the target in a first delivery configuration; and
   deploying the target from the delivery device whereupon the target resiliently returns to a deployed configuration within the target tissue region.

3. The method of claim 2, wherein the first delivery configuration comprises the core member being in a substantially linear configuration and wherein the deployed configuration comprises the core member being in a curvilinear configuration.

4. The method of claim 1, wherein the electronic circuit changes a phase of the signals reflected from the target.

5. The method of claim 1, wherein the probe transmits the micro-impulse signals at ultrawide band frequencies ("UWB") between about three and ten Gigahertz (3-10 GHz).

6. The method of claim 1, further comprising successively placing the probe at multiple locations on the patient's skin to obtain spatial information comprising a distance between the probe and the target from each of the multiple locations.

7. The method of claim 6, wherein the probe is placed successively at the multiple locations on the patient's skin to determine an optimal approach path for dissection to a lesion within the breast.

8. The method of claim 7, further comprising:
dissecting tissue along the determined approach path to the lesion; and
removing a tissue specimen from the target tissue region, the tissue specimen including the lesion and the target.

9. The method of claim 8, further comprising placing the probe against exposed tissue while dissecting the tissue to obtain spatial information between the probe and the target to confirm at least one of the determined approach path to the lesion and depth of dissection.

10. A method for localizing a target tissue region within a patient's breast, comprising:
implanting a target in the target tissue region within the patient's breast, the target comprising a single elongate core member having a first wire end and a second wire end and an electronic circuit carried by the core member including one or more diodes and FET transistors configured to provide an active reflector antenna;
placing a substantially flat patient contact surface of a handheld probe against the patient's skin adjacent the target tissue region; and
activating the probe, whereupon the probe transmits micro-impulse radar signals towards the target tissue region, receives signals reflected from the target that are modulated by the electronic circuit, and provides an output comprising spatial information comprising a distance between the target and the probe based at least in part on the reflected signals.

11. The method of claim 10, wherein the spatial information further comprises a relative angular orientation between the target and the probe.

12. The method of claim 10, wherein implanting the target comprises advancing a localization wire through intervening tissue into the target tissue region, the localization wire carrying the target.

13. The method of claim 10, wherein the target tissue region comprises a region within the patient's breast having a lesion therein.

14. The method of claim 13, wherein the target is implanted in the lesion.

15. The method of claim 13, further comprising removing a tissue specimen from the target tissue region, the tissue specimen including the lesion and the target.

16. The method of claim 10, wherein the target is implanted in the target tissue region by introducing a delivery device carrying the target through intervening tissue into the target tissue region.

17. The method of claim 10, wherein the target has a length no greater than four millimeters (4.0 mm).

18. The method of claim 10, wherein implanting a target in the target tissue region comprises:
introducing the target through breast tissue into the target tissue region with the single elongate core member of the target in a substantially linear delivery configuration; and
deploying the target within the target tissue region, the single elongate core member of the target resiliently returning to a curvilinear deployed configuration.

19. The method of claim 10, wherein the electronic circuit changes a phase of the signals reflected from the target.

20. The method of claim 10, wherein the probe transmits the micro-impulse signals at ultrawide band frequencies ("UWB") between about three and ten Gigahertz (3-10 GHz).

21. The method of claim 10, further comprising successively placing the probe at multiple locations on the patient's skin to obtain spatial information comprising a distance between the probe and the target from each of the multiple locations.

22. The method of claim 21, wherein the probe is placed successively at the multiple locations on the patient's skin to determine an optimal approach path for dissection to a lesion within the breast.

23. The method of claim 22, further comprising:
dissecting tissue along the determined approach path to the lesion; and
removing a tissue specimen from the target tissue region, the tissue specimen including the lesion and the target.

24. The method of claim 23, further comprising placing the probe against exposed tissue while dissecting the tissue to obtain spatial information between the probe and the target to confirm at least one of the determined approach path to the lesion and depth of dissection.

25. A method for removing a lesion within a target tissue region of a patient's breast, comprising:
providing a target comprising a single core member having a first wire end and a second wire end and an electronic circuit carried by the core member including one or more diodes and FET transistors configured to provide an active reflector antenna;
introducing the target through breast tissue into the target tissue region with the first and second wire ends aligned in a substantially linear delivery configuration;
deploying the target within the target tissue region, the core member of the target resiliently returning to a curvilinear deployed configuration;
placing a probe against the patient's skin adjacent the target tissue region, the probe transmitting micro-impulse radar signals towards the target tissue region, receiving signals reflected from the target, and providing an output related to a distance from the probe to the target;
determining, using the probe, a desired margin within the target tissue region around the lesion; and
removing a tissue specimen from the target tissue region, the tissue specimen defined by the desired margin and including the lesion and the target.

26. The method of claim 25, wherein the target has a length no greater than four millimeters (4.0 mm).

27. The method of claim 25, wherein the single core member is biased to a helical shape in the deployed configuration defining a helical axis and wherein the first and second wire ends spiral around the helical axis.

28. The method of claim 25, wherein a patient contact surface of the probe is successively placed and activated at multiple locations on the patient's skin to obtain spatial information providing a spatial relationship between the target and the probe and to determine the desired margin.

* * * * *